(12) United States Patent
Xu et al.

(10) Patent No.: US 11,895,994 B2
(45) Date of Patent: Feb. 13, 2024

(54) HUMANIZED KNOCK-IN MOUSE EXPRESSING HUMAN PROTEIN C

(71) Applicant: Shanghai RAAS Blood Products Co., Ltd., Shanghai (CN)

(72) Inventors: Jun Xu, Shanghai (CN); Lu Cheng, Shanghai (CN); Yeheng Liu, Shanghai (CN); Jiawei Yi, Shanghai (CN); Xuefeng Zhou, Shanghai (CN)

(73) Assignee: Shanghai RAAS Blood Products Co., Ltd., Shanghai (CN)

( * ) Notice: Subject to any disclaimer, the term of this patent is extended or adjusted under 35 U.S.C. 154(b) by 471 days.

(21) Appl. No.: 17/011,292

(22) Filed: Sep. 3, 2020

(65) Prior Publication Data

US 2021/0120789 A1   Apr. 29, 2021

(30) Foreign Application Priority Data

Oct. 27, 2019   (CN) .......................... 201911027061.6
Oct. 29, 2019   (GB) ....................................... 1915689

(51) Int. Cl.
*A01K 67/027*   (2006.01)
*C12N 5/0735*   (2010.01)
*C12N 15/85*   (2006.01)

(52) U.S. Cl.
CPC ...... *A01K 67/0278* (2013.01); *A01K 67/0276* (2013.01); *C12N 5/0606* (2013.01); *C12N 15/8509* (2013.01); *A01K 2207/15* (2013.01); *A01K 2217/052* (2013.01); *A01K 2227/105* (2013.01); *A01K 2267/03* (2013.01); *C12N 2015/8527* (2013.01)

(58) Field of Classification Search
CPC ............ A01K 67/0278; A01K 67/0276; A01K 2207/15; A01K 2217/052; A01K 2227/105; G01N 2333/96461
See application file for complete search history.

(56) References Cited

U.S. PATENT DOCUMENTS

| 5,831,141 A | 11/1998 | Lubon et al. |
| 6,066,778 A | 5/2000 | Ginsburg et al. |
| 2005/0125851 A1 | 6/2005 | Whitsett et al. |
| 2012/0082987 A1 | 4/2012 | Sasgary et al. |
| 2012/0192298 A1 * | 7/2012 | Weinstein .......... C12N 15/8509 435/325 |

FOREIGN PATENT DOCUMENTS

| CN | 102690803 | 9/2012 |
| CN | 107929719 | 4/2018 |
| EP | 0 319 312 A2 | 6/1989 |
| EP | 0 319 312 A3 | 9/1990 |
| WO | WO 1997/020043 | 6/1997 |
| WO | WO 2002/096947 | 12/2002 |
| WO | WO 2004/056310 | 7/2004 |
| WO | WO 2017/044864 | 3/2017 |
| WO | WO 2018/022777 | 2/2018 |
| WO | WO 2018/023014 | 2/2018 |

OTHER PUBLICATIONS

Jalbert et al (Inactivation of the Gene for Anticoagulant Protein C Causes Lethal Perinatal Consumptive Coagulopathy in Mice. J Clin. Invest., vol. 102, Oct. 1998. Cited in IDS dated Sep. 11, 2020) (Year: 1998).*
Raife et al (Human Thrombomodulin Knockin Mice Reveal Differential Effects of Human Thrombomodulin on Thrombosis and Atherosclerosis. Arterioscler Thromb Vasc Biol., vol. 31, Nov. 2011. Cited in IDS dated Mar. 5, 2021) (Year: 2011).*
NCBI Reference Sequence: NM_000312.3 (Year: 1985).*
Foster et al (The nucleotide sequence of the gene for human protein C. PNAS, vol. 82, Jul. 1985). (Year: 1985).*
Stagaard et al (Absence of functional compensation between coagulation factor VIII and plasminogen in double-knockout mice. Blood Advances, vol. 2, Nov. 2018). (Year: 2018).*
Bernard et al (Efficacy and Safety of Recombinant Human Activated Protein C for Severe Sepsis. NEJM, vol. 344, Mar. 2001). (Year: 2001).*
Lay et al (Mice with a severe deficiency in protein C display prothrombotic and proinflammatory phenotypes and compromised maternal reproductive capabilities. J Clin. Invest., vol. 115, Jun. 2005. Cited in IDS dated Mar. 5, 2021) (Year: 2005).*
Krisinger et al (Mouse recombinant protein C variants with enhanced membrane affinity and hyper-anticoagulant activity in mouse plasma. FEBS, vol. 276, 2009. Cited in the IDS dated Sep. 11, 2020) (Year: 2009).*
Barefield et al., Phosphorylation and function of cardiac myosin binding protein-C in health and disease; J Mol Cell Cardiol., 2010; 48(5):866-875.
Ranjan et al., Activated protein C protects from GvHD via PAR2/PAR3 signalling in regulatory T-cells; Nat. Comm., 2017; 8(1):311. doi: 10.1038/s41467-017-00169-4.
Mosnier LO et al., The cryptoprotective protein C pathway, Blood 109:2161-3172 (2007).
Lay AJ et al., Mice with a severe deficiency in protein C display prothrombotic and proinflammatory phenotypes and compromised . . . , J. Clin. Invest. 115:1552-1561 (2005).
Chan JCY et al., The Characterization of Mice with a Targeted Combined Deficiency of Protein C and Factor XI, Am. J. Pathol., 158:469-479 (2001).
Raife TJ et al, Human Thrombomodulin Knockin Mice Reveal Differential Effects of Human Thrombomodulin on Thrombosis . . . , Arterioscler. Throm. Vasc. Biol. 31:2509-2517 (2011).

(Continued)

*Primary Examiner* — Valarie E Bertoglio
*Assistant Examiner* — Matasha Dhar
(74) *Attorney, Agent, or Firm* — Grimes & Yvon LLP

(57) ABSTRACT

Provided is a genetically modified non-human animal, in which at least one copy of the endogenous nucleotide sequence encoding Protein C in the genome of said the non-human animal has been replaced by a nucleotide sequence encoding human Protein C or a functional fragment or variant thereof. Also provided are vectors, cells, and methods for the production of such non-human animals. Further provided are methods of testing agents for their ability to alter to the level and/or functional activity of human protein C, for example, to test their potential therapeutic efficacy.

6 Claims, 17 Drawing Sheets

Figure 1:
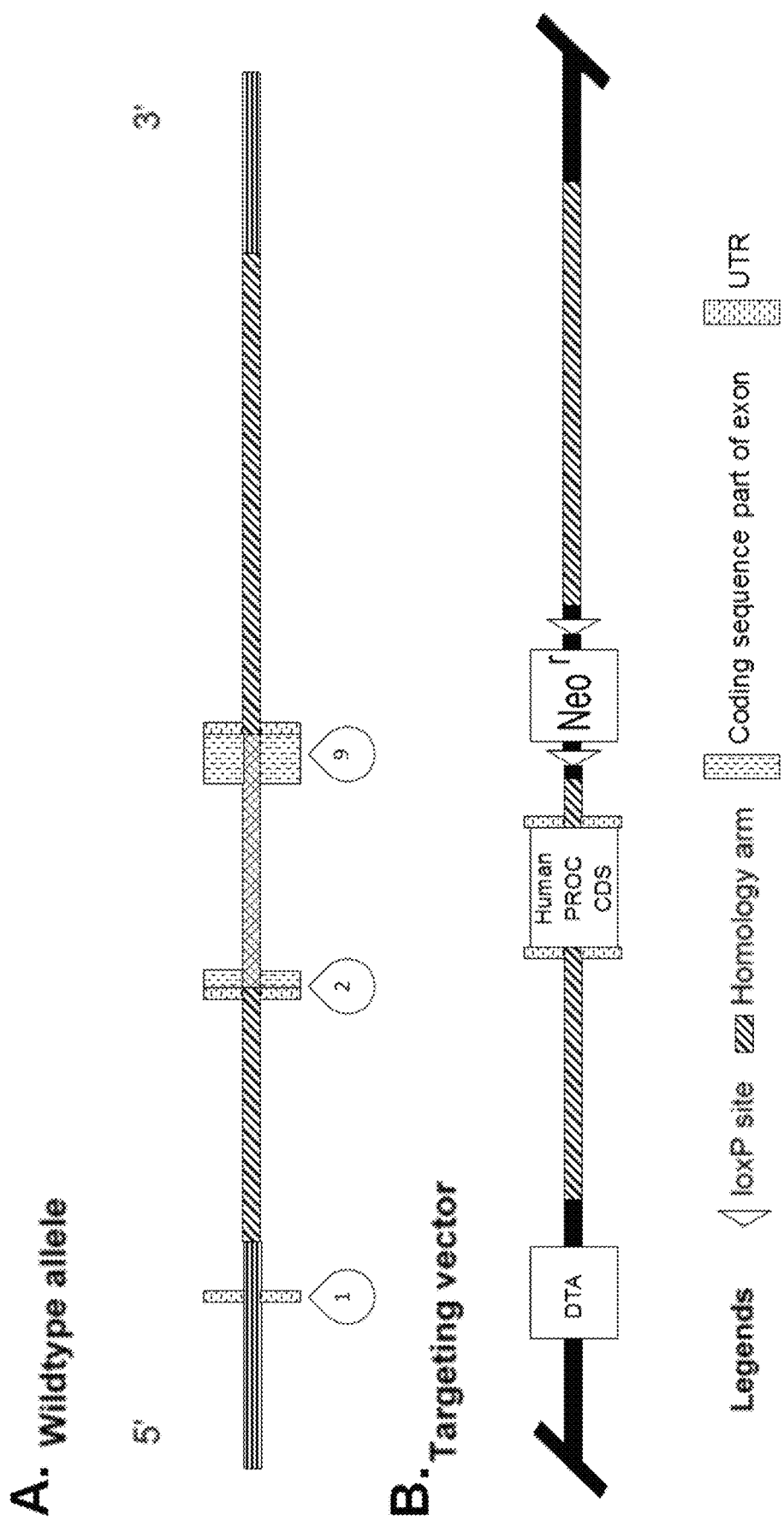
Figure 1:
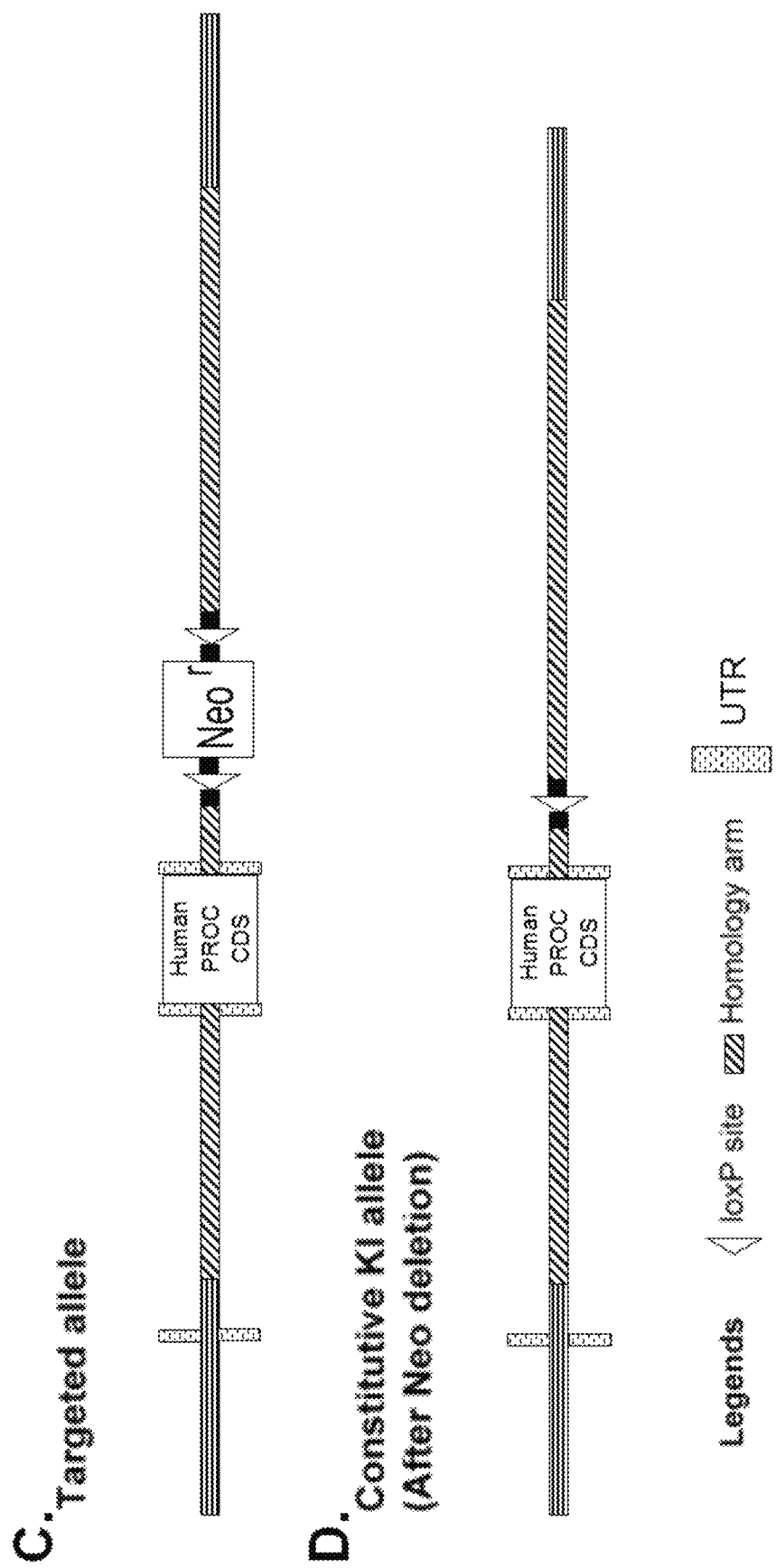

Specification includes a Sequence Listing.

(56) References Cited

OTHER PUBLICATIONS

Polderdijk et al., Targeting activated protein C to treat hemophilia, Curr. Opin. Hematol., 2017, 24: 446-452.

Krisinger et al., Mouse recombinant protein C variants with enhanced membrane affinity and hyper-anticoagulant activity in mouse plasma, FEBS Journal, 2009, 276:6586-6602.

Jalbert et al., Inactivation of the Gene for Anticoagulant Protein C Causes Lethal Perinatal Consumptive Coagulopathy in Mice, J. Clin. Invest., 1998, 102(8): 1481-8.

Polderdijk and Huntington, Identification of serpins specific for activated protein C using a lysate-based screening assay, 2018, Scientific Reports, 8:8793.

Tada et al., Isolation and Characterization of a Mouse Protein C cDNA, J. Biochem. 111, 491-495 (1992).

Malm et al., Human activated protein C variants in a rat model of arterial thrombosis, Thrombosis Journal 2008, 6:16 doi:10.1186/1477-9560-6-16.

Xu et al., Endogenous activated protein C signaliing is critical to protection of mice from . . . septic shock, Journal of Thrombosis and Haemostasis, 7: 851-856 (2009).

\* cited by examiner

Enzyme digestion of final vector

1. ApaLI: 7.4/4.3/3.2/1.5/1.2
2. AhdI: 7.5/4.9/3.1/2.0/0.1
3. FspI/HindIII: 6.3/4.1/3.0/1.6/1.5/1.2
4. NcoI: 7.6/4.6/2.6/1.6/0.6/0.6/0.1
5. SacI: 4.6/3.6/3.0/1.7/1.6/1.4/0.8/0.6/0.3
6. NotI: 17.6

A.
Marker KI1 PCR, clone: 3C4 (WT: N.A.;MT: 380 bp)

B.
KI2 PCR, clone: 3C4 (WT: N.A.;MT: 324 bp)

C.
Neo deletion PCR, clone: 3C4 (WT: 298 bp; MT: 230 bp)

A

B

HUMANIZED KNOCK-IN MOUSE EXPRESSING HUMAN PROTEIN C

This application claims the benefit of priority of China Patent Application No. 201911027061.6, filed on Oct. 27, 2019, and of Great Britain Patent Application No. 1915689.2, filed on Oct. 29, 2019, the entire contents of which are incorporated by reference herein.

The instant application contains a Sequence Listing which has been submitted electronically in ASCII format and is hereby incorporated by reference in its entirety. Said ASCII copy, created on Sep. 2, 2020, is named Dehns_002_US1_SL.txt and is 68,680 bytes in size.

The present invention relates generally to genetically modified non-human animals. In particular, the present invention relates to a "knock-in" non-human animal in which a nucleotide sequence encoding an endogenous protein in the genome of the non-human animal has been replaced with a homologous human nucleotide sequence that encodes a homologous human protein. The invention also provides vectors, cells and methods for the production of such non-human animals. The invention also provides methods of testing agents for their ability to alter to the level and/or functional activity of the human protein in vivo and thus provides methods of testing agents for their potential therapeutic efficacy.

The human Protein C pathway plays a critical role in regulating coagulation (blood clotting) and inflammation. Human Protein C is activated by thrombin complexed with thrombomodulin (TM) on endothelium. Protein C is a zymogen that is converted by the thrombomodulin (TM)/Thrombin complex to Activated Protein C (APC).

Activated Protein C (APC) is a serine protease. APC cleaves activated factor V and activated factor VIII and thus negatively down-regulates thrombin formation, which is critical for maintaining the balance of thrombosis and hemostasis in vivo. Put another way, APC inhibits major driving forces of coagulation. Thus, APC has an important anticoagulant function, with APC's major targets being activated Factor V and activated Factor VIII. Human APC also contributes to the enhanced fibrinolytic response by complex formation with plasminogen activator inhibitor.

In view of its important physiological activity, protein C/APC has become an attractive therapeutic target. For example, given its important role as an anticoagulant in the regulation of clotting, Protein C/APC has been identified as a therapeutic target in the context of haemophilia (Polderdijk et al., *Curr. Opin. Hematol.*, 2017, 24: 446-452). Haemophilia is a serious bleeding disorder, typically characterized by a deficiency or defect in factor VIII or factor IX. Treatment of haemophilia typically involves the preventative, or on-demand, administration of the missing or defective factor. Such treatments are expensive and patients undergoing such treatments can develop inhibitory antibodies to the administered factor that necessitate the use of "bypassing" agents. Alternative, and preferably improved, treatments for haemophilia are needed.

In addition to its anti-coagulant functions, APC has cytoprotective activities, including anti-inflammatory and anti-apoptotic activities, and protection of endothelial barrier function (discussed in Krisinger et al., *FEBS Journal*, 2009, 276:6586-6602). Thus, APC is also an attractive therapeutic target in the context of diseases characterized by inflammation and/or apoptosis. For example, APC is an attractive therapeutic target in the context of sepsis.

Although there are multiple important functions of protein C and APC, a comprehensive in vivo study of protein C and APC is still lacking. This type of in vivo study has not been possible due to the neonatal lethality of mice lacking protein C (Jalbert et al., *J. Clin. Invest.*, 1998, 102(8): 1481-8).

Human protein C (or human APC), which is of course the relevant target in potential therapies in humans, has an amino acid sequence that is significantly different from its mouse orthologue. Mouse Protein C and human Protein C have only 69% amino acid sequence identity. This significant difference in sequence (structure) between mouse protein C and human Protein C means that studying mouse Protein C (e.g. the effects of potential therapeutic agents thereon) would not be ideal when human Protein C is the protein of interest. Furthermore, interspecies ex vivo experiments indicate that human protein C does not function efficiently in mouse plasma (discussed in Krisinger et al., *FEBS Journal*, 2009, 276:6586-6602).

Genetically modified non-human animals, such as mice, in which human Protein C is expressed instead of the endogenous non-human Protein C orthologue (e.g. human Protein C "knock-in" animals in which the non-human Protein C orthologue has been removed e.g. "knocked-out") would, if they could be generated, represent very useful models for studying human Protein C in vivo, for example, for testing potential therapeutic agents that target human Protein C. However, as mice lacking Protein C (i.e. lacking mouse Protein C) are neonatal lethal and human protein C has been reported as not efficiently functioning in mouse plasma, the suggestion based on the knowledge in the art discussed above is that the provision of such a genetically modified animal, e.g. a mouse, would not be possible.

However, surprisingly, the present inventors have been able to generate such genetically modified mice. These mice are viable, appear healthy and have bleeding characteristics that are in line with the bleeding characteristics of relevant control mice that express endogenous mouse Protein C and not human Protein C.

Thus, in a first aspect, the present invention provides a genetically modified non-human animal, in which at least one copy of the endogenous nucleotide sequence encoding Protein C in the genome of said non-human animal has been replaced by a nucleotide sequence encoding human Protein C, encoding a functional fragment of human Protein C or encoding a functional variant of human Protein C.

In some embodiments, the non-human animal is a non-human mammal. In some embodiments, the non-human animal is a rodent. In some embodiments, the non-human animal is a mouse or a rat, preferably a laboratory mouse or rat.

A preferred non-human animal in accordance with the invention is a mouse. Preferably, the mouse is a laboratory mouse. A particularly preferred strain of mouse is C57BL/6.

The non-human animals of the present invention are genetically modified. This of course means that these animals are not naturally occurring animals, i.e. are not native or wildtype animals. The genetic modification is established by technical means, e.g. as described elsewhere herein. In accordance with the present invention, the genetic modification includes the replacement of at least one copy of the endogenous nucleotide sequence encoding Protein C in the genome of said non-human animal by a nucleotide sequence encoding human Protein C, encoding a functional fragment of human Protein C or encoding a functional variant of human Protein C.

Non-human animals of the invention express, or are capable of expressing, human Protein C, a functional fragment of human Protein C or a functional variant of human Protein C.

An endogenous nucleotide sequence encoding Protein C means a nucleotide sequence that encodes Protein C that is wildtype (or native or endogenous) to the non-human animal.

The coding sequence (CDS) of endogenous Protein C is the nucleotide sequence that encodes (or corresponds to) the sequence of amino acids in Protein C protein. The CDS starts with a start codon (typically ATG) and ends with a stop codon (e.g. TAG). However, as the skilled person is aware, in the context of an endogenous animal gene (i.e. in a genomic context) the coding sequence of Protein C (which is present in exons) is typically interrupted by introns, meaning that, in the endogenous gene itself, the CDS is present as a discontinuous sequence of nucleotides.

Thus, in preferred embodiments of the present invention, the endogenous nucleotide sequence encoding Protein C that has been replaced is all or part of the nucleotide sequence that begins at the start codon and ends at the stop codon, including other exon sequences and intron sequences between the start codon and the stop codon. In preferred embodiments, the entire (i.e. all of) nucleotide sequence from the start codon to the stop codon, including other exon sequences and intron sequences between the start codon and the stop codon, has been replaced.

As indicated above, a mouse is a particularly preferred non-human animal in accordance with the invention. Mouse Protein C means Protein C that is wildtype (or native) to a mouse. The amino acid sequence of mouse Protein C is set forth herein as SEQ ID NO:12. A nucleotide coding sequence (CDS) of mouse Protein C is set forth herein as SEQ ID NO:10. The mouse Protein C (Proc) gene (NCBI Reference Sequence: NM_001042767.3) is located on mouse chromosome 18. Nine exons have been identified, with the start codon (ATG) located in exon 2 and the stop codon (TAG) located in exon 9.

Thus, in preferred embodiments of the present invention, the endogenous nucleotide sequence encoding mouse Protein C that has been replaced is all or part of the nucleotide sequence from the start codon (ATG) in exon 2 of the mouse Protein C gene to the stop codon in exon 9 of the mouse Protein C gene, including other exon sequences and intron sequences between the start codon and the stop codon. In preferred embodiments, the entire (i.e. all of) the nucleotide sequence from the start codon (ATG) in exon 2 of the mouse Protein C gene to the stop codon in exon 9 of the mouse Protein C gene, including other exon sequences and intron sequences between the start codon and the stop codon, is replaced.

As a result of the replacement of at least one copy of an endogenous nucleotide sequence encoding Protein C in accordance with the present invention, at least one allele of the Protein C gene in the non-human animal does not encode Protein C that is wildtype (or native) for that animal. Accordingly, at least one allele of the Protein C gene in the non-human animal does not express (and is not capable of expressing) an mRNA encoding Protein C that is wildtype (or native) for that animal.

In the case of mice, at least one allele of the Protein C gene in a genetically modified mouse of the invention does not encode Protein C that is wildtype (or native or endogenous) for the mouse. Accordingly, at least one allele of the Protein C gene in the mouse does not express an mRNA molecule encoding Protein C that is wildtype (or native) for the mouse, e.g. an mRNA molecule encoding SEQ ID NO:12 (e.g. an mRNA having a nucleotide sequence that corresponds to SEQ ID NO:10).

Human Protein C means Protein C that is a wild-type (or native or endogenous) to a human. The amino acid sequence of human Protein C is set forth herein as SEQ ID NO:11. A nucleotide coding sequence (CDS) of human Protein C is set forth herein as SEQ ID NO:8. In the context of the present invention, a nucleotide sequence encoding human Protein C, encoding a functional fragment of human Protein C or encoding a functional variant of human Protein C may be considered a heterologous (or foreign or exogenous) nucleotide sequence.

Preferably, at least one copy of the endogenous nucleotide sequence encoding Protein C in the genome of the non-human animal has been replaced by a nucleotide sequence encoding human Protein C (i.e. full-length or wildtype human Protein C). Thus, preferably, at least one copy of the endogenous nucleotide sequence encoding Protein C in the genome of the non-human animal has been replaced by a nucleotide sequence encoding human Protein C, wherein human Protein C comprises (or consists of) the amino acid sequence of SEQ ID NO:11. An exemplary and preferred nucleotide sequence encoding human Protein C (SEQ ID NO:11) is set forth in SEQ ID NO:8. The nucleotide sequence encoding human Protein C may alternatively comprise (or consist of) a sequence substantially homologous to SEQ ID NO: 8, e.g. a codon degenerate version of SEQ ID NO:8.

Typically and preferably, the nucleotide sequence encoding human Protein C is the coding sequence (CDS) of the human Protein C gene, i.e. excluding introns and untranslated regions UTRs of the human Protein C gene.

In alternative embodiments, the nucleotide sequence encoding human Protein C may additionally comprise intron sequences of the human Protein C gene. In some embodiments, human 5' UTR and/or human 3' UTR nucleotide sequences may additionally be provided. The human Protein C (PROC) gene (NCBI Reference Sequence: NM_000312.3) is located on human chromosome 2. Nine exons have been identified, with the start codon (ATG) in exon 2 and the stop codon (TAG) in exon 9.

In some alternative embodiments, at least one copy of the endogenous nucleotide sequence encoding Protein C in the genome of said non-human animal has been replaced by a nucleotide sequence encoding a functional fragment of human Protein C or encoding a functional variant of human Protein C (i.e. instead of full-length wildtype human Protein C).

A "functional" fragment of human Protein C or a "functional" variant of human Protein C means a fragment or variant that exhibits (or maintains) at least one functional activity of the full-length wildtype human Protein C, e.g. exhibits at least 10%, at least 25%, at least 75%, at least 90% or at least 100% of the level of at least one functional activity of the full-length wildtype human Protein C. The functional activity may be, for example, anticoagulant activity and/or cytoprotective activity (e.g. anti-inflammatory activity and/or anti-apoptotic activity), e.g. as described elsewhere herein.

In some embodiments, a fragment of human Protein C can be at least 100, at least 150, at least 200, at least 250, at least 300, at least 350, at least 400, or at least 450 consecutive amino acids in length. In some embodiments, fragments can be up to 460 consecutive amino acids in length (e.g. 100-460, 200-460, 300-460, or 400-460 consecutive amino acids in length).

In some embodiments, a fragment of human Protein C is a naturally occurring fragment of human Protein C, for example Activated Protein C (APC).

In some embodiments, a variant of human Protein C is a protein having an amino acid sequence that is substantially homologous to the amino acid sequence of full-length wildtype human Protein C (or a fragment thereof).

The term "substantially homologous" as used herein in connection with an amino acid or nucleic acid sequence includes sequences having at least 75%, at least 80%, preferably at least 85%, at least 90%, at least 95%, at least 96%, at least 97%, at least 98% or at least 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain up to 10 or up to 5, e.g. only 1, 2, 3, 4 or 5, preferably 1, 2 or 3, more preferably 1 or 2, altered amino acids. Said alterations can be with conservative or non-conservative amino acids. Preferably, said alterations are conservative amino acid substitutions.

A "conservative amino acid substitution", as used herein, is one in which the amino acid residue is replaced with another amino acid residue having a similar side chain. Families of amino acid residues having similar side chains have been defined in the art, including basic side chains (e.g. lysine, arginine, histidine), acidic side chains (e.g. aspartic acid, glutamic acid), uncharged polar side chains (e.g. asparagine, glutamine, serine, threonine, tyrosine, cysteine), nonpolar side chains (e.g. glycine, cysteine, alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine).

Methods of carrying out manipulation of amino acids and protein domains (e.g. to generate substantially homologous sequences) are well known to a person skilled in the art. For example, said manipulations could conveniently be carried out by genetic engineering at the nucleic acid level wherein nucleic acid molecules encoding appropriate proteins are modified such that the amino acid sequence of the resulting expressed protein is in turn modified in the appropriate way.

Variants of human Protein C (or fragments thereof) also include modified versions of human Protein C (or fragments thereof) such as human Protein C (or fragments thereof) that contain one or more additional amino acids at one or both termini (e.g. contain one or more N-terminal and/or C-terminal fusion moiety or fusion tag or epitope tag). Thus, variants may include fusion proteins comprising the amino acid sequence of human Protein C (or a fragment of human Protein C).

Determining the degree of homology between sequences may be assessed by any convenient method. However, for determining the degree of homology between sequences, computer programs that make multiple alignments of sequences are useful, for instance Clustal W (Thompson, Higgins, Gibson, *Nucleic Acids Res.*, 22:4673-4680, 1994). If desired, the Clustal W algorithm can be used together with BLOSUM 62 scoring matrix (Henikoff and Henikoff, *Proc. Natl. Acad. Sci. USA*, 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.*, 48:443, 1970) as revised by Smith and Waterman (Smith and Waterman, *Adv. Appl. Math.*, 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.*, 48:1073, 1988) and those described in Computational Molecular Biology, Lesk, ed. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS*, 4:11-17, 1988), FASTA (Pearson and Lipman, *Proc. Natl. Acad. Sci. USA*, 85:2444-2448, 1988; Pearson, Methods in Enzymology, 183:63-98, 1990) and gapped BLAST (Altschul et al., *Nucleic Acids Res.*, 25:3389-3402, 1997), BLASTP, BLASTN, or GCG (Devereux, Haeberli, Smithies, *Nucleic Acids Res.*, 12:387, 1984) are also useful for this purpose. Furthermore, the Dali server at the European Bioinformatics institute offers structure-based alignments of protein sequences (Holm, *Trends in Biochemical Sciences*, 20:478-480, 1995; Holm, *J. Mol. Biol.*, 233:123-38, 1993; Holm, *Nucleic Acid Res.*, 26:316-9, 1998).

By way of providing a reference point, sequences according to the present invention having at least 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

In accordance with the present invention, at least one copy of the endogenous nucleotide sequence encoding Protein C in the genome of the non-human animal has been replaced by a nucleotide sequence encoding human Protein C, encoding a functional fragment of human Protein C or encoding a functional variant of human Protein C.

Typically, non-human animals of the present invention are diploid animals, meaning that their somatic cells contain two homologous copies (or homologues) of each chromosome. In normal (unmodified or wildtype) diploid animals, one endogenous copy of the Protein C gene is found on each of the two chromosomes in the relevant chromosome pair. For example, in normal (wildtype) mice, the Protein C gene is encoded on chromosome 18, so in normal mouse somatic cells there will be two copies of the mouse Protein C gene, one on each chromosome 18.

In some embodiments, one copy of the endogenous nucleotide sequence encoding Protein C in the genome of the non-human animal has been replaced by a nucleotide sequence encoding human Protein C, encoding a functional fragment of human Protein C or encoding a functional variant of human Protein C. Thus, in some embodiments, the genetically modified non-human animal is heterozygous for a human Protein C allele in accordance with the invention. Such heterozygotes may be conveniently referred to as being hproC+/−.

In preferred embodiments, both (i.e. two) copies of the endogenous nucleotide sequence encoding Protein C in the genome of the non-human animal have been replaced by a nucleotide sequence encoding human Protein C, encoding a functional fragment of human Protein C or encoding a functional variant of human Protein C. Thus, in preferred embodiments, the genetically modified non-human animal is homozygous for a human Protein C allele in accordance with the invention. Such homozygotes may be conveniently referred to as being hproC+/+. For the avoidance of doubt, such homozygote animals do not comprise in their genome a nucleotide sequence encoding Protein C that is wildtype (or native) for that animal.

In a particularly preferred embodiment, the invention provides a genetically modified mouse, in which both copies of the endogenous nucleotide sequence encoding Protein C in the genome of said mouse have been replaced by a nucleotide sequence encoding human Protein C.

References herein to "a human Protein C allele" or to a "human Protein C allele in accordance with the invention" are used as shorthand for an allele in which an endogenous nucleotide sequence encoding Protein C in the genome of the non-human animal has been replaced by a nucleotide sequence encoding human Protein C, encoding a functional fragment of human Protein C or encoding a functional variant of human Protein C.

References herein to "at least one copy" or "at least one allele" (or similar) typically means one or two copies or one or two alleles, preferably two copies or two alleles (or both copies or both alleles).

Nucleotide sequences encoding Protein C as discussed herein are of course nucleotide sequences in nucleic acid molecules. Thus, they may be considered nucleic acid molecules (typically DNA molecules) comprising (or consisting of) a described nucleotide sequence.

References herein to the "genome" of a genetically modified non-human animal are typically references to the genome of somatic cells (or diploid cells) of a non-human animal of the invention. Of course, a human Protein C allele in accordance with the invention may also be present in the genome (haploid genome) of some, or all (or substantially all), germ cells (eggs or sperm) of a genetically modified animal of the invention.

"Replaced by" in the context of the present invention means that an endogenous (or wildtype or native) Protein C allele in the genome of the non-human animal has been modified such that rather than comprising (and thus encoding) an endogenous nucleotide sequence encoding endogenous Protein C, the allele instead comprises a nucleotide sequence encoding human Protein C (or a functional fragment or functional variant thereof). Thus, an endogenous nucleotide sequence encoding endogenous Protein C has been removed and a nucleotide sequence encoding human Protein C (or a functional fragment or functional variant thereof) is present in its place. Preferably both Protein C alleles have been so modified.

In preferred embodiments, the start codon (e.g. ATG) of the nucleotide sequence encoding human Protein C (or a functional fragment or functional variant thereof) is positioned (or located or inserted) in the Protein C gene in the genome of the non-human animal at the position corresponding to the start codon of the nucleotide sequence encoding endogenous Protein C and the stop codon (e.g. TAG) of the nucleotide sequence encoding human Protein C (or a functional fragment or functional variant thereof) is positioned (or located or inserted) in the Protein C gene in the genome of the non-human animal at the position corresponding to the stop codon of the nucleotide sequence encoding endogenous Protein C.

In some preferred genetically modified mice of the invention, the start codon (e.g. ATG) of the nucleotide sequence encoding human Protein C (or a functional fragment or functional variant thereof) is positioned (or located or inserted) in the Protein C gene of the mouse at the position corresponding to the start codon (ATG) in exon 2 of the mouse Protein C gene, and the stop codon (e.g. TAG) of the nucleotide sequence encoding human Protein C (or a functional fragment or functional variant thereof) is positioned (or located or inserted) in the Protein C gene in the mouse at the position corresponding to the stop codon (TAG) in exon 9 of the mouse Protein C gene.

The start codon (ATG) in exon 2 of the mouse Protein C gene (endogenous or wildtype mouse Protein C gene) is positioned immediately following (i.e. immediately 3' to or immediately downstream of) the 5'-UTR (untranslated region) portion of exon 2. The stop codon (TAG) in exon 9 of the mouse Protein C gene (endogenous or wildtype mouse Protein C gene) is positioned immediately in front of (i.e. immediately 5' to or immediately upstream of) the 3'-UTR (untranslated region) portion of exon 9.

Thus, in some preferred embodiments of a genetically modified mouse of the invention, the start codon (e.g. ATG) of the nucleotide sequence encoding human Protein C (or a functional fragment or functional variant thereof) is positioned (or located or inserted) in the mouse genome immediately following (i.e. immediately 3' to or immediately downstream of) the 5'-UTR (untranslated region) portion of exon 2, and the stop codon (e.g. TAG) of the nucleotide sequence encoding human Protein C (or a functional fragment or functional variant thereof) is positioned (or located or inserted) in the mouse genome immediately in front of (i.e. immediately 5' to or immediately upstream of) the 3'-UTR (untranslated region) portion of exon 9. A nucleotide sequence of the 5'-UTR (untranslated region) portion of exon 2 of the mouse Protein C gene is set forth herein as SEQ ID NO:5. A nucleotide sequence of the 3'-UTR (untranslated region) portion of exon 9 of the mouse Protein C gene is set forth herein as SEQ ID NO:6.

Alternatively viewed, an endogenous nucleotide sequence encoding endogenous Protein C in the genome of a non-human animal (e.g. mouse) has been substituted with a nucleotide sequence encoding human Protein C (or a functional fragment or a functional variant thereof). Preferably, both Protein C alleles have been so substituted.

Alternatively viewed, the non-human animal of the invention (e.g. mouse) contains a targeted insertion of a nucleotide sequence encoding human Protein C (or a functional fragment or a functional variant thereof) into at least one copy of the Protein C gene in the animal, wherein, as a result of the targeted insertion, said at least one copy of the Protein C gene comprises (and is capable of expressing) a nucleotide sequence encoding human Protein C (or a functional fragment or functional variant thereof) and does not comprise (and thus is not capable of expressing) an endogenous (or wildtype or native) nucleotide sequence encoding endogenous Protein C. Preferably, both copies of the Protein C gene in the genome of the non-human animal have the targeted insertion.

Alternatively viewed, the non-human animal of the invention (e.g. mouse) is characterised by a targeted replacement of a nucleotide sequence encoding endogenous Protein C in the genome of said non-human animal by a nucleotide sequence encoding human Protein C (or a functional fragment or a functional variant thereof). Preferably, the non-human animal of the invention comprises such a targeted replacement in both Protein C alleles in its genome.

Such a modified allele may be referred to as a "knock-in" allele (or KI allele). In this regard, a nucleotide sequence encoding human Protein C (or encoding a functional fragment or functional variant thereof) is "knocked-in" to at least one Protein C allele in the genome a non-human animal. Such a "knock-in" results in the removal of the endogenous nucleotide sequence encoding endogenous Protein C. Thus, the modified (knock-in) allele has the endogenous nucleotide sequence encoding endogenous Protein C knocked-out. Accordingly, an endogenous nucleotide sequence encoding endogenous Protein C is replaced by a nucleotide sequence encoding human Protein C (or functional fragment functional variant thereof). In preferred embodiments, a "knock-in" allele in accordance with the invention is a constitutive knock-in allele.

Determining whether or not at least one copy (e.g. one copy or two copies) of the endogenous nucleotide sequence encoding Protein C in the genome of a non-human animal has been replaced by a nucleotide sequence encoding human Protein C (or a functional fragment or a functional variant thereof) in a given non-human animal can be done by any appropriate means and suitable methods are well-known to a skilled person. For example, genotyping could be used, e.g. a PCR-based genotyping method and/or Southern blotting could be used. Suitable methods are described in the Example section herein.

In some embodiments, the non-human animals of the invention are produced using a method that employs a vector of the invention.

Thus, in some embodiments, a non-human animal in accordance with the invention comprises in its genome at least one allele of the Protein C gene that comprises (i) a 5' untranslated region (UTR) nucleotide sequence of the non-human animal Protein C gene, (ii) a nucleotide sequence encoding human Protein C (or a functional fragment or functional variant thereof) and (iii) a 3' untranslated region (UTR) nucleotide sequence of the non-human animal Protein C gene. Elements (i), (ii) and (iii) are typically positioned immediately after each other in this order (i.e. (i) followed immediately by (ii) followed immediately by (iii)), in the 5' to 3' direction. In some embodiments, a marker for positive selection may be positioned 5' with respect to the 5'-UTR or be positioned 3' with respect to the 3' UTR. The marker for positive selection may be flanked by site-specific recombination sites (e.g. LoxP sites). In some embodiments, the marker for positive selection may have been removed (e.g. by a site-specific recombinase enzyme such as Cre recombinase). In embodiments in which the marker for positive selection has been removed by a site-specific recombinase enzyme (such as Cre), the nucleotide sequence of a single site-specific recombination site is typically retained in the allele.

In some embodiments, a non-human animal in accordance with the invention is a mouse that comprises in its genome at least one allele of Protein C gene that comprises (i) a 5' untranslated region (UTR) nucleotide sequence of exon 2 of the mouse Protein C gene (e.g. SEQ ID NO:5), (ii) a nucleotide sequence encoding human Protein C and (iii) a 3' untranslated region (UTR) nucleotide sequence of exon 9 of the mouse Protein C gene (e.g. SEQ ID NO:6). Elements (i), (ii) and (iii) are typically positioned immediately after each other in this order (i.e. (i) followed immediately by (ii) followed immediately by (iii)), in the 5' to 3' direction. In some embodiments, a marker for positive selection (e.g. Neo') may be positioned 5' with respect to the 5'-UTR or be positioned 3' with respect to the 3' UTR, preferably positioned 3' with respect to the 3' UTR. The marker for positive selection may be flanked by site-specific recombination sites (e.g. LoxP sites). A preferred such allele is substantially as depicted in FIG. 1C herein. In some embodiments, the non-human animal in accordance with the invention is a mouse that comprises in its genome at least one allele of the Protein C gene that comprises a nucleotide sequence of SEQ ID NO:9. In some preferred embodiments, the marker for positive selection has been removed (e.g. by a site-specific recombinase enzyme such as Cre recombinase). Thus, in some embodiments, the non-human animal in accordance with the invention is a mouse that comprises in its genome at least one allele of the Protein C gene that comprises a nucleotide sequence of SEQ ID NO:9, with the proviso that the neomycin resistance gene (Ned) (which is found within SEQ ID NO:9) has been removed. In embodiments in which the marker for positive selection has been removed by a site-specific recombinase enzyme (such as Cre) the nucleotide sequence of a single site-specific recombination site is typically retained in the allele. A preferred such allele is substantially as depicted in FIG. 1D herein.

In preferred embodiments, the only substantive modification to a Protein C allele (or protein C gene) in the non-human animal (i.e. modification as compared to the wildtype Protein allele in the relevant non-human animal) is the replacement of (or substitution of) an endogenous nucleotide sequence encoding Protein C by a nucleotide sequence encoding human Protein C (or functional fragment or functional variant thereof). The presence of a marker for positive selection marker and/or one or more site-specific recombination sites would not be typically considered substantive modifications.

Thus, in preferred embodiments, human Protein C alleles in accordance with the invention comprise sequences upstream (5'- to) and downstream (3'-) to the nucleotide sequence encoding human Protein C (or functional fragment or functional variant thereof) that are wildtype (or native or endogenous) for the relevant non-human animal. Such sequences may include regulatory sequences, such as promoters and/or enhancers, etc. Thus, in preferred embodiments, expression of the nucleotide sequence encoding human Protein C (or functional fragment or functional variant thereof) is under the control of the endogenous regulatory sequences of the Protein C gene of the relevant non-human animal.

In some alternative embodiments, a human Protein C allele in accordance with the invention may additionally comprise one or more regulatory sequences (e.g. promoters and/or enhancers) of the human Protein C gene (e.g. to replace one or more regulatory sequences of the non-human animal).

In some embodiments, a genetically modified non-human animal of the invention further comprises one or more additional genetic modifications in its genome (i.e. additional to the replacement of an endogenous nucleotide sequence encoding Protein C by a nucleotide sequence encoding human Protein C or fragment or variant thereof). The skilled person is familiar with methods for making such genetic modifications, e.g. gene knock-outs.

In some such embodiments, the further genetic modification is a modification that down-regulates or inactivates (or renders the animal deficient in or devoid of) of one or more other (i.e. non-Protein C) genes. For example, the further genetic modification may be a knock-out of one or more other genes.

In some embodiments, the other gene is a gene encoding a blood clotting factor (e.g. one or more blood clotting factors may additionally be knocked-out). In some embodiments, the other gene is a gene encoding Factor VIII (e.g. Factor VIII may additionally be knocked-out). In some embodiments, the other gene is a gene encoding Factor IX (e.g. Factor IX may additionally be knocked-out). In some embodiments, there may be further genetic modifications in the genes encoding Factor VIII and Factor IX (e.g. Factor VIII and Factor IX may additionally be knocked-out). In some embodiments, the other gene is a gene encoding Factor X (e.g. Factor X may additionally be knocked-out). In some embodiments, the other gene is a gene encoding Factor XI (e.g. Factor XI may additionally be knocked-out).

In some embodiments, a non-human animal of the invention is an experimental non-human animal model (e.g. mouse model). Such experimental animal models are typically suitable for studying human Protein C in vivo. In particular, such experimental animal models are typically suitable for testing agents (e.g. candidate therapeutic agents) to identify the potential for the use of such agents in therapy (e.g. human therapy), In some embodiments, the therapy (or potential therapy) is therapy (or potential therapy) of a disease or condition associated with Protein C or APC (or the Protein C or APC pathway), e.g. as discussed elsewhere herein.

Non-human animals at each stage of development, e.g. embryonic, juvenile, or adult, are encompassed by the present invention. In some embodiments, the non-human animals are adult animals. In the case of mice, in some embodiments the mice are at least six weeks of age, preferably at least 8 weeks of age (e.g. 8-10 weeks of age).

Alternatively viewed, or in another aspect, the present invention provides a genetically modified non-human animal (e.g. a mouse) comprising in its genome at least one nucleic acid molecule encoding human Protein C (or a functional fragment or functional variant thereof), wherein said nucleic acid molecule is located in (and capable of being expressed from) the Protein C gene of the genetically modified non-human animal. Preferably, said at least one nucleic acid molecule is operably linked in the genome of the non-human animal to one or more of the regulatory elements (e.g. promoters and/or enhancers) of the Protein C gene in the non-human animal (endogenous regulatory elements). Embodiments of other aspects of the invention described herein apply, mutatis mutandis, to this aspect of the invention.

Alternatively viewed, or in another aspect, the present invention provides a genetically modified non-human animal (e.g. mouse) having a modified Protein C gene locus, said modified Protein C locus being characterised by the presence of a nucleotide sequence encoding human Protein C (or a functional fragment or a functional variant thereof) and the absence of a nucleotide sequence encoding Protein C that is endogenous to the non-human animal. Embodiments of other aspects of the invention described herein apply, mutatis mutandis, to this aspect of the invention.

Further alternatively viewed, or in another aspect, the present invention provides a knock-in non-human animal (e.g. mouse), wherein a nucleic acid molecule comprising a nucleotide sequence encoding human Protein C (or a functional fragment or a functional variant thereof) is knocked-in to one or more copies of the Protein C gene in the genome of the non-human animal. Embodiments of other aspects of the invention described herein apply, mutatis mutandis, to this aspect of the invention.

Further alternatively viewed, or in another aspect, the present invention provides a humanized non-human animal (e.g. mouse) comprising in its genome at least one humanized Protein C allele, said humanized Protein C allele being characterized in that the endogenous nucleotide sequence encoding endogenous Protein C has been replaced by a nucleotide sequence encoding human Protein C (or a functional fragment or a functional variant thereof). Embodiments of other aspects of the invention described herein apply, mutatis mutandis, to this aspect of the invention.

Further alternatively viewed, or in another aspect, the present invention provides a transgenic non-human animal (e.g. mouse), in which at least one copy of the endogenous nucleotide sequence encoding Protein C in the genome of said non-human animal has been replaced by a nucleotide sequence encoding human Protein C (or a functional fragment or a functional variant thereof). Embodiments of other aspects of the invention described herein apply, mutatis mutandis, to this aspect of the invention.

Further alternatively viewed, or in another aspect, the present invention provides a genetically modified non-human animal (e.g. mouse), comprising in its genome a nucleotide sequence that encodes human Protein C (or a fragment or variant thereof), wherein said nucleotide sequence is operably linked to an endogenous Protein C regulatory sequence (e.g. promoter) at the non-human animal Protein C locus. Embodiments of other aspects of the invention described herein apply, mutatis mutandis, to this aspect of the invention.

Further alternatively viewed, or in another aspect, the present invention provides a genetically modified non-human animal (e.g. mouse) carrying (or comprising) a heritable exchange in a nucleotide sequence, said exchange being the replacement of (or exchange of or substitution of) an endogenous nucleotide sequence encoding Protein C in the genome of said non-human animal by a nucleotide sequence encoding human Protein C (or a functional fragment or a functional variant thereof). In accordance with the discussion elsewhere herein, said heritable exchange is established by technical means. Embodiments of other aspects of the invention described herein apply, mutatis mutandis, to this aspect of the invention.

In another aspect, the present invention provides a genetically modified non-human animal (e.g. a mouse), wherein said animal comprises in its genome (e.g. stably integrated into its genome), and is capable of expressing, one or more (e.g. one or two) copies of a nucleotide sequence encoding human Protein C (or a functional fragment or functional variant thereof). Preferably, such animals do not encode (and thus are not capable of expressing) endogenous Protein C. Embodiments of other aspects of the invention described herein apply, mutatis mutandis, to this aspect of the invention. For example, said nucleotide sequence may be positioned in the Protein C gene of the non-human animal (e.g. to replace a nucleotide sequence encoding endogenous Protein C in the non-human animal), for example as described elsewhere herein.

In another aspect, the present invention provides a genetically modified non-human animal (e.g. a mouse), wherein said animal expresses (or is capable of expressing) human Protein C (or a functional fragment or functional variant thereof) and does not express (or is not capable of expressing) endogenous Protein C (i.e. does not express (or is not capable of expressing) Protein C that is wildtype or native to the non-human animal species). Embodiments of other aspects of the invention described herein apply, mutatis mutandis, to this aspect of the invention.

Typically, a non-human animal of the invention is fertile and capable of transmitting a human Protein C allele in accordance with the invention to its offspring.

Thus, in one aspect, the present invention provides offspring or descendants of a non-human animal of the invention, wherein said offspring or descendants comprise in their genome at least one (preferably two) human Protein C allele(s) in accordance with the invention. Embodiments of other aspects of the invention described herein apply, mutatis mutandis, to this aspect of the invention.

In another aspect, the present invention provides a cell or cell line derived from a genetically-modified non-human animal of the invention, wherein said cell or cell line comprises in its genome at least one (preferably two) human Protein C allele(s) in accordance with the invention. The cell may be a somatic cell or a germ cell. In some embodiments, the cell or cell line is a pluripotent stem cell or cell line (e.g. an embryonic stem cell or cell line derived from an embryonic non-human animal of the invention or an induced pluripotent stem cell (iPSC)), or a cell line derived from a somatic cell of a non-human animal of the invention. Embodiments of other aspects of the invention described herein apply, mutatis mutandis, to this aspect of the invention.

In another aspect, the present invention provides a tissue or organ derived from a genetically-modified non-human animal of the invention, wherein said tissue or organ comprises in the genome of the cells thereof at least one (preferably two) human Protein C allele(s) in accordance with the invention. Embodiments of other aspects of the invention described herein apply, mutatis mutandis, to this aspect of the invention.

In another aspect, the present invention provides a cell-containing sample derived from a genetically-modified non-human animal of the invention, wherein said sample comprises in the genome of the cells thereof at least one (preferably two) human Protein C allele(s) in accordance with the invention. Embodiments of other aspects of the invention described herein apply, mutatis mutandis, to this aspect of the invention.

In another aspect, the present invention provides a non-human (e.g. mouse) pluripotent stem cell in which at least one copy of the endogenous nucleotide sequence encoding Protein C in the genome of said non-human pluripotent cell has been replaced by a nucleotide sequence encoding human Protein C, encoding a functional fragment of human Protein C or encoding a functional variant of human Protein C. Embodiments of other aspects of the invention described herein apply, mutatis mutandis, to this aspect of the invention. The non-human pluripotent stem cell may be, for example, an embryonic stem (ES) cell or an induced pluripotent stem cell (iPSC). Embryonic stem (ES) cells are preferred. Preferably, the non-human pluripotent stem cell is a mouse pluripotent stem cell, such as a mouse embryonic stem (ES) cell or a mouse induced pluripotent stem cell (iPSC). Mouse embryonic stem (ES) cells are particularly preferred (for example C57BL/6 ES cells).

In another aspect, the present invention also provides a vector for homologous recombination in a non-human pluripotent stem cell (e.g an isolated non-human pluripotent stem cell), wherein said vector is capable of replacing (or conferring the replacement of or mediating the replacement of) at least one copy of the endogenous nucleotide sequence encoding Protein C in the genome of said non-human pluripotent stem cell with a nucleotide sequence encoding human Protein C (or a functional fragment or functional variant thereof).

A vector of the invention may also be considered a targeting vector (or a gene targeting vector), a recombinant vector or a recombinant targeting vector. The vector is a nucleic acid molecule, preferably a DNA molecule.

Preferably, the non-human pluripotent stem cells are of a species of non-human animal described elsewhere herein. In some embodiments, the non-human pluripotent stem cells are non-human embryonic stem (ES) cells. Preferably, the non-human pluripotent stem cells are mouse pluripotent stem cells. Particularly preferably, the non-human pluripotent stem cells are mouse embryonic stem (ES) cells. In some embodiments, the mouse embryonic stem (ES) cells are C57BL/6 ES cells.

In one aspect, and in some embodiments, the invention provides a vector comprising, in functional combination, (i) a nucleotide sequence encoding human Protein C, encoding a functional fragment of human Protein C or encoding a functional variant of human Protein C (preferably a nucleotide sequence encoding human Protein C); (ii) at least one marker for positive selection (e.g. an antibiotic resistance gene such as the neomycin resistance gene, Neo'); (iii) a 5'-homology arm; and (iv) a 3'-homology arm.

In some embodiments, the marker for positive selection is flanked by site-specific recombination sites (e.g. loxP sites) that can be recognised by a recombinase enzyme (e.g. Cre recombinase).

In some embodiments, the marker for positive selection (and its flanking site-specific recombination sites where present) is positioned within one of the homology arms. Put another way, in some embodiments one of the homology arms in the vector is interrupted by the marker for positive selection (and its flanking site-specific recombination sites where present). Thus, in some embodiments, one of the homology arms (e.g. the 3'-homology arm) comprises two distinct parts (or sub-parts) with the marker for positive selection (and its flanking site-specific recombination sites where present) being located between said two parts.

In some embodiments, at least one marker for negative selection is additionally present in the vector (e.g. a gene encoding a toxin such as diptheria toxin A, DTA, or a gene encoding thymidine kinase).

In a preferred embodiment, the vector of invention comprises, in order from 5' to 3', (i) a 5'-homology arm, (ii) a nucleotide sequence encoding human Protein C, encoding a functional fragment of human Protein C or encoding a functional variant of human Protein C (preferably a nucleotide sequence encoding human Protein C); (iii) a 3'-homology arm and (iv) a marker for positive selection (optionally flanked by site-specific recombination sites where present), wherein the marker for positive selection (and its flanking site-specific recombination sites where present) is positioned within the 3' homology arm. In some such embodiments, a marker for negative selection is additionally present in the vector and is positioned 5' with respect to the 5-homology arm (i.e. it is positioned 5' of the 5' end of the 5-homology arm).

A homology arm (a 5'- or 3'-homology arm) is a portion (or fragment or segment) of DNA having a nucleotide sequence that corresponds to (or corresponds essentially to) a nucleotide sequence in the genome of the relevant (or corresponding) non-human animal cell to be targeted. Alternatively viewed, a homology arm is a polynucleotide having a nucleotide sequence that corresponds to (or corresponds essentially to) a nucleotide sequence in the genome of the relevant (or corresponding) non-human cell to be targeted. In some embodiments, a homology arm is a portion of DNA having a nucleotide sequence that corresponds to or corresponds essentially to (e.g. has at least 90%, or at least 95%, or at least 99%, preferably 100% identity to) a nucleotide sequence in the genome of the relevant (or corresponding) non-human cell to be targeted.

Homology arms are of sufficient length to be able to confer (or mediate) homologous recombination between the vector and the corresponding nucleotide sequence (or target cognate chromosomal region) in the genome of the non-human animal cell to be targeted. Each homology arm is typically at least 500 base pairs in length, preferably at least 1,000, at least 2,000, at least 3,000, at least 4,000, at least 5,000, at least 6,000, at least 7,000, at least 8,000, at least 9,000 or at least 10,000 base pairs in length (e.g. 1,000 to 10,000 base pairs in length). The 5'-homology arm and the 3'-homology arm are not necessarily the same length.

After introduction into the non-human animal cell, the homology arms can undergo homologous recombination with the corresponding (or target) genomic DNA sequences in the non-human cell to achieve genetic modification (or targeting) of the chromosomal locus. In accordance with the present invention, the chromosomal locus is the Protein C gene and the genetic modification is the replacement of an endogenous nucleotide sequence encoding Protein C in the genome of the non-human cell with a nucleotide sequence encoding human Protein C (or encoding a functional fragment of human Protein C or encoding a functional variant of human Protein C).

Thus, homology arms in accordance with the present invention typically comprise (or consist of) nucleotide sequences that can undergo homologous recombination with corresponding genomic nucleotide sequences of the endogenous Protein C gene (or Protein C locus) in a non-human pluripotent stem cell to achieve targeted replacement of an endogenous nucleotide sequence encoding endogenous Protein C in the genome of the non-human pluripotent stem cell with a nucleotide sequence encoding human Protein C (or a functional fragment or functional variant thereof).

A 5'-homology arm comprises (or consists of or consists essentially of) a nucleotide sequence that corresponds to or corresponds essentially to (e.g. has at least 90%, or at least 95%, or at least 99%, preferably 100% identity to) a genomic sequence in the non-human animal that is positioned 5' with respect to the endogenous nucleotide sequence encoding Protein C. Thus, typically, a 5'-homology arm is, after introduction of the vector into a non-human animal cell, capable of undergoing (or capable of mediating) homologous recombination with the corresponding (or target) genomic DNA sequence in the genome of the non-human animal that is positioned 5' to nucleotide sequence encoding Protein C.

A 3'-homology arm comprises (or consists of or consists essentially of) a nucleotide sequence that corresponds to or corresponds essentially to (e.g. has at least 90%, or at least 95%, or at least 99%, preferably 100% identity to) a genomic sequence in the non-human animal that is positioned 3' with respect to the endogenous nucleotide sequence encoding Protein C. Thus, typically, a 3'-homology arm is, after introduction of the vector into the non-human animal cell, capable of undergoing (or capable of mediating) homologous recombination with the corresponding (or target) genomic DNA sequence in the genome of the non-human animal that is positioned 3' to the nucleotide sequence encoding Protein C.

The skilled person in this field is familiar with homology arms and would be readily able to identify and select appropriate homology arms for inclusion in vectors of the invention. For example, genomic fragments containing homology arms could be amplified (e.g. using a high fidelity Taq DNA polymerase) from a BAC (bacterial artificial chromosome) clone containing the desired genomic sequence of the relevant non-human animal. BAC clones and libraries are commercially available.

In some embodiments, the 5'-homology arm of a vector of the invention comprises (or consists of) a nucleotide sequence of SEQ ID NO:2, or a sequence substantially homologous thereto (e.g. a sequence having at least 90%, at least 95 or at least 99% sequence identity to SEQ ID NO:2). A 5'-homology arm consisting of a nucleotide sequence of SEQ ID NO:2 is preferred.

In some embodiments, the 3'-homology arm of a vector of the invention comprises a nucleotide sequence of SEQ ID NO:3 and/or a nucleotide sequence of SEQ ID NO:4, or a sequence substantially homologous to SEQ ID NO:3 and/or substantially homologous to SEQ ID NO:4 (e.g. a sequence having at least 90%, at least 95 or at least 99% sequence identity to SEQ ID NO:3 and/or substantially homologous to SEQ ID NO:4). In some embodiments, the 3'-homology arm of a vector of the invention comprises a nucleotide sequence of SEQ ID NO:3 and a nucleotide sequence of SEQ ID NO:4, or a sequence substantially homologous to SEQ ID NO:3 and/or SEQ ID NO:4. In some embodiments, a 3'-homology arm comprising a nucleotide sequence of SEQ ID NO:3 and SEQ ID NO:4 is preferred.

In some embodiments, the 3'-homology arm comprises a nucleotide sequence of SEQ ID NO:3 (or substantially homologous sequence) and a nucleotide sequence of SEQ ID NO:4 (or substantially homologous sequence), wherein the nucleotide sequences of SEQ ID NO:3 (or substantially homologous sequence) and SEQ ID NO:4 (or substantially homologous sequence) are separated by a nucleotide sequence encoding a marker for positive selection (which is optionally flanked by site-specific recombination sites).

As indicated above, the vector comprises a nucleotide sequence encoding human Protein C, encoding a functional fragment of human Protein C or encoding a functional variant of human Protein C. Preferably, the vector comprises a nucleotide sequence encoding human Protein C. The amino acid sequence of human Protein C is set forth herein as SEQ ID NO:11. Thus, preferably, the vector comprises a nucleotide sequence encoding SEQ ID NO:11. A preferred nucleotide sequence encoding human Protein C (SEQ ID NO:11) is SEQ IS NO:8.

As indicated above, vectors of the invention may comprise a marker for positive selection. A marker for positive selection is typically a nucleotide sequence encoding a protein that confers antibiotic resistance upon a cell in which it is expressed. The positive selection marker enables the selection (or identification) of cells into which the vector has been transfected and which are expressing the vector. The marker for positive selection is typically an antibiotic resistance gene. The neomycin resistance gene (Ned, Neo cassette) is a preferred positive selection marker. The neomycin resistance gene is a well-known and well characterised marker for positive selection that is routinely used in the field. Expression of the neomycin resistance gene can be selected for with the antibiotic G418.

As indicated above, in some embodiments of vectors of the invention the marker for positive selection is flanked by, typically identical, site-specific recombination sites which are recognisable by a site-specific recombinase enzyme (i.e. two, typically identical, site-specific recombination sites may be present, one positioned 5' to the marker for positive selection and one positioned 3' to the marker for positive selection). Preferably, the site-specific recombination sites are loxP sites. A loxP site nucleotide sequence is set forth herein as SEQ ID NO:7. When exposed to an appropriate site-specific recombinase enzyme, e.g. Cre recombinase in the case of LoxP sites, the recombinase can recognise recombining site-specific recombination sites and mediate the deletion of the nucleotide sequence that is located between the two site-specific recombination sites, e.g. in this case the marker for positive selection.

In some embodiments, the vector of the invention comprises, in order from 5' to 3', (i) a 5'-homology arm, (ii) a nucleotide sequence encoding human Protein C, encoding a functional fragment of human Protein C or encoding a functional variant of human Protein C (preferably a nucleotide sequence encoding human Protein C); (iii) a first part of a 3'-homology arm; (iv) a first site-specific recombination site; (v) a marker for positive selection; (vi) a second site-specific recombination site and (vii) a second part of a 3'-homology arm. Preferably, elements (i)-(vii) are as described elsewhere herein).

Thus, in preferred embodiments, the vector of the invention comprises, in order from 5' to 3', (i) a 5'-homology arm comprising (or consisting of) a nucleotide sequence of SEQ ID NO:2; (ii) a nucleotide sequence encoding human Protein C; (iii) a first part of a 3'-homology arm said first part comprising (or consisting of) a nucleotide sequence of SEQ ID NO:3; (iv) a first loxP recombination site comprising (or consisting of) a nucleotide sequence of SEQ ID NO:7; (v) a marker for positive selection that is the neomycin resistance gene (Ned); (vi) a second loxP recombination site comprising (or consisting of) a nucleotide sequence of SEQ ID NO:7; and (vii) a second part of a 3'-homology arm said second part comprising (or consisting of) a nucleotide sequence of SEQ ID NO:4.

In one preferred embodiment, the vector comprises a nucleotide sequence of SEQ ID NO:9. SEQ ID NO:9 is a nucleotide sequence present in the vector used in the Example section herein to generate targeted mouse embryonic stem ES cells in accordance with the invention, which in turn were used to generate genetically modified mice in accordance with the invention. SEQ ID NO:9 includes the 5'-homology arm, the nucleotide sequence encoding human Protein C, the first part of the 3'-homology arm, the loxP flanked neomycin resistance gene (Ned), and the second part of the 3'-homology arm.

As indicated above, in some embodiments a negative selection marker is additionally present in the vector. A negative selection marker is a nucleotide sequence (or gene) which, when expressed in cells, encodes a protein that leads to cell death (or is toxic to the cells). The nucleotide sequence (or gene) encoding the negative selection marker is located in the vector outside of the homology arms, i.e. located either 5' with respect to the 5'-homology arm or 3'- with respect to the 3'-homology arm.

In some embodiments, the negative selection marker is a nucleotide sequence encoding a toxin such as diptheria toxin A (DTA) or a nucleotide sequence encoding thymidine kinase (preferably a nucleotide sequence encoding DTA). During homologous recombination, nucleotide sequences outside of the homology arms are typically lost, but if the vector is randomly integrated (non-homologously recombined) into the genome the negative selection marker is typically retained and expressed. In such a case (unlike if the correct homologous recombination event has occurred), the negative selection marker is typically transcribed and translated which creates a selective disadvantage for clones with non-homologous (random) integration. The negative selection marker DTA is toxic to cells by inhibiting protein synthesis and thus cells expressing DTA are typically eliminated. The negative selection marker thymidine kinase (TK) renders cells in which it expressed sensitive to thymidine analogues. Thus, cells expressing TK can be eliminated (or selected against) by culturing the cells in the presence of a thymidine analogue.

In a some embodiments, a vector of the invention comprises, in order from 5' to 3', (i) a marker for negative selection; (ii) a 5'-homology arm, (iii) a nucleotide sequence encoding human Protein C, encoding a functional fragment of human Protein C or encoding a functional variant of human Protein C (preferably a nucleotide sequence encoding human Protein C); (iv) a first part of a 3'-homology arm, (v) a first site-specific recombination site, (vi) a marker for positive selection, (vii) a second site-specific recombination site and (viii) a second part of a 3'-homology arm. Preferably, elements (i)-(viii) are as described elsewhere herein.

Thus, in preferred embodiments, a vector of the invention comprises, in order from 5' to 3', (i) a marker for negative selection; (ii) a 5'-homology arm comprising (or consisting of) a nucleotide sequence of SEQ ID NO:2; (iii) a nucleotide sequence encoding human Protein C; (iv) a first part of a 3'-homology arm said first part comprising (or consisting of) a nucleotide sequence of SEQ ID NO:3, (v) a first loxP recombination site comprising (or consisting of) a nucleotide sequence of SEQ ID NO:7; (vi) a marker for positive selection that is the neomycin resistance gene (Ned); (vii) a second loxP recombination site comprising (or consisting of) a nucleotide sequence of SEQ ID NO:7; and (viii) a second part of a 3'-homology arm said second part comprising (or consisting of) a nucleotide sequence of SEQ ID NO:4.

In one embodiment, the vector comprises a nucleotide sequence of SEQ ID NO:9 and, located either 5' thereto or 3' thereto (preferably located 5' thereto), a marker for negative selection (e.g. as described herein).

In addition to the components of the vector described above that are important for targeting (i.e. generating a "knock-in" allele), the vector also typically comprises a vector backbone nucleotide sequence. The substantive components of the vector can be readily assembled and cloned into a vector backbone using routine methods in the art (as for example described in Green and Sambrook., 2012, Molecular Cloning: A Laboratory Manual, 4th Ed., Cold Spring Harbor Press, Cold Spring Harbor, N.Y. and other laboratory textbooks). Methods for preparing vectors for gene targeting are well-known in the art and any suitable method may be used.

In some embodiments, the vector comprises (or consists of) a nucleotide sequence of SEQ ID NO:1, or a sequence substantially homologous thereto. Substantially homologous sequences are described elsewhere herein. Preferably, if the vector has such a substantially homologous sequence, the alteration in nucleotide sequence is outside of the region of the targeting vector that is defined by SEQ ID NO:9. In a preferred embodiment, the vector comprises (or consists of) a nucleotide sequence of SEQ ID NO:1. The vector may be circular or linearized.

Vectors are typically constructed (or assembled) as circular nucleic acid (DNA) molecules and are then linearized before use. Thus, in some embodiments, the vector is a linearized vector. Linearizing is typically done using a restriction enzyme which recognises and cuts at a restriction site that is located outside of the substantive components of the vector (e.g. is located in the vector backbone), e.g. located 5' with respect to the 5'-homology arm and located 3' with respect to the 3'-homology arm. In some embodiments, the vector has been linearized using the restriction enzyme NotI. For example, in some embodiments, a vector of the present invention is a linearized vector produced by linearizing (e.g. with NotI) a circular vector comprising (or consisting of) a nucleotide sequence of SEQ ID NO:1.

The term "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. Deoxyribonucleic acid sequences (DNA) sequences are preferred. The sequences may also contain modified bases. The nucleic acid molecules may be double stranded or single stranded, preferably double stranded. The nucleic acid molecules may be wholly or partially synthetic or recombinant.

The nucleic acid molecules of the invention may be "isolated" or "purified". The term "isolated" or "purified" typically refers to a nucleic acid that is substantially free of cellular material or other nucleic acids from the source from which it is derived or produced.

In another aspect, the present invention provides a non-human pluripotent stem cell that has been transfected with a vector of the invention.

In another aspect, the present invention provides a method for producing (or generating) a non-human pluripotent stem cell in which at least one copy of the endogenous nucleotide sequence encoding Protein C in the genome of said non-human pluripotent stem cell has been replaced by a nucleotide sequence encoding human Protein C, encoding a functional fragment of human Protein C or encoding a functional variant of human Protein C. Embodiments of other aspects of the invention described herein apply, mutatis mutandis, to this aspect of the invention.

In some embodiments, the method for producing (or generating) a non-human pluripotent stem cell comprises the steps of:

(i) transfecting non-human pluripotent stem cells with a vector of the invention; and (ii) selecting one or more transfected non-human pluripotent stem cells of (i) to identify one or more non-human pluripotent stem cell clones in which at least one copy of the endogenous nucleotide sequence encoding Protein C in the genome of said non-human pluripotent stem cell has been replaced by a nucleotide sequence encoding human Protein C, encoding a functional fragment of human Protein C or encoding a functional variant of human Protein C.

Such methods for producing non-human pluripotent stem cells are in vitro methods.

Preferably, the non-human pluripotent stem cells are of a species of non-human animal described elsewhere herein. In some embodiments, the non-human pluripotent stem cells are non-human embryonic stem (ES) cells. Preferably, the non-human pluripotent stem cells are mouse pluripotent stem cells. Particularly preferably, the non-human pluripotent stem cells are mouse embryonic stem (ES) cells. In some embodiments, the mouse embryonic stem (ES) cells are C57BL/6 ES cells.

Step (i) of said method involves transfecting non-human pluripotent stem cells with a vector of the invention. Typically, the vector is linearized (e.g. with NotI) prior to transfection. Transfection may be performed by any suitable means and the skilled person is familiar with appropriate and standard transfection protocols. For example, transfection may be done by electroporation, lipofection, nucleofection, or the like. In some embodiments, electroporation is preferred.

Step (ii) of said method involves selecting one or more transfected non-human pluripotent stem cells of (i) in which at least one copy of the endogenous nucleotide sequence encoding Protein C in the genome of said non-human pluripotent cell has been replaced by a nucleotide sequence encoding human Protein C (or a functional fragment or functional variant thereof). The selecting of step (ii) typically comprises analysing for (or screening for) the presence or absence in the transfected non-human pluripotent stem cells of the desired homologous recombination event (or desired targeting event), i.e. analysing (directly and/or indirectly) for the presence or absence in the genome of the non-human pluripotent stem cell of a Protein C allele that has been correctly targeted with the targeting vector.

Typically, the selecting step of (ii) comprises selecting one or more transfected non-human pluripotent stem cells on the basis of the expression of a marker for positive selection (a marker for positive selection is typically provided by the targeting vector). Preferably, the marker for positive selection is the neomycin resistance gene (Neo) and selection agent is G418 (e.g. 200 μg/ml). Typically, G418 resistant clones are picked and amplified (e.g. in a 96 well plate).

Typically, the selecting step also comprises, in addition to selection on the basis of the expression of a marker for positive selection, the analysis of genomic DNA to determine whether or not the desired homologous recombination event has occurred. This analysis of genomic DNA may be done using a PCR (polymerase chain reaction)-based method and/or by Southern blotting and/or DNA sequencing. Preferably, PCR-based and Southern blotting analysis is done.

Figure 4:
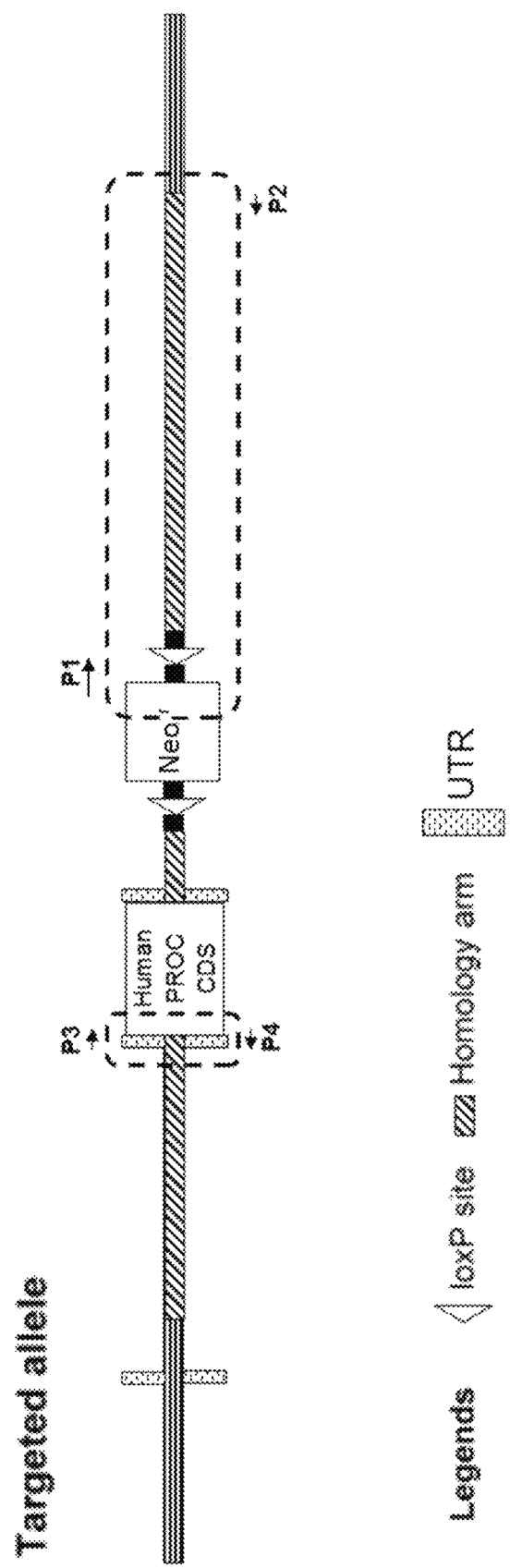

In some embodiments, the PCR-based method comprises performing a PCR reaction in which the template DNA is genomic DNA isolated from the transfected non-human pluripotent stem cells under investigation (i.e. the potentially targeted non-human pluripotent stem cells) and PCR primers are designed such a PCR product of an expected size is produced if the desired homologous recombination event has occurred. An exemplary and preferred PCR-based method is described in the Example section herein (and is depicted in FIG. 4).

Figure 7:
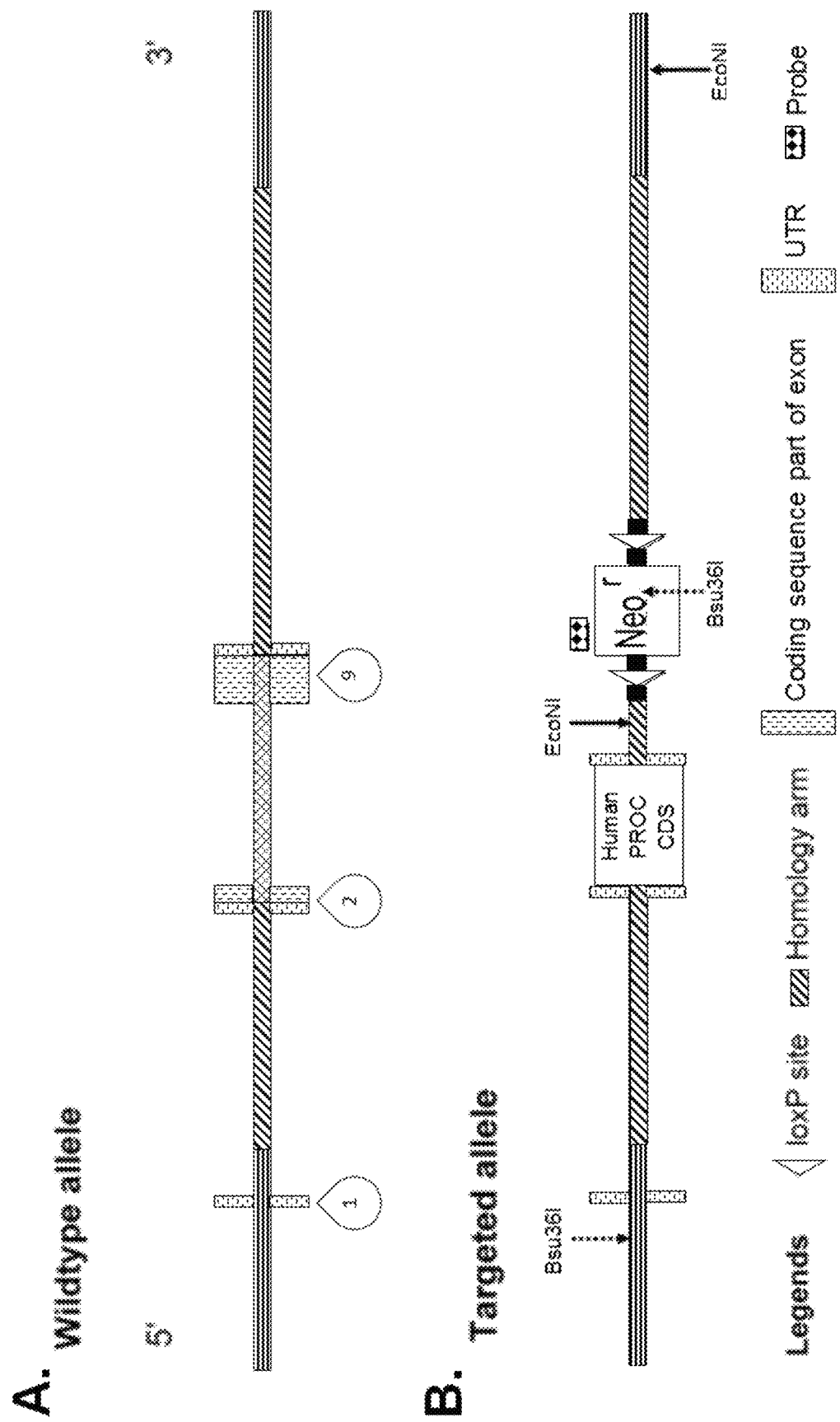

In some embodiments, Southern blotting is performed to determine (or confirm) whether or not the desired homologous recombination event (targeting event) has occurred. In such analysis, genomic DNA isolated from the transfected non-human pluripotent stem cells under investigation (i.e. the potentially targeted non-human pluripotent stem cells) is digested with a restriction enzyme (e.g. Bsu36I or EcoNI). In such Southern blotting a probe is used which is capable of hybridising to a DNA fragment of the digested genomic DNA, that fragment being expected to be of a certain (pre-determined) size if the desired homologous recombination event has occurred. In some embodiments, the probe is capable of hybridising to a fragment of the digested genomic DNA that comprises the (or part of the) positive selection marker (e.g. a probe capable of hybridising to the (or part of the) neomycin resistance gene). An exemplary and preferred Southern blotting method is described in the Example section herein (and is depicted in FIG. 7).

In a particularly preferred embodiment, the selecting of one or more transfected non-human pluripotent stem cells to identify one or more non-human pluripotent cell clones in accordance with step (ii) of the above method is as described in the Example section herein.

Typically, a non-human pluripotent stem cell produced in accordance with the invention is heterozygous for a human Protein C allele in accordance with the invention.

In another aspect, the present invention provides a non-human pluripotent stem cell produced by a method of the invention.

In another aspect, the present invention also provides the use of a vector of the invention for the generation of a non-human pluripotent stem cell in which at least one copy of the endogenous nucleotide sequence encoding Protein C in the genome of said non-human pluripotent cell has been replaced by a nucleotide sequence encoding human Protein C, encoding a functional fragment of human Protein C or encoding a functional variant of human Protein C. Embodiments of other aspects of the invention described herein apply, mutatis mutandis, to this aspect of the invention.

In another aspect, the present invention provides a method of producing (or generating) a genetically modified non-human animal of the invention. Embodiments of other aspects of the invention described herein apply, mutatis mutandis, to this aspect of the invention.

In some embodiments, said method comprises:

(i) providing a non-human pluripotent stem cell in which at least one copy of the endogenous nucleotide sequence encoding Protein C in the genome of said non-human pluripotent stem cell has been replaced by a nucleotide sequence encoding human Protein C, encoding a functional fragment of human Protein C or encoding a functional variant of human Protein C; and (ii) generating a genetically modified non-human animal from said non-human pluripotent stem cell.

Methods of generating genetically modified non-human animals from non-human pluripotent stem cells are well-known in the art.

In some embodiments, the non-human pluripotent stem cell of (i) is produced by a method for producing a non-human pluripotent stem cell in accordance with the present invention.

In some embodiments, the non-human pluripotent stem cell is a non-human pluripotent stem cell in which one copy of the endogenous nucleotide sequence encoding Protein C in the genome of said non-human pluripotent cell has been replaced by a nucleotide sequence encoding human Protein C, encoding a functional fragment of human Protein C or encoding a functional variant of human Protein C. Thus, in some embodiments, the non-human pluripotent stem cell is heterozygous for a human Protein C allele in accordance with the invention.

Typically and preferably, the step of generating a genetically modified non-human animal of step (ii) comprises (a) the introduction of one or more non-human pluripotent stem cells of step (i) into a pre-implantation embryo of an animal of the same species;
(b) the transfer of a said pre-implantation embryo into which one or more of said non-human pluripotent stem cells have been introduced in (a) into a female pseudo-pregnant non-human animal of the same species; and
(c) identifying a founder animal amongst the offspring of the female non-human animal of (b); and optionally
(d) mating said founder animal of (c) and identifying offspring thereof that have a genome in which at least one copy of the endogenous nucleotide sequence encoding Protein C has been replaced by a nucleotide sequence encoding human Protein C, encoding a functional fragment of human Protein C or encoding a functional variant of human Protein C.

In some embodiments, in step (a) the one or more non-human pluripotent stem cells and the pre-implantation embryo are each derived from non-human animal strains having different coat colours (i.e. the one or more non-human pluripotent stem cells is derived from a non-human animal having one coat colour and the pre-implantation embryo is derived from a non-human animal of the same species having a different coat colour).

In some embodiments, in step (a) the introduction of one or more non-human pluripotent stem cells into a pre-implantation embryo is done by injection.

In some embodiments, in step (c) the identification of founder animals is done by identifying those of the female animal's offspring that exhibit coat colour chimerism. Such coat colour chimeras are founder animals (F0 generation).

In some embodiments, in step (d) a founder animal is typically mated with a non-founder animal of the same species. In some embodiments, in step (d), if the non-human pluripotent stem cells of (a) comprise a marker for positive selection flanked by site-specific recombination sites (e.g. loxP sites), the founder animal may be mated with an animal that expresses a site-specific recombinase enzyme (e.g. Cre recombinase) in order to remove the marker for positive selection.

Typically, in step (d), the identifying of offspring comprises determining the genotype of the offspring to identify offspring that have a genome in which at least one copy of the endogenous nucleotide sequence encoding Protein C has been replaced by a nucleotide sequence encoding human Protein C, encoding a functional fragment of human Protein C or encoding a functional variant of human Protein C. Put another way, in step (d) the identifying of offspring comprises identifying those offspring that result from germline transmission of genomic DNA of the non-human pluripotent stem cell of (a), said genomic DNA comprising a human Protein C allele in accordance with the invention.

In some embodiments, determining the genotype of the offspring is performed by a PCR-based method and/or by DNA sequencing. Suitable methods are known in the art. A preferred PCR-based method and DNA sequencing method are described in the Example section herein, and represent preferred embodiments.

In some embodiments, the genetically modified non-human animal produced by the method of the invention is an animal in which one copy of the endogenous nucleotide sequence encoding Protein C in the genome of said animal has been replaced by a nucleotide sequence encoding human Protein C, encoding a functional fragment of human Protein C or encoding a functional variant of human Protein C. Thus, in some embodiments, the non-human animal is heterozygous for a human Protein C allele (i.e. it has one copy of a human Protein C allele in accordance with the invention and one endogenous non-human Protein C allele). Identifying an animal as such a heterozygote may be done by a PCR-based method, for example as described in the Example section herein.

In some embodiments, the genetically modified non-human animal produced by the method of the invention is an animal in which both copies of the endogenous nucleotide sequence encoding Protein C in the genome of said animal have been replaced by a nucleotide sequence encoding human Protein C, encoding a functional fragment of human Protein C or encoding a functional variant of human Protein C. Thus, in some embodiments, the non-human animal is homozygous for a human Protein C allele (i.e. it has two copies of a human Protein C allele in accordance with the invention and no endogenous non-human Protein C allele). Identifying an animal as such a homozygote may be done by a PCR-based method, for example as described in the Example section herein.

Producing non-human animals that are homozygous for a human Protein C allele in accordance with the invention may be done by mating together non-human animals that are heterozygous for a human Protein C allele in accordance with the invention and identifying (e.g. by PCR-based genotyping) amongst the offspring of such a mating those animals that are homozygous for a human Protein C allele in accordance with the invention.

Thus, in some embodiments, the method of producing (or generating) a genetically modified non-human animal of the invention further comprises steps of identifying non-human animals produced as being heterozygous for a human Protein C allele in accordance with the invention, mating such heterozygous non-human animals together, and identifying offspring from said mating that are homozygous for a human Protein C allele in accordance with the invention. Such a method thereby produces a genetically modified non-human animal in accordance with the invention that is homozygous for a human Protein C allele in accordance with the invention. Thus, in some embodiments, the invention provides a method for producing a genetically modified non-human animal in which both copies of the endogenous nucleotide sequence encoding Protein C in the genome of said non-human animal have been replaced by a nucleotide sequence encoding human Protein C, encoding a functional fragment of human Protein C or encoding a functional variant of human Protein C.

In some embodiments, the method of producing (or generating) a genetically modified non-human animal of the invention further comprises one or more steps to introduce (or make) one or more additional genetic modifications into the genome of the non-human animal (i.e. additional to the replacement of an endogenous nucleotide sequence encoding Protein C by a nucleotide sequence encoding human Protein C or fragment or variant thereof).

In some embodiments, the further genetic modification is a modification that results in the down regulation or inactivation (or renders the animal deficient in or devoid of) of one or more other (i.e. non-Protein C) genes. For example, the further genetic modification may be a knock-out of one or more other genes. In some embodiments, the other gene is a gene encoding a blood clotting factor (e.g. one or more blood clotting factors may additionally be knocked-out). In some embodiments, the other gene is a gene encoding Factor VIII (e.g. Factor VIII may additionally be knocked-out). In some embodiments, the other gene is a gene encoding Factor IX (e.g. Factor IX may additionally be knocked-out). In some embodiments, there may be further genetic modifications in the genes encoding Factor VIII and Factor IX (e.g. Factor VIII and Factor IX may additionally be knocked-out).

The introduction of one or more further genetic modifications (e.g. gene knock-outs) may be done by any appropriate means, e.g. by mating a genetically modified non-human animal of the present invention with an animal of the same species which comprises the desired further genetic modification(s) (e.g. which has the desired gene knocked-out). Thus, in some embodiments, methods may further comprise mating a genetically modified non-human animal of the invention with an animal of the same species which has Factor VIII and/or Factor IX knocked out. Appropriate mating strategies can be readily devised to produce and select (e.g. by genotyping such as by PCR-based genotyping) non-human animals which comprise a genetic modification in accordance with the invention (i.e. the replacement of at least one endogenous nucleotide sequence encoding Protein C by a nucleotide sequence encoding human Protein C or fragment or variant thereof) and an additional genetic modification (such as a knock-out of Factor VIII and/or Factor IX).

In some embodiments, a non-human animal of the invention additionally comprises a knock-out of Factor VIII. A mating strategy to produce and select (identify) such non-human animals is described in the Example section herein and represents a preferred mating strategy in accordance with the invention.

Non-human animals (e.g. mice) comprising a genetic modification (e.g. knock-out) of one or more additional genes (e.g. to be used in matings as described herein) may be produced by any suitable means (e.g. by preparing non-human embryonic stem cells with the desired genetic modification and generating genetically modified non-human animals therefrom). However, in many cases, as is the case for a Factor VIII knock-out mouse, non-human animals comprising a desired genetic modification (e.g. a gene knock-out) are commercially available (e.g. from The Jackson Laboratory, US).

A particularly preferred method of producing (or generating) a genetically modified mouse of the invention is described in the Example section herein.

In another aspect, the present invention provides a genetically modified non-human animal produced by a method of producing of the invention.

In another aspect, the present invention provides a method of testing one or more agents (e.g. candidate therapeutic agents or drugs), said method comprising
(a) providing a genetically modified non-human animal (e.g. a mouse) of the present invention; and
(b) administering to said animal one or more agents to be tested.

Typically, such methods are to identify the potential use of the one or more agents in therapy (e.g. human therapy).

Such methods of testing may alternatively be considered methods of screening or investigating. Such methods of testing (or screening or investigating) would typically be considered pre-clinical methods. Accordingly, although these methods aim to identify the potential for an agent to be used in therapy, such testing methods would not themselves be considered to be therapeutic methods. Thus, in some embodiments, the methods of testing in accordance with the present invention are not methods of therapeutic treatment.

In preferred embodiments of methods of testing of the invention, in the genetically modified non-human animal two (i.e. both) copies of the endogenous nucleotide sequence encoding Protein C in the genome of the non-human animal have been replaced by a nucleotide sequence encoding human Protein C, encoding a functional fragment of human Protein C or encoding a functional variant of human Protein C. Thus, in preferred embodiments, the genetically modified non-human animal is homozygous for a human Protein C allele in accordance with the invention.

In some embodiments, methods of testing in accordance with the invention further comprise a step of assessing (or determining or evaluating) whether or not (or the extent to which) there has been an alteration in one or more physiological activities (or functions) in the animal, preferably an alteration in one or more therapeutically relevant physiological activities (or functions). The relevant physiological activity to be assessed may depend on the particular therapy of interest (i.e. depend on the particular disease or condition for which a potentially useful therapeutic agent is being tested), e.g. as discussed elsewhere herein.

In some embodiments, the alteration in one or more physiological activities (or functions) in the animal is an alteration as compared to an appropriate control.

A "control" physiological activity or "control level" of a physiological activity may be the physiological activity in a control animal or a control population of animals. Appropriate controls for use in the methods of the invention would be readily identified by a person skilled in the art. For example, a control physiological activity (or control physiological activity level) may be the physiological activity in a genetically modified non-human animal of the invention of the same species that has not had the agent (test agent) administered. Other controls may include the physiological activity (or control physiological activity level) in a wild-type (or normal) non-human animal of the same species. The control level may correspond to the level of the same (or equivalent) physiological activity in an appropriate control animal. Alternatively, the control level may correspond to the level of the physiological activity in question in the same individual genetically modified non-human animal measured at an earlier time point (e.g. comparison with a "baseline" level in that animal). Control levels may also be referred to as "normal" levels or "reference" levels. The control level may be a discrete figure or a range. Although the control level for comparison could be derived by testing an appropriate control animal or population of control animals, the testing methods of the invention would not necessarily involve carrying out active tests on control animals as part of a method of the present invention, but may involve a comparison with a control (or control level) which had been determined previously from a control animal (or control population of animals) and was known to the person carrying out a method of the invention.

The alteration may be an increase or a decrease (increase in the physiological activity or a decrease in the physiological activity). An alteration in a physiological activity (e.g. in comparison to a control) may indicate that the agent is (or may be) therapeutically useful.

Any measurable (or detectable) alteration (increase or decrease as the case may be) in the physiological activity may be indicative that the agent may be therapeutically useful. To be indicative that the agent may be therapeutically useful, the physiological activity is preferably significantly altered, compared to a control. More preferably, the significantly altered levels are statistically significant, preferably with a p-value of <0.05.

In some embodiments, an alteration (an increase or decrease as the case may be) in the physiological activity (or level of physiological activity) of $\geq 2\%$, $\geq 3\%$, $\geq 5\%$, $\geq 10\%$, $\geq 25\%$, $\geq 50\%$, $\geq 75\%$, $\geq 100\%$, $\geq 200\%$, $\geq 300\%$, $\geq 400\%$, $\geq 500\%$, $\geq 600\%$, $\geq 700\%$, $\geq 800\%$, $\geq 900\%$ or $\geq 1,000\%$ compared to the physiological activity (or level of physiological activity) in an appropriate control indicates that the agent may be therapeutically useful.

As indicated above, methods of testing agents in accordance with the present invention may identify the potential for the use of such agents in therapy (e.g. human therapy). In preferred embodiments, the therapy (or potential therapy) is therapy (or potential therapy) of a disease or condition associated with Protein C or APC (or the Protein C or APC pathway). In some embodiments, the therapy is therapy of a disease or condition characterised by an aberrant, or abnormal or dysregulated molecular mechanism, molecular pathway or cascade wherein Protein C or APC (or the Protein C pathway or APC pathway) is a component of (or associated with, or a part of, or involved in the regulation of) said molecular mechanism, molecular pathway or cascade. In some embodiments, the therapy is therapy of a pathophysiological condition involving Protein C or APC (or the Protein C pathway or APC pathway).

In some embodiments, the therapy is therapy of a bleeding disorder such as haemophilia (e.g. haemophilia A or haemophilia B) or other disease characterized by impaired clotting.

In some embodiments, the therapy is therapy of a disease or condition characterized by inflammation and/or apoptosis (e.g. aberrant or unwanted or excessive inflammation and/or apoptosis), e.g. sepsis.

In preferred embodiments, the agents to be tested include agents that potentially alter the level and/or functional activity of human Protein C or APC (or the Protein C or APC pathway). Such agents may include agents from natural sources, such as a cell extracts, and agents from synthetic sources such as chemical compound libraries, or biological libraries such as antibody or peptide libraries.

In preferred embodiments, the agents to be tested include agents that bind to (or specifically bind to or directly bind to or interact with) human protein C or human APC. Agents may include chemical compounds (e.g. small molecule chemical compounds) and antibodies (or antigen binding fragments thereof) that bind to (or specifically bind to) human Protein C or human APC.

In preferred embodiments, the agent to be tested is an antibody or antigen binding fragment thereof. In particularly preferred embodiments, the agent to be tested is an antibody that binds to (or specifically binds to) human protein C or human APC. Preferably, such antibodies are monoclonal antibodies.

In other embodiments, the agent to be tested is a nucleic acid-based molecule (e.g. an RNAi, shRNA or siRNA molecule) that reduces or inhibits the translation of human Protein C mRNA.

The agents to be tested may include antagonists (or inhibitors) and/or agonists (or potentiators) of human Protein C or human APC (or the human Protein C or human APC pathway). Whether to test agents that are antagonists (or that are potentially antagonists) of human Protein C or human APC or whether to screen agents that are agonists (or that are potentially agonists) of human Protein C or human APC may depend on the particular disease or condition for which a potentially useful therapeutic agent is being screened, tested or investigated (or sought).

For example, in embodiments in which a method of testing agents (e.g. candidate therapeutic agents or drugs) is to identify their potential use in haemophilia (e.g. haemophilia A or haemophilia B) therapy (or therapy of other diseases characterized by impaired clotting), testing antagonists (or inhibitors) of human Protein C or human APC is typically preferred. Such antagonists (or inhibitors) may include antibodies (antagonistic antibodies) that bind to (or specifically bind to) human protein C or human APC (or antigen binding fragments of such antibodies), or serine protease inhibitors (e.g. small molecule serine protease inhibitors). Antibodies, or antigen binding fragments thereof, that bind to (or specifically bind to) human Protein C or human APC are preferred. Monoclonal antibodies are particularly preferred.

By way of another example, in embodiments in which a method of testing agents (e.g. candidate therapeutic agents or drugs) is to identify their potential use in the therapy of a disease or condition characterized by inflammation and/or apoptosis (e.g. sepsis), screening for agonists of human Protein C or human APC is typically preferred.

As typically and preferably the agents being tested are agents that potentially alter the level and/or functional activity of human Protein C or human APC (or the Protein C or APC pathway), typically the physiological activity (or function) assessed is a physiological activity (or function) that is associated with Protein C or APC, or associated with the Protein C or APC pathway. Thus, in some embodiments the physiological activity (or function) assessed is a physiological activity (or function) that is associated with Protein C or APC, or associated with the Protein C or APC pathway. A physiological activity associated with Protein C or APC may be any physiological activity characterised by the involvement of a molecular mechanism or signalling cascade in which Protein C or APC is a component. In some embodiments, biomarkers, such as the expression (or level of expression) of certain genes or proteins may be used as a readout of physiological activity.

Blood clotting is a preferred physiological activity. Such a physiological activity may be the time taken for bleeding to cease following the initiation of bleeding, or the rate of bleeding following the initiation of bleeding, or the amount of bleeding following the initiation of bleeding.

Thus, in some embodiments, the physiological activity (or function) is an activity associated with blood clotting (or bleeding). In some embodiments, the physiological activity (or function) is the time taken for blood clotting to occur, e.g. the time taken for bleeding cessation (or cessation of blood leakage) to occur following the initiation of bleeding, e.g. following a bleeding injury. In some embodiments, for example when the genetically modified non-human animal is a mouse, the physiological activity (or function) is the time take for the cessation of bleeding (or blood leakage) following tail transection (e.g. transection of the distal tail).

In some embodiments, the time taken for bleeding cessation may be determined by administering an agent to be tested to a genetically modified non-human animal of the invention, then initiating (or inducing) bleeding in said animal and measuring the time taken for bleeding to cease. If the agent (test agent) provides an improvement in bleeding cessation, e.g. a reduction in the time taken for bleeding to cease, as compared to a control, that is typically indicative that the agent may be useful for the treatment of haemophilia or other disease or condition characterised by impaired blood clotting. The control may be as discussed elsewhere herein.

In some embodiments, the time taken for bleeding cessation may be determined by (i) administering an agent to be tested to a genetically modified mouse (e.g. an anesthetized mouse) of the present invention (e.g. administering by injection into the orbital vein), optionally the tail of the mouse being immersed in saline (e.g. at 37° C.), (ii) transecting the distal tail of the mouse (e.g. at 4 mm) to initiate bleeding (e.g. arterial and venous bleeding) and optionally immersing the tail in saline (e.g. at 37° C.), (iii) measuring the bleeding time following tail transection (typically bleeding time is the length of time following transection at which blood leakage has ceased for at least 1 minute). In some embodiments, the transection of (ii) is performed about 5 minutes after the administration of the agent of (i). A particularly preferred method for determining bleeding cessation is described in the Example section herein.

In some other embodiments, the time taken for bleeding cessation may be determined by initiating (or inducing) bleeding in a genetically modified non-human animal of the invention, administering an agent to be tested to said animal and measuring the time taken for bleeding to cease. If the agent provides an improvement in bleeding cessation, e.g. a reduction in the time taken for bleeding to cease, in comparison to a control, that is typically indicative that the agent may be useful for the treatment of haemophilia or other disease or condition characterised by impaired blood clotting.

In some embodiments, when the physiological activity (or function) being assessed is an activity associated with blood clotting (or bleeding), e.g. as discussed above, the method of testing in accordance with the invention is to identify the potential use of the agent in the therapy of a bleeding disorder such as haemophilia (e.g. haemophilia A or haemophilia B) or other disease or condition characterized by impaired clotting.

As indicated above, if the agent provides an improvement in bleeding cessation, e.g. a reduction in the time taken for bleeding to cease, in comparison to a control, that is typically indicative that the agent may be useful for the treatment of haemophilia or other disease or condition characterised by impaired blood clotting. In some embodiments, a reduction of ≥2%, ≥3%, ≥5%, ≥10%, ≥25%, ≥50%, ≥75%, ≥80%, ≥90% or even 100% in the time taken for bleeding to cease in comparison to a control is indicative that the agent may be therapeutically useful in the therapy (e.g. human therapy) of a bleeding disorder such as haemophilia (e.g. haemophilia A or haemophilia B) or other disease characterized by impaired clotting. In some embodiments, a reduction of at least 30 seconds, at least 1 minute, at least 2 minutes, at least 3 minutes, at least 4 minutes, at least 5 minutes, at least 10 minutes, at least 15 minutes, at least 30 minutes or at least 1 hour in the time taken for bleeding to cease, in comparison to a control, is indicative that the agent may be therapeutically useful in the therapy (e.g. human therapy) of a bleeding disorder such as haemophilia (e.g. haemophilia A or haemophilia B) or other disease characterized by impaired clotting. Suitable controls are discussed elsewhere herein.

In some embodiments of methods of testing agents to identify potentially useful agents for the therapy of a bleeding disorder such as haemophilia (e.g. haemophilia A or haemophilia B) or other disease characterized by impaired clotting, the genetically modified non-human animal may be deficient in (e.g. devoid of) one more clotting factors, such as Factor VIII or Factor IX (e.g. the genetically modified non-human animal may have one or more genes encoding clotting factors, such as Factor VIII and/or Factor IX, knocked-out). Thus, in some embodiments, the genetically modified non-human animal used in such methods may comprise one or more additional genetic modifications that render them deficient in (e.g. devoid of) Factor VIII and/or Factor IX, e.g. they may additionally have the gene encoding Factor VIII and/or the gene encoding Factor IX knocked-out, or the Factor VIII and/or Factor IX gene or protein may be otherwise down-regulated or inactivated. Deficiency in Factor VIII is characteristic of haemophilia A. Deficiency in Factor IX is characteristic of haemophilia B.

In some embodiments, the effect of an agent being tested on a physiological activity (or function) (e.g. an activity associated with blood clotting such as the time taken for bleeding to cease as discussed above) may be compared to the effect of a blood clotting factor (such as Factor VIII or Factor IX) on the same physiological activity. In some embodiments, the clotting factor (e.g. Factor VIII or Factor IX) may be a human clotting factor. The clotting factor may be a recombinant clotting factor (e.g. a recombinant human clotting factor) or a clotting factor purified from plasma (e.g. from human plasma). Thus, in some embodiments a control physiological activity is the physiological activity in a genetically modified non-human animal of the invention to which a blood clotting factor (e.g. Factor VIII or IX) has been administered (e.g. a positive control).

In some embodiments, when the control physiological activity is the physiological activity in a genetically modified non-human animal of the invention to which a blood clotting factor (such as Factor VIII or IX) has been administered, if the agent being tested, exhibits ≥2%, ≥3%, ≥5%, ≥10%, ≥25%, ≥50%, ≥75%, ≥80%, ≥90% or even ≥100% of the activity of the administered blood clotting factor (e.g. Factor VIII or IX or other procoagulant clotting factor), e.g. as determined by (or in terms of) the time taken for bleeding to cease, then that may indicate that the agent is useful for the therapy (e.g. human therapy) of a bleeding disorder such as haemophilia (e.g. haemophilia A or haemophilia B) or other disease characterized by impaired clotting.

In some embodiments, if the physiological activity (e.g. the time taken for bleeding cessation) in a genetically modified non-human animal of the invention to which a test agent being tested has been administered is ≥2%, ≥3%, ≥5%, ≥10%, ≥25%, ≥50%, ≥75%, ≥80%, ≥90% or even ≥100% of the same physiological activity in a control non-human animal of the same species to which a blood clotting factor such as Factor VIII or Factor IX (or other procoagulant clotting factor) has been administered, then that may indicate that the agent is useful for therapy (e.g. human therapy) of a bleeding disorder such as haemophilia (e.g. haemophilia A or haemophilia B) or other disease characterized by impaired clotting.

In some embodiments, if the genetically modified non-human animal is deficient in Factor VIII, the physiological activity in a genetically modified non-human animal of the invention to which Factor VIII has been administered may be used as a control. In some embodiments, if the genetically modified non-human animal is deficient in Factor IX, the physiological activity in a genetically modified non-human animal of the invention to which Factor IX has been administered may be used as a control.

As discussed above, in some embodiments of methods of testing agents in accordance with the invention the purpose is to identify agents that are potentially useful in the therapy of a disease or condition that is characterized by inflammation and/or apoptosis (e.g. aberrant or unwanted or excessive inflammation and/or apoptosis), e.g. sepsis.

In some such embodiments, the physiological activity (or function) assessed is inflammation or apoptosis. Any suitable means for assessing inflammation or apoptosis may be used and the skilled person is familiar with appropriate methods and assays (e.g. by challenging the animal with lipopolysaccharide (LPS) or *E. coli* and assessing the effect of an agent being tested thereon). If inflammation and/or apoptosis is decreased in a genetically modified non-human animal that has been treated with an agent being tested, as compared to a control, that is typically indicative that the agent may be useful for the treatment of a disease or condition that is characterized by inflammation and/or apoptosis (e.g. aberrant or unwanted or excessive inflammation and/or apoptosis), e.g. sepsis. The control may be as discussed elsewhere herein.

As indicated above, methods of testing can aim to identify the potential use of agents in therapy (e.g. human therapy). Therapy includes treatment and prophylaxis.

In another aspect, the present invention provides an agent identified by a method of testing of the invention. The present invention also provides a method of treating a disease or condition in a subject (preferably a human), e.g. a disease or condition as defined elsewhere herein, said method comprising administering a therapeutically effective amount of an agent identified by a method of testing of the invention. The present invention also provides an agent identified by a method of testing of the invention for use in therapy (preferably human therapy), preferably said therapy is of a disease or condition defined elsewhere herein.

In another aspect, the invention provides the use of a genetically modified non-human animal of the invention for drug screening or drug testing. In another aspect, the present invention provides the use of a genetically modified non-human animal of the invention for the screening or testing of candidate therapeutic agents, typically candidate therapeutic agents that target (or bind to) human Protein C or human APC. Examples of such agents are discussed elsewhere herein.

Such testing would typically be considered experimental testing, or pre-clinical testing. The agents (or drugs) would typically be candidate therapeutic agents, but their use in testing would not typically be considered a therapeutic use.

In another aspect, the invention provides the use of a genetically modified non-human animal of the invention (e.g. mouse) as an experimental animal model. In some embodiments, the experimental model (e.g. mouse model) is an experimental model of a disease or condition, preferably a disease or condition associated with Protein C or APC (or the Protein C or APC pathway). In some embodiments, the disease or condition is a disease or condition characterised by an aberrant, or abnormal or dysregulated molecular mechanism, molecular pathway or cascade wherein Protein C or APC is a component of (or associated with, or a part of, or involved in the regulation of) said molecular mechanism, molecular pathway or cascade. In some embodiments, the disease or condition is a pathophysiological condition involving Protein C or APC (or the Protein C or APC pathway).

In some embodiments, the experimental model is an experimental model (e.g. mouse model) of a bleeding disorder such as haemophilia (e.g. haemophilia A or haemophilia B) or other disease characterized by impaired clotting.

In some embodiments, the experimental model is an experimental model (e.g. mouse model) of a disease or condition characterized by inflammation and/or apoptosis (e.g. aberrant or unwanted or excessive inflammation and/or apoptosis), e.g. sepsis.

In some embodiments in which a genetically modified non-human animal of the invention is used as an experimental model animal, the animal may comprise one or more further genetic modifications (e.g. may comprise a knock-out of one or more other genes).

In some embodiments in which a genetically modified non-human animal of the invention is used as an experimental model, for example of haemophilia (or other bleeding disorder or disease or condition characterized impaired clotting), the animal may be deficient in (e.g. devoid of) one more clotting factors. In some embodiments in which a genetically modified non-human animal of the invention is used as an experimental model, for example of haemophilia (or other bleeding disorder or disease or condition characterized impaired clotting), the animal may be deficient in (e.g. devoid of) Factor VIII and/or Factor IX. Thus, in some embodiments in which a genetically modified non-human animal of the invention is used as an experimental model, for example of haemophilia, the genetically modified non-human animal may comprise one or more additional genetic modifications to render them deficient in (e.g. devoid of) Factor VIII and/or Factor IX, e.g. they may additionally have the gene encoding Factor VIII and/or the gene encoding Factor IX knocked-out, or the Factor VIII and/or Factor IX gene or protein may be otherwise down-regulated or inactivated.

In some other embodiments in which a genetically modified non-human animal of the invention is used as an experimental model of a bleeding disorder the animal may be deficient in (e.g. devoid of) Factor X and/or Factor XI. Thus, in some embodiments in which a genetically modified non-human animal of the invention is used as an experimental model the genetically modified non-human animal may comprise one or more additional genetic modifications to render them deficient in (e.g. devoid of) Factor X and/or Factor XI, e.g. they may additionally have the gene encoding Factor X and/or the gene encoding Factor XI knocked-out, or the Factor X and/or Factor XI gene or protein may be otherwise down-regulated or inactivated.

Where the terms "comprise", "comprises", "comprising", "has" or "having", or other equivalent terms are used herein, then in some more specific embodiments these terms include the term "consists of", "consisting of", "consisting essentially of", or "consists essentially of", or other equivalent terms.

As used throughout this application, the terms "a" and "an" are used in the sense that they mean "at least one", "at least a first", "one or more" or "a plurality" of the referenced components or steps, except in instances wherein an upper limit is thereafter specifically stated.

List of Nucleotide and Amino Acid Sequences Disclosed Herein and their Sequence Identifiers (SEQ ID NOs)

All nucleotide sequences are recited herein 5' to 3' in line with convention in this technical field.

```
Nucleotide sequence of targeting vector
                                                        SEQ ID NO: 1
   1 CGCTTA CAATTT CCATTC GCCATT CAGGCT GCGCAA CTGTTG GGAAGG GCGATC GGTGCG

61 GGCCTC TTCGCT ATTACG CCAGCT GGCGAA AGGGGG ATGTGC TGCAAG GCGATT AAGTTG

121 GGTAAC GCCAGG GTTTTC CCAGTC ACGACG TTGTAA AACGAC GGCCAG TGAATT GTAATA

181 CGACTC ACTATA GGGCGA ATTGGA GCTCCA CCGCCC GGGCTG GTTCTT TCCGCC TCAGAA

241 GCCATA GAGCCC ACCGCA TCCCCA GCATGC CTGCTA TTGTCT TCCCAA TCCTCC CCCTTG

301 CTGTCC TGCCCC ACCCCA CCCCCC AGAATA GAATGA CACCTA CTCAGA CAATGC GATGCA

361 ATTTCC TCATTT TATTAG GAAAGG ACAGTG GGAGTG GCACCT TCCAGG GTCAAG GAAGGC

421 ACGGGG GAGGGG CAAACA ACAGAT GGCTGG CAACTA GAAGGC ACAGTC GAGGCT GATCAG

481 CGAGCT CTAGGA TCTGCA TTCCAC CACTGC TCCCAT TCATCA GTTCCA TAGGTT GGAATC

541 TAAAAT ACACAA ACAATT AGAATC AGTAGT TTAACA CATTAT ACACTT AAAAAT TTTATA

601 TTTACC TTAGAG CTTTAA ATCTCT GTAGGT AGTTTG TCCAAT TATGTC ACACCA CAGAAG

661 TAAGGT TCCTTC ACAAAG AGATCG CCTGAC ACGATT TCCTGC ACAGGC TTGAGC CATATA

721 CTCATA CATCGC ATCTTG GCCACG TTTTCC ACGGGT TTCAAA ATTAAT CTCAAG TTCTAC

781 GCTTAA CGCTTT CGCCTG TTCCCA GTTATT AATATA TTCAAC GCTAGA ACTCCC CTCAGC

841 GAAGGG AAGGCT GAGCAC TACACG CGAAGC ACCATC ACCGAA CCTTTT GATAAA CTCTTC

901 CGTTCC GACTTG CTCCAT CAACGG TTCAGT GAGACT TAAACC TAACTC TTTCTT AATAGT

961 TTCGGC ATTATC CACTTT TAGTGC GAGAAC CTTCGT CAGTCC TGGATA CGTCAC TTTGAC

1021 CACGCC TCCAGC TTTTCC AGAGAG CGGGTT TTCATT ATCTAC AGAGTA TCCCGC AGCGTC

1081 GTATTT ATTGTC GGTACT ATAAAA CCCTTT CCAATC ATCGTC ATAATT TCCTTG TGTACC

1141 AGATTT TGGCTT TTGTAT ACCTTT TTGAAT GGAATC TACATA ACCAGG TTTAGT CCCGTG

1201 GTACGA AGAAAA GTTTTC CATCAC AAAAGA TTTAGA AGAATC AACAAC ATCATC AGGATC

1261 CATGGC ACGCGC TTCTAC AAGGCG CTGGCC GAAGAG GTGCGG GAGTTT CACGCC ACCAAG

1321 ATCTGC GGCACG CTGTTG ACGCTG TTAAGC GGGTCG CTGCAG GGTCGC TCGGTG TTCGAG

1381 GCCACA CGCGTC ACCTTA ATATGC GAAGTG GACCTG GGACCG CGCCGC CCCGAC TGCATC

1441 TGCGTG TTCGAA TTCGCC AATGAC AAGACG CTGGGC GGGGTT TGCTCG ACATTG GGTGGA

1501 AACATT CCAGGC CTGGGT GGAGAG GCTTTT TGCTTC CTCTTG CAAAAC CACACT GCTCGA

1561 CATTGG GTGGAA ACATTC CAGGCC TGGGTG GAGAGG CTTTTT GCTTCC TCTTGA AAACCA

1621 CACTGC TCGATT TGTTAG CAGCCT CGAATC AACCCG GGCGAT CCTAGG CGATGA GATCTA

1681 GCTGTC GCGAAG AGTGGC GCGCCT CCCTGC ACAGCT AGTCAC AACGAA GGAAGG CGCTTA
```

-continued

```
1741 GGGAAC CCTGGC AGCTTG CAAAAC GCAAAG GGCTAC GGCTGC ATCGCT CTTTTC CAGACT

1801 TCTCAG CTGGGA GCTTCT GGCAGT TTTCCC GAGTCA CTCCTT TCTCTC ACTAGC TCACAA

1861 AGTGGC CAGCTG AGTCAG AAGCCT CCTTCT AGTACA GGCCTG CCTCCC ACCAAC GCCATC

1921 AATCAG GACAAG TAAGGA AGACTT CTGAGT CGCCCC CCCCCC CCACCG GTCAAA TAGAGG

1981 GGACAT CTTATC ACTGAT GGCATC CTAGAT TGGTGA TATATG TAATTA TTTTTG AGTGTG

2041 CTACCC ACGAAC AAGCTA TATCTG TTTATG GTTGCT GTTGTT TTGGTT TTTGTT TTCTTT

2101 TAAGGT TCTCAT CCCTCA GCCACT GCGGGC AAAAAT GAGACC ACATTT GCCAAT AAGTTT

2161 GAACAC GCTCAA CCCTCT CTTTCT CCCTCC CTTTCT GATAGA CAATTC CTTCGG TAGGCA

2221 GAGGTG AGCAAT GGGCAC ACGGAG CCTTCC AGAGCT GGGATC AGAAAA CCTCTT GTTTGT

2281 TTGTCT GGGGAG AGGGAG GTTCGG CACCAA GGGCTA AGCAAA TATTTG CGGTTA TGGATT

2341 AACCTG ACTCCC AGACTG ACATGG CGCTAC CTGGAC GAAATT GCAGTT TCTCCT TGGCCC

2401 ACGCCT GTAAGT CCCCCT CATTGC AAGACT GTGAAG GACTGT GGAGGG AGGGGA GGGGAG

2461 GAAAGT CCAGCT GGGAGG AAGGTG ACGTTC TTGAGC TAAGGC TCTCCA GGCAGA CTGAAA

2521 TGTGGG GCCAAG GAAAAT GAGCGC CCAAAC TCTATC TGGACC AAGGCG TGGGTT CCCTAC

2581 AATCCA GGTGAC CATCTC GACACA TGAGAT TTTGTG GATCAA GTGGAC AGCAGT CAAAGG

2641 GTTCCC TATGAT CAGGAA CCATCC TCAGAG CAATCT TGAAAC CCAGAA CCCCAC TACTCC

2701 CCTCTG CCCTGT TCTCTA AGGTGG ACTCTA CAATTC CGGAAG CCAGCA AAGCCG AAGAGT

2761 GAGGCC AGGAGG GGCTGT GCAGCT GGGATA GGCGGG CCTGCC CACCTG GTCTGG GGGACA

2821 CTAGAG GCCTTG TGGTTT GACTAC TGGTTG GGGGCA GGGGTT AAGGTT CCAGAG TTGGGG

2881 CCACAT AGGCTT GGCCTT GAAGCC AAACTC TGCCCT CCTCTT AGGTGT AGGCTT GTGACA

2941 AGCCGC GTATCT CCTCCA AGCCTT TGGGTC CCTTCC CATGAA ATGGAG GTGAGA ATATTC

3001 ATGCCT TCCTCT TTTAAC AGTGAT CAGTGT GTGTGT GTGTGT GTGTGT GTGTGT GTGTGT

3061 GTGTGT GTGTGT GTGTGT GTGTGG TGTAGA GTGTGG TTTCTG GTGTTC AGGGTT GAACCC

3121 AGAATC TTAAAC ATGCCA AGTACG TTCTTT CCTACT GAACTG CAACCC TCCAGT ATCCTG

3181 TACTTG TTGTTT GTTTGT TTGTTT GTTTGT TTGTTC GGAAGC ACCTGT GGTGGC ACACAC

3241 TTACAA TCCTAG TGCTAG AGAGCA GAAACA AGTGGA TCCCTT GGGCTT GCTGGC TGGCCA

3301 GCCTAC GTGATG AGTTTC AGGCAG TGAGAG ACCTTG TCCCAA ACAATA AGGTGG AAGTAA

3361 GCCATG ATGGCA TACCCC TTTAGA GCTAGT ACTCGA GAGGCA GAAGCA GGTGGA GTTTAA

3421 GACCAG CCTGGT CTACAT AGAAGT TCCAGG ATAGCC AAAAAG TACCCA AGGCCA TCCAAA

3481 AAAACA AAAACA AAACAA AACCTG GAGGGA AAAAAA AAACCA GACAAT GCCTGG GGAAGG

3541 ATGAAG GACAGT CAGTCA GATTAT CCCTGG TCAACA CGTGTG CACAAA TCTGTG CACACA

3601 AGAAAG AGCTTC ACATGG GTTACT ATTTGT TTTCCA ACAACT CATTTT TAAGCC CCCACT

3661 CTCTTT CTCTGT TTTTAA AAAAGG TTTATT TATTTT ATGTAT ATGAGT ACATTA TTGCTC

3721 TCTTCA GACACA CCAGAA AAGGAC ATAAGA TTCCAT TACAGA TGGTTG TGAGCC ACCATG

3781 TGGTTG CTGGAA TTTGAA CTCAGG TCCTCT GGAAGA GCAGTC GGTGCT CTTAAC CACTGA

3841 ACCATC TCCCCA GCCCTT CCAACA ACTCTT TATGGA AGAAAC CTATTC TATCCA TTTTAT

3901 AAATGA CAGAAC TGAGGC ACGGAG CACGTA AACATC TTGTTA AATACC TCTCTC TCTCTC

3961 TCTCTC TCCCCA GTAGGA AATGGA ATTTGC CCCAGG CAATGA CTTTTT TTTTTT TTTTTT

4021 TGCTTT CATGTA CCTAGA GTAAGC CCAGCT CTAAAG GCCACG AGATTG TCTGTC TGTGGA

4081 CCGTGG TGTACC CCACTC CCAGAC CCAGCT TCCACA CAGACA ATGAGC TCACAA ACGTCC

4141 TTTACT CCCTTC CTTCCT TGCTTG CTCTGT GTGTGT GTGTGT GTGTGT GTGTGT GTGTTA
```

```
4201 AGAGAT CAACCT CAGACA TTTTCT TTAGGA GCTATT TACCTT GCTTTT TGAGAC AGGGCC

4261 TCCGGA TGGCCT GGAGCT AGTCAC CTGGAG CTGGTC AAGCAG GCTAGG GTGGCT GGCCTA

4321 AGCAAT CCACAG GATCTG CTTATC TCTGCC TCCCCA GTCCTG GGATTA CAAGAA CGCCT

4381 CAGACA CCTAGA TTTCTG TTTTAA TTTTCT ATGGGT TCTGGG GATCTT CTTAA GTCTTC

4441 AAGTAT GCACGG AAAGGG CTTTAT TGACTA AGATAT CTCCCC TGCTCA GGAATG GCCCTT

4501 TCATTC TACTTT GGAGGG AGCTGG GGGTGG GGCGGG GAGCAG CTCAGC TGTGTG TATCCT

4561 TGGAGC TTAGAA GTTCTC CTCAGA CAGGTG TCAGCA GCTCCA GGATGT GGCAGC TCACAA

4621 GCCTCC TGCTGT TCGTGG CCACCT GGGGAA TTTCCG GCACAC CAGCTC CTCTTG ACTCAG

4681 TGTTCT CCAGCA GCGAGC GTGCCC ACCAGG TGCTGC GGATCC GCAAAC GTGCCA ACTCCT

4741 TCCTGG AGGAGC TCCGTC ACAGCA GCCTGG AGCGGG AGTGCA TAGAGG AGATCT GTGACT

4801 TCGAGG AGGCCA AGGAAA TTTTCC AAAATG TGGATG ACACAC TGGCCT TCTGGT CCAAGC

4861 ACGTCG ACGGTG ACCAGT GCTTGG TCTTGC CCTTGG AGCACC CGTGCG CCAGCC TGTGCT

4921 GCGGGC ACGGCA CGTGCA TCGACG GCATCG GCAGCT TCAGCT GCGACT GCCGCA GCGGCT

4981 GGGAGG GCCGCT TCTGCC AGCGCG AGGTGA GCTTCC TCAATT GCTCGC TGGACA ACGGCG

5041 GCTGCA CGCATT ACTGCC TAGAGG AGGTGG GCTGGC GGCGCT GTAGCT GTGCGC CTGGCT

5101 ACAAGC TGGGGG ACGACC TCCTGC AGTGTC ACCCCG CAGTGA AGTTCC CTTGTG GGAGGC

5161 CCTGGA AGCGGA TGGAGA AGAAGC GCAGTC ACCTGA ACGAG ACACAG AAGACC AAGAAG

5221 ACCAAG TAGATC CGCGGC TCATTG ATGGGA AGATGA CCAGGC GGGGAG ACAGCC CCTGGC

5281 AGGTGG TCCTGC TGGACT CAAAGA AGAAGC TGGCCT GCGGGG CAGTGC TCATCC ACCCCT

5341 CCTGGG TGCTGA CAGCGG CCCACT GCATGG ATGAGT CCAAGA AGCTCC TTGTCA GGCTTG

5401 GAGAGT ATGACC TGCGGC GCTGGG AGAAGT GGGAGC TGGACC TGGACA TCAAGG AGGTCT

5461 TCGTCC ACCCCA ACTACA GCAAGA GCACCA CCGACA ATGACA TCGCAC TGCTGC ACCTGG

5521 CCCAGC CCGCCA CCCTCT CGCAGA CCATAG TGCCCA TCTGCC TCCCGG ACAGCG GCCTTG

5581 CAGAGC GCGAGC TCAATC AGGCCG GCCAGG AGACCC TCGTGA CGGGCT GGGGCT ACCACA

5641 GCAGCC GAGAGA AGGAGG CCAAGA GAAACC GCACCT TCGTCC TCAACT TCATCA AGATTC

5701 CCGTGG TCCCGC ACAATG AGTGCA GCGAGG TCATGA GCAACA TGGTGT CTGAGA ACATGC

5761 TGTGTG CGGGCA TCCTCG GGGACC GGCAGG ATGCCT GCGAGG GCGACA GTGGGG GCCCCA

5821 TGGTCG CCTCCT TCCACG GCACCT GGTTCC TGGTGG GCCTGG TGAGCT GGGGTG AGGGCT

5881 GTGGGC TCCTTC ACAACT ACGGCG TTTACA CCAAAG TCAGCC GCTACC TCGACT GGATCC

5941 ATGGGC ACATCA GAGACA AGGAAG CCCCCC AGAAGA GCTGGG CACCTT AGCACC CCTCCC

6001 TGCTCA CCTCTG GACCCT AGAAGT CACTCT TGGAGT AAGGCT GGGCTA GTGAGT ACCAAG

6061 ACAGAG GACATT AAAGGA GCATGC AACAAA CATACC TCCCCG AGTACC TGTCTG TCTTTT

6121 CATCCT TTTTAT GGGCTA TTCTGG GGGAAA GTAACA TTAATT GAGCAT GCACTA CACACC

6181 AAGTCT ATGAAA AGAACC TGCTTA ACTCCC AAAGCA GTTGTG TAGAAG ATCTAG TGGGAT

6241 CTGAGC TGATAT CACTTC TGGGGG TGAGTG GAGGAG ATTGAT TTAGAG AAAGGA ATTTTT

6301 TTAGAA GTTACT GTAAGA GACTAA TAGAGC CTTTCT CAGGGC CTTGGA AAGAGC CCGTGC

6361 TAGTTA CATCAG AAAAGC TTGCCA GTGACC AGTGGC CAGTGA GACTCA GAATGG CCATGT

6421 GGTGGA GCCAGG ATTCAA ACCAAG GTCACA CTCCCA AACTCA GCTGCT TCTCTT CTTTAT

6481 TATCCC TGGGTG TGTGCT GGTGTG TGTGTG CGCGCG TGGGTG TGTGGG TGGATA CATGCA

6541 TGTGTG TGTGTG TGTGTG TGTGTG TGTGTG TGTGTG TGTGTG TGTGTG TTATAT GTTTGG AGACCA

6601 GAGGAC AACTTC GTTTCT CAACAC CATCCA CTTGTT TGTTTT TGTGTT TTGTTT GTTTG

6661 TTGACA CAGGGT CTCTCA CTGTCC TGAAAT CTACCC AGTAGG CTAGGC TGGCTG GCTACC
```

```
6721 AAACCC CACCCC ACCCTG GCTTTG ACAAGT GGAGAC AGAAGA CCAGTA GTCCAC TGGAGA
6781 TGTGAC CAGATG CCCAGA AGGTGC TCCTCA TGGTGC CCTACA GTTTTG TTGAGG AGTCTG
6841 TTTAAT AATGCA GCTGGG TGCAGT GGCAGC ACCTGT AGCCCC CAATAC TGAGGC AGCATT
6901 GCTGCA GTCTGA GAGGTG GGCTC GAGGGA CCTAAT AACTTC GTATAG CATACA TTATAC
6961 GAAGTT ATATTA AGGGTT CCGCAA GCTCTA GTCGAG CCCCAG CTGGTT CTTTCC GCCTCA
7021 GAAGCC ATAGAG CCCACC GCATCC CCAGCA TGCCTG CTATTG TCTTCC AATCC TCCCCC
7081 TTGCTG TCCTGC CCCACC CCACCC CCCAGA ATAGAA TGACAC CTACTC AGACAA TGCGAT
7141 GCAATT TCCTCA TTTTAT TAGGAA AGGACA GTGGGA GTGGCA CCTTCC AGGGTC AAGGAA
7201 GGCACG GGGGAG GGGCAA ACAACA GATGGC TGGCAA CTAGAA GGCACA GTCGAG GCTGAT
7261 CAGCGA GCTCTA GAGAAT TGATCC CCTCAG AAGAAC TCGTCA AGAAGG CGATAG AAGGCG
7321 ATGCGC TGCGAA TCGGGA GCGGCG ATACCG TAAAGC ACGAGG AAGCGG TCAGCC CATTCG
7381 CCGCCA AGCTCT TCAGCA ATATCA CGGGTA GCCAAC GCTATG TCCTGA TAGCGG TCCGCC
7441 ACACCC AGCCGG CCACAG TCGATG AATCCA GAAAAG CGGCCA TTTTCC ACCATG ATATTC
7501 GGCAAG CAGGCA TCGCCA TGGGTC ACGACG AGATCA TCGCCG TCGGGC ATGCGC GCCTTG
7561 AGCCTG GCGAAC AGTTCG GCTGGC GCGAGC CCTGA TGCTCT TCGTCC AGATCA TCCTGA
7621 TCGACA AGACCG GCTTCC ATCCGA GTACGT GCTCGC TCGATG CGATGT TTCGCT TGGTGG
7681 TCGAAT GGGCAG GTAGCC GGATCA AGCGTA TGCAGC CGCCGC ATTGCA TCAGCC ATGATG
7741 GATACT TTCTCG GCAGGA GCAAGG TGAGAT GACAGG AGATCC TGCCCC GGCACT TCGCCC
7801 AATAGC AGCCAG TCCCTT CCCGCT TCAGTG ACAACG TCGAGC ACAGCT GCGCAA GGAACG
7861 CCCGTC GTGGCC AGCCAC GATAGC CGCGCT GCCTCG TCCTGC AGTTCA TTCAGG GCACCG
7921 GACAGG TCGGTC TTGACA AAAAGA ACCGGG CGCCCC TGCGCT GACAGC CGGAAC ACGGCG
7981 GCATCA GAGCAG CCGATT GTCTGT TGTGCC CAGTCA TAGCCG AATAGC CTCTCC ACCCAA
8041 GCGGCC GGAGAA CCTGCG TGCAAT CCATCT TGTTCA ATGGCC GATCCC ATGGTT TAGTTC
8101 CTCACC TTGTCG TATTAT ACTATG CCGATA TACTAT GCCGAT GATTAA TTGTCA ACAGGC
8161 TGCAGG TCGAAA GGCCCG GAGATG AGGAAG AGGAGA ACAGCG CGGCAG ACGTGC GCTTTT
8221 GAAGCG TGCAGA ATGCCG GGCCTC CGGAGG ACCTTC GGGCGC CCGCCC CGCCCC TGAGCC
8281 CGCCCC TGAGCC CGCCCC CGGACC CACCCC TTCCCA GCCTCT GAGCCC AGAAAG CGAAGG
8341 AGCAAA GCTGCT ATTGGC CGCTGC CCCAAA GGCCTA CCCGCT TCCATT GCTCAG CGGTGC
8401 TGTCCA TCTGCA CGAGAC TAGTGA GACGTG CTACTT CCATTT GTCACG TCCTGC ACGACG
8461 CGAGCT GCGGGG CGGGGG GGAACT TCCTGA CTAGGG GAGGAG TAGAAG GTGGCG CGAAGG
8521 GGCCAC CAAAGA ACGGAG CCGGTT GGCGCC TACCGG TGGATG TGGAAT GTGTGC GAGGCC
8581 AGAGGC CACTTG TGTAGC GCCAAG TGCCCA GCGGGG CTGCTA AAGCGC ATGCTC CAGACT
8641 GCCTTG GGAAAA GCGCCT CCCCTA CCCGGT AGAATT CGACG ACCTGC AGCCAA GCTAGC
8701 TTCGCG AGCTCG ACCGAA CAAACG ACCCAA CACCCG TGCGTT TTATTC TGTCTT TTTATT
8761 GCCGCT CAGCTT TACAGT GACAAT GACGGC TGGCGA CTGAAT ATTAGT GCTTAC AGACAG
8821 CACTAC ATATTT TCCGTC GATGTT GAAATC CTTTCT CATATG TCACCA TAAATA TCAAAT
8881 AATTAT AGCAAT CATTTA CGCGTT AATGGC TAATCG CCATCT TCCAGC AGGCGC ACCATT
8941 GCCCCT GTTTCA CTATCC AGGTTA CGGATA TAGTTC ATGACA ATATTT ACATTG GTCCAG
9001 CCACCA GCTTGC ATGATC TCCGGT ATTGAA ACTCCA GCGCGG GCCATA TCTCGC GCGGCT
9061 CCGACA CGGGCA CTGTGT CCAGAC CAGGCC AGGTAT CTCTGA CCAGAG TCATCC TTAGCG
```

```
9121 CCGTAA ATCAAT CGATGA GTTGCT TCAAAA ATCCCT TCCAGG GCGCGA GTTGAT AGCTGG

9181 CTGGTG CAGAT GGCGCG GCAACA CCATTT TTTCTG ACCCGG CAAAAC AGGTAG TTATTC

9241 GGATCA TCAGCT ACACCA GAGACG GAAATC CATCGC TCGACC AGTTTA GTTACC CCCAGG

9301 CTAAGT GCCTTC TCTACA CCTGCG GTGCTA ACCAGC GTTTTC GTTCTG CCAATA TGGATT

9361 AACATT CTCCCA CCGTCA GTACGT GAGATA TCTTTA ACCCTG ATCCTG GCAATT TCGGCT

9421 ATACGT AACAGG GTGTTA TAAGCA ATCCCC AGAAAT GCCAGA TTACGT ATATCC TGGCAG

9481 CGATCG CTATTT TCCATG AGTGAA CGAACC TGGTCG AAATCA GTGCGT TCGAAC GCTAGA

9541 GCCTGT TTTGCA CGTTCA CCGCA TCAACG TTTTCT TTTCGG ATCCGC CGCATA ACCAGT

9601 GAAACA GCATTG CTGTCA CTTGGT CGTGGC AGCCCG GACCGA CGATGA AGCATG TTTAGC

9661 TGGCCC AAATGT TGCTGG ATAGTT TTTACT GCCAGA CCGCGC GCCTGA AGATAT AGAAGA

9721 TAATCG CGAACA TCTTCA GGTTCT GCGGGA AACCAT TTCCGG TTATTC AACTTG CACCAT

9781 GCCGCC CACGAC CGGCAA ACGGAC AGAAGC ATTTTC CAGGTA TGCTCA GAAAAC GCCTGG

9841 CGATCC CTGAAC ATGTCC ATCAGG TTCTTG CGAACC TCATCA CTCGTT GCATCG ACCGGT

9901 AATGCA GGCAAA TTTTGG TGTACG GTCAGT AAATTG ACACC TTCCTC TTCTTC TTGGGC

9961 ATGGCC GCAGGA AAGCAG AGCCCT GAAGCT CCCATC ACCGGC CAATAA GAGCCA AGCCTG

10021 CAGTGT GACCTC ATAGAG CAATGT GCCAGC CAGCCT GACCCC AAGGGC CCTCAG GCTTGG

10081 GCACAC TGTCTC TAGGAC CCTGAG AGAAAG ACATAC CCATTT CTGCTT AGGGCC CTGAGG

10141 ATGAGC CCAGGG GTGGCT TGGCAC TGAAGC AAAGGA CACTGG GGCTCA GCTGGC AGCAAA

10201 GTGACC AGGATG CTGAGG CTTTGA CCCAGA AGCCAG AGGCCA GAGGCC AGGACT TCTCTT

10261 GGTCCC AGTCCA CCCTCA CTCAGA GCTTTA CCAATG CCCTCT GGATAG TTGTCG GGTAAC

10321 GGTGGA CGCCAC TGATTC TCTGGC CAGCCT AGGACT TCGCCA TTCCGC TGATTC TGCTCT

10381 TCCAGC CACTGG CTGACC GGTTGG AAGTAC TCCAGC AGTGCC TTGGCA TCCAGG GCATCT

10441 GAGCCT ACCAGG TCCTTC AGTACC TCCTGC CAGGGC CTGGAG CAGCCA GCCTGC AACACC

10501 TGCCTG CCAAGC AGAGTG ACCACT GTGGGC ACAGGG GACACA GGGTGG GGCCCA ACACAG

10561 CACCAT TGTCCA CTTGTC CCTCAC TAGTAA AAGAAC TCTAGG GTTGCG GGGGGT GGGGGA

10621 GGTCTC TGTGAG GCTGGT AAGGGA TATTTG CCTGGC CCATGG AGCTAG CTTGGC TGGACG

10681 TAAACT CCTCTT CAGACC TAATAA CTTCGT ATAGCA TACATT ATACGA AGTTAT ATTAAG

10741 GGTTAT TGAATA TGATCG GAATTG GCTGC AGGAAT TCGATA GCTTGG CTGCAG GTCGAC

10801 GTACGT AGCAAG CTTGAT GGGCCC TGGTAC CACAGC CTGGGC AACACA GCAAAA ATCCCT

10861 TCCCTT AAAAAA AACAAA AGAGAA GGAAGA AGGACG AAGTAG AATGTG GAGGAC AAACAG

10921 GGGAGA GAGGGG GAAAGA AAGGGA GGGAAT TGTCTT AGAGTT TTACGG CTGTGC ACAGAC

10981 ACCATG ATCAAG GTAACT CTTGTA AGGATA ACATTT AGTTGG GGCTGG CTTACA GGTTCA

11041 GAAGTT CAGTCC ATTATC ATCAAG GCAGGA ACATGG CAGCAT TCAAGG CAGACA TGGTGC

11101 AGGAGG AGCTGA GAGTTC TACATC TTCATC TGAAGA TTTCTA GTAGAA TACTGG CTTCCA

11161 GGCAGC TAGGAT GAGGGT CTTAAA GCCCAC ACCCAG TGACAC ACCTAC TCCAAC AGGGCC

11221 ACACCT CCTAAT CATGCC ACTCCC TGGGCT GAGCAT ATAGAA ACCATC ACAGAG TCTAAC

11281 TAGTGT GGCCCA TCCTGC ACCCAT GGAAGA CCATCA CTGGGG CATAGA CAACCT CCAGAG

11341 CCCACC CTGACA GTTCCT GTCTCT GCCTTC TCCAGC AGTCAC CAGTTT CAAATA GCTCCT

11401 CAAGGA CAGATG GGGCCT TGTGAG CTTCAC CCCGCT GCAGGC TGGAAT GCGCCA CCTTTA

11461 ATCCCA GCACTT GGAAGG CAGAGG CAGGCA GATTTC TGAGTT CGAGGC CAGCCT AGTCTA

11521 CAGAGT GAGTTC CAGGAC AGCCAG GGCGAT ACAGAG AAACCC TGTCTC AAAAAA CAAAAC
```

-continued

```
11581 AAAACA AAACGA TAGAAA AGAGCA AAGTGA CCTTGG GCTATG GATGGG ATGGAC CATCGG

11641 GCACTG GGTTGG GAAGCT GAACTG GTCCAG ATGCCC AGAGCC CAGAGC TCTCTC CTCAGC

11701 AGTTCA TAACCT GGGGTG TTGCCA CAGCAC ACACAG CAAGGT TAGTTC TGCTGG TTGTCG

11761 GGACTT AGGGTA GGAGGA GTAGAA GCCTGC TACTGA TTCTGT CTCTCT CTGTTT CTCTCT

11821 CCTCCC TCCCTC CCTCCT TCCCTC CCTCCC TCCCTC TTCTTC TTCTTC TCATCC TCCTCC

11881 CTCTTC CTCTTC TTCCTC CACCTC CCCACC CCTTAT TTTGAT ACAGGG TTTCTC TGTGTA

11941 TCCCTG GCTGTC CTGGAA CTCACT CTGTAG CCCAGG TGGGCC TCGAAC TCTCAG CCTCAG

12001 TCCCCA GAATGC TGAGAA CACAGG TCTGAG TGATCA CTGATG GCTAAA AGTTGG GATTAC

12061 ATTGTT GTTGCT TGTTTG TTTATT CTTTTG TACATG GGACCC AAATAC AAATAG TAGCCT

12121 CAACAA TAAACA CGGGAT AAGTTG CTGCTC TGCTTT AGGGTC TCCCTG ACCTCT GTTTTT

12181 TTGTTT TTTGTT TTTGGT ATGTTT TGTTTT CTGTTG TTGTTG TTATCA TGTCTA TAAATC

12241 TATCTT CCTTCC TCCCTC CTTCCT TCCCTT CCTACT TCCCTC TCTTTC TTCATC CCTCCC

12301 TTCCCC CTACTC TCTTTC ACCCCC AGATAG GAAGCA AGCATG ATAAAA ACGTGT GGTGTT

12361 TTCCTT TTTATG TAGAGA GTACTG TGTAGT GAGTGT TATCCT ATGGGT GCTGCC ATTCTG

12421 CTGTAT GTTACC TGCTGT ATGTTA TACCAA CCTAGA TGGTGG TGAACT CACATG GTTGCT

12481 TCCATC TTGGTG AGGTTA CCAGCC AAGATG TCTGCC CTCCAC ATGATT GCCTCC ATCTTG

12541 GTGAGG TAAATG TTTAAT AAAGTA ACAAAA CAAGAC ATTAAA AACAAA CATTCC AGCACA

12601 AAATCT TCTTGA GATTAG AGACAT AATAGG AAGTCA GGTGAG GTCATA CAGGCC ATTAAT

12661 CCCATC ACTTGG GGAACA GAGGCA GGTAGA ACTTTG AATTGA AGGCAG GTATAT TTAGTG

12721 ATTTCC AGGGCT ATGTAG AGAGGC CCCTGA CCCAAC TAATAA GTAAAC AGGAAG ATAAAT

12781 AAATAT AATGAA CTTAGA ATAAAA CAAAGA AAGGAA GAAACA AGGGAA GGCAGT GCTGGG

12841 GGCCTG GCTTAT GGTGGA TGGGGG AATTCT GTGCTA GGGTGC CTGAAA CTCTGG GCTCCA

12901 TCCTCT GTAGTG CATAAA CTCTTT GGTACG TTAGCC CCTGTC TGTAAC AAGGAG CTGTCC

12961 ACGGTT GCAGTA CTGCCT TTCCCA TCTCAG CTGCCC CTCAGG AGCTGT CCACAG TGGCGA

13021 CACTTT TTCATC CTCAGC CTACAG CTTTAG GGAAAC ACCACT GCAGGG GCTGTC CCAAAG

13081 GTGCTG TCCACA GAGGCA GCACCT TCTCTG TGGTCT CACCCC TCCAGA CACCCC CCAGCA

13141 GCCCCA CAGGGA TGGCAC CTCAGT AAAAGC CAACTG TGGCCA GAGAAG TCTTCC TACCCT

13201 AACTCA TAGACT CGATGC AGGGAA AACAGG GTGAAA AAAAGC CACCAA GCCCTG AGCTCC

13261 CCCCAG CTCAGG ACTTAA AATCTC ATCAAT CCTCAC TATGGA AATCTC TGCCTT GAGAAG

13321 CTCTGC CCCCTC ATAAAT CCTATA TAAGAA CTGTCC CTTTGT CCAGTT CCCTGC CATCCG

13381 CTCCCA GGAGCA GAGGGC AGTTAT CCCTGG ATTCAT CCCTCC ACACCC TGGACC TGCCAA

13441 TAAACC TTTCTT GAGATT TCATGC TTCCTG TGATTC TCAGTG GAAGAA GCCAAG AAGAAA

13501 AGAACC AAAGAG AGGGAG CCAGGC TGAGGC TCCTGA GTTCTT CAGCTC AGCTGT GGATAC

13561 CTGTGA TGGTTT GTATAT GCTCTG TCCAGG GAATGG CATGAT TAGAAG GTGTGG CCCTGT

13621 TGAAGT AGGTGT GTCACT GTGGGT GTGGGC TATAAG ACCCTC ATCTTA ACTGCA TGGAAG

13681 TCATTC TTCCAC TGGCAG CCTTCA GATGAA AATGTA GAACTC TCAGCT CCTCCT GCACCA

13741 TGCCTG CCTAGA TGCTGC CCTGCT CCCACC TTGATG ATAATG GACTGA ACCTCT GAACCT

13801 GTAAGC CAGCCC CAATTA AATGTT GTTCTT TATAAG TCTTGC CTTGGT TGTGGT GTCTGT

13861 TCACAG CAGTAA AACCAT GACTAA GACAAT ATCTTC TACTTG GAGCTG CAACAA CTCTGC

13921 TGAGGA GGCTTC CTCTCA GAGCTA TATGGT TCCTGG TATCTG TAAAAT TCCCTT CTATTG
```

-continued

```
13981 GGACAC TTTCCA ACCTCA GATCTG TGTGGT TCCTGG CCCCTG TGTCTC GGGATG CCCTTC

14041 CATTAG AACAGC TTCTCC CCTCAG AGCTGC ATGGTT CCTGGA CTTCTG AGTCCC AGGAGA

14101 CCCTTC CATCTG AGCAGA AACACT TACAGG AGCAGA GTCCTC AACACC ACGGT TTTGTT

14161 TTGAAA GACCAA GACCAA CCCTCA GGAGGT TTCTGG CAAAGG CAGATT CTAGGT GCACCT

14221 GGAGGA GACCTA TAGTGC AGGACC ATCCGT CGTAGG TTGCTA GGCACC AATGGG CAAAGG

14281 TAGGGA AGAAAT CTTACC AGAAGA TTCTAT TCCATT CCATTC TCCTCA CAATGT AAGAGC

14341 CAAAGT TAACCT CTAAGG CCCAAG AACAAG GTAACT CTCCAG AATGCT GGGAGA TGTAGT

14401 TCTTGG GTAACA CAAGC CATGTT CTCGCC CTAAAC AAGTTT GTTTGA ATCAAC TACACT

14461 GAATGT ACTTGA TCATAT GTAGGA GAGAGA AGATTG ATTCTA GTTCAG GGTTTC AGGCTA

14521 TTTCAG TCCACC ATGATG GGAAAG GCATGA CATTGT TTATGA CAGTAA GAGCAT GTAGCA

14581 GAGGAT CCTCAC ATCACA ACAGGC CGAAAT GCAGAG GACAGT GCAACC AGAGGA CAGTCT

14641 GTAACT TTCCAA GTCCCT CTTCTA GTGGGT TGCTTC CACCAC CTCTCA GGTGGT GCTACA

14701 GCTCAG GAACAA TTGAGA TGTGTG ATGAAG GGCAGG TACTCA ACTGTG GCTGTA TTGTAT

14761 CCTTTT ATAGTT GTCCTC TGTGTG TTGAGC TATGTG CGAGAT TCTCAG GTCATC GGAGTA

14821 CCTGTT TTACTT TGGCAG GCATAG GAGACT CCTGAG AACTCT GCCTGA CATCCT TGCCAG

14881 CCCAAG CTTTGG TTTAGT GTGTGC AGTATC ACTCTT GGGTCT TATCTG CATATC CCTGAT

14941 GGCCCA TCAAGA TGTGTG CGGCCG CGTACC AGCTTT GTTCC CTTTAG TGAGGG TTAATT

15001 TCGAGC TTGGCG TAATCA TGGTCA TAGCTG TTTCCT GTGTGA AATTGT TATCCG CTCACA

15061 ATTCCA CACAAC ATACGA GCCGGA AGCATA AAGTGT AAAGCC TGGGGT GCCTAA TGAGTG

15121 AGCTAA CTCACA TTAATT GCGTTG CGCTCA CTGCCC GCTTTC CAGTCG GGAAAC CTGTCG

15181 TGCCAG CTGCAT TAATGA ATCGGC CAACGC GCGGGG AGAGGC GGTTTG CGTATT GGGCGC

15241 TCTTCC GCTTCC TCGCTC ACTGAC TCGCTG CGCTCG GTCGTT CGGCTG CGGCGA GCGGTA

15301 TCAGCT CACTCA AAGGCG GTAATA CGGTTA TCCACA GAATCA GGGGAT AACGCA GGAAAG

15361 AACATG TGAGCA AAAGGC CAGCAA AAGGCC AGGAAC CGTAAA AAGGCC GCGTTG CTGGCG

15421 TTTTTC CATAGG CTCCGC CCCCCT GACGAG CATCAC AAAAAT CGACGC TCAAGT CAGAGG

15481 TGGCGA AACCCG ACAGGA CTATAA AGATAC CAGGCG TTTCCC CCTGGA AGCTCC CTCGTG

15541 CGCTCT CCTGTT CCGACC CTGCCG CTTACC GGATAC CTGTCC GCCTTT CTCCCT TCGGGA

15601 AGCGTG GCGCTT TCTCAT AGCTCA CGCTGT AGGTAT CTCAGT TCGGTG TAGGTC GTTCGC

15661 TCCAAG CTGGGC TGTGTG CACGAA CCCCCC GTTCAG CCCGAC CGCTGC GCCTTA TCCGGT

15721 AACTAT CGTCTT GAGTCC AACCCG GTAAGA CACGAC TTATCG CCACTG GCAGCA GCCACT

15781 GGTAAC AGGATT AGCAGA GCGAGG TATGTA GGCGGT GCTACA GAGTTC TTGAAG TGGTGG

15841 CCTAAC TACGGC TACACT AGAAGA ACAGTA TTTGGT ATCTGC GCTCTG CTGAAG CCAGTT

15901 ACCTTC GGAAAA AGAGTT GGTAGC TCTTGA TCCGGC AAACAA ACCACC GCTGGT AGCGGT

15961 GGTTTT TTTGTT TGCAAG CAGCAG ATTACG CGCAGA AAAAAA GGATCT CAAGAA GATCCT

16021 TTGATC TTTTCT ACGGGG TCTGAC GCTCAG TGGAAC GAAAAC TCACGT TAAGGG ATTTTG

16081 GTCATG AGATTA TCAAAA AGGATC TTCACC TAGATC CTTTTA AATTAA AAATGA AGTTTT

16141 AAATCA ATCTAA AGTATA TATGAG TAAACT TGGTCT GACAGT TACCAA TGCTTA ATCAGT

16201 GAGGCA CCTATC TCAGCG ATCTGT CTATTT CGTTCA TCCATA GTTGCC TGACTC CCCGTC

16261 GTGTAG ATAACT ACGATA CGGGAG GGCTTA CCATCT GGCCCC AGTGCT GCAATG ATACCG

16321 CGAGAC CCACGC TCACCG GCTCCA GATTTA TCAGCA ATAAAC CAGCCA GCCGGA AGGGCC

16381 GAGCGC AGAAGT GGTCCT GCAACT TTATCC GCCTCC ATCCAG TCTATT AATTGT TGCCGG
```

```
16441 GAAGCT AGAGTA AGTAGT TCGCCA GTTAAT AGTTTG CGCAAC GTTGTT GCCATT GCTACA
16501 GGCATC GTGGTG TCACGC TCGTCG TTTGGT ATGGCT TCATTC AGCTCC GGTTCC CAACGA
16561 TCAAGG CGAGTT ACATGA TCCCCC ATGTTG TGCAAA AAAGCG GTTAGC TCCTTC GGTCCT
16621 CCGATC GTTGTC AGAAGT AAGTTG GCCGCA GTGTTA TCACTC ATGGTT ATGGCA GCACTG
16681 CATAAT TCTCTT ACTGTC ATGCCA TCCGTA AGATGC TTTTCT GTGACT GGTGAG TACTCA
16741 ACCAAG TCATTC TGAGAA TAGTGT ATGCGG CGACCG AGTTGC TCTTGC CCGGCG TCAATA
16801 CGGGAT AATACC GCGCCA CATAGC AGAACT TTAAAA GTGCTC ATCATT GGAAAA CGTTCT
16861 TCGGGG CGAAAA CTCTCA AGGATC TTACCG CTGTTG AGATCC AGTTCG ATGTAA CCCACT
16921 CGTGCA CCCAAC TGATCT TCAGCA TCTTTT ACTTTC ACCAGC GTTTCT GGGTGA GCAAAA
16981 ACAGGA AGGCAA AATGCC GCAAAA AAGGGA ATAAGG GCGACA CGGAAA TGTTGA ATACTC
17041 ATACTC TTCCTT TTTCAA TATTAT TGAAGC ATTTAT CAGGGT TATTGT CTCATG AGCGGA
17101 TACATA TTTGAA TGTATT TAGAAA AATAAA CAAATA GGGGTT CCGCGC ACATTT CCCCGA
17161 AAAGTG CCACCT GACGCG CCCTGT AGCGGC GCATTA AGCGCG GCGGGT GTGGTG GTTACG
17221 CGCAGC GTGACC GCTACA CTTGCC AGCGCC CTAGCG CCCGCT CCTTTC GCTTTC TTCCCT
17281 TCCTTT CTCGCC ACGTTC GCCGGC TTTCCC CGTCAA GCTCTA AATCGG GGCTC CCTTTA
17341 GGGTTC CGATTT AGTGCT TTACGG CACCTC GACCCC AAAAAA CTTGAT TAGGGT GATGGT
17401 TCACGT AGTGGG CCATCG CCCTGA TAGACG GTTTTT CGCCCT TTGACG TTGGAG TCCACG
17461 TTCTTT AATAGT GGACTC TTGTTC CAAACT GGAACA ACACTC AACCCT ATCTCG GTCTAT
17521 TCTTTT GATTTA TAAGGG ATTTTG CCGATT TCGGCC TATTGG TTAAAA AATGAG CTGATT
17581 TAACAA AAATTT AACGCG AATTTT AACAAA ATATTA A
```

In SEQ ID NO:1 the solid underlined portions represent the homology arms. The portions of the homology arms shown with a doublesolidunderline correspond to untranslated regions (UTRs), more specifically the 5' UTR that is part of exon 2 of mouse Protein C and the 3' UTR that is part of exon 9 of mouse Protein C. The portion shown in bold italics represents the nucleotide sequence coding for human Protein C. The dashed underline portions represent loxP sites.

5' homology arm of targeting vector
SEQ ID NO: 2
TCCCTGCACAGCTAGTCACAACGAAGGAAGGCGCTTAGGGAACCCTGGCAGCTTGCAAAACGCAAAGGGCTACGGCTGCATCGCT
CTTTTCCAGACTTCTCAGCTGGGAGCTTCTGGCAGTTTTCCCGAGTCACTCCTTTCTCTCACTAGCTCACAAAGTGGCCAGCTGA
GTCAGAAGCCTCCTTCTAGTACAGGCCTGCCTCCCACCAACGCCATCAATCAGGACAAGTAAGGAAGACTTCTGAGTCGCCCCCC
CCCCCCACCGGTCAAATAGAGGGGACATCTTATCACTGATGGCATCCTAGATTGGTGATATATGTAATTATTTTTGAGTGTGCTA
CCCACGAACAAGCTATATCTGTTTATGGTTGCTGTTGTTTTGGTTTTTGTTTTCTTTTAAGGTTCTCATCCCTCAGCCACTGCGG
GCAAAAATGAGACCACATTTGCCAATAAGTTTGAACACGCTCAACCCTCTCTTTCTCCCTCCCTTTCTGATAGACAATTCCTTCG
GTAGGCAGAGGTGAGCAATGGGCACACGGAGCCTTCCAGAGCTGGGATCAGAAAACCTCTTGTTTGTTTGTCTGGGGAGAGGGAG
GTTCGGCACCAAGGGCTAAGCAAATATTTGCGGTTATGGATTAACCTGACTCCCAGACTGACATGGCGCTACCTGGACGAAATTG
CAGTTTCTCCTTGGCCCACGCCTGTAAGTCCCCCTCATTGCAAGACTGTGAAGGACTGTGGAGGGAGGGGAGGGGAGGAAAGTCC
AGCTGGGAGGAAGGTGACGTTCTTGAGCTAAGGCTCTCCAGGCAGACTGAAATGTGGGCCAAGGAAAATGAGCGCCCAAACTCT
ATCTGGACCAAGGCGTGGGTTCCCTACAATCCAGGTGACCATCTCGACACATGAGATTTTGTGGATCAAGTGGACAGCAGTCAAA
GGGTTCCCTATGATCAGGAACCATCCTCAGAGCAATCTTGAAACCCAGAACCCCACTACTCCCCTCTGCCCTGTTCTCTAAGGTG
GACTCTACAATTCCGGAAGCCAGCAAAGCCGAAGAGTGAGGCCAGGAGGGGCTGTGCAGCTGGGATAGGCGGGCCTGCCCACCTG
GTCTGGGGGACACTAGAGGCCTTGTGGTTTGACTACTGGTTGGGGGCAGGGGTTAAGGTTCCAGAGTTGGGGCCACATAGGCTTG
GCCTTGAAGCCAAACTCTGCCCTCCTCTTAGGTGTAGGCTTGTGACAAGCCGCGTATCTCCTCCAAGCCTTTGGGTCCCTTCCCA -continued

TGAAATGGAGGTGAGAATATTCATGCCTTCCTCTTTTAACAGTGATCAGTGTGTGTGTGTGTGTGTGTGTGTGTGTGTG

TGTGTGTGTGTGTGTGTGGTGTAGAGTGTGGTTTCTGGTGTTCAGGGTTGAACCCAGAATCTTAAACATGCCAAGTACGTTCT

TTCCTACTGAACTGCAACCCTCCAGTATCCTGTACTTGTTGTTTGTTTGTTTGTTTGTTTGTTCGGAAGCACCTGTGGTGG

CACACACTTACAATCCTAGTGCTAGAGAGCAGAAACAAGTGGATCCCTTGGGCTTGCTGGCTGGCCAGCCTACGTGATGAGTTTC

AGGCAGTGAGAGACCTTGTCCCAAACAATAAGGTGGAAGTAAGCCATGATGGCATACCCCTTTAGAGCTAGTACTCGAGAGGCAG

AAGCAGGTGGAGTTTAAGACCAGCCTGGTCTACATAGAAGTTCCAGGATAGCCAAAAAGTACCCAAGGCCATCCAAAAAAACAAA

AACAAAACAAAACCTGGAGGGAAAAAAAAAACCAGACAATGCCTGGGGAAGGATGAAGGACAGTCAGTCAGATTATCCCTGGTCA

ACACGTGTGCACAAATCTGTGCACACAAGAAAGAGCTTCACATGGGTTACTATTTGTTTTCCAACAACTCATTTTTAAGCCCCCA

CTCTCTTTCTCTGTTTTTAAAAAAGGTTTATTTATTTTATGTATATGAGTACATTATTGCTCTCTTCAGACACACCAGAAAAGGA

CATAAGATTCCATTACAGATGGTTGTGAGCCACCATGTGGTTGCTGGAATTTGAACTCAGGTCCTCTGGAAGAGCAGTCGGTGCT

CTTAACCACTGAACCATCTCCCCAGCCCTTCCAACAACTCTTTATGGAAGAAACCTATTCTATCCATTTTATAAATGACAGAACT

GAGGCACGGAGCACGTAAACATCTTGTTAAATACCTCTCTCTCTCTCTCTCCCCAGTAGGAAATGGAATTTGCCCCAGGCA

ATGACTTTTTTTTTTTTTTTTGCTTTCATGTACCTAGAGTAAGCCCAGCTCTAAAGGCCACGAGATTGTCTGTCTGTGGACCG

TGGTGTACCCCACTCCCAGACCCAGCTTCCACACAGACAATGAGCTCACAAACGTCCTTTACTCCCTTCCTTCCTTGCTTGCTCT

GTGTGTGTGTGTGTGTGTGTGTGTTAAGAGATCAACCTCAGACATTTTCTTTAGGAGCTATTTACCTTGCTTTTTGAGACAGG

GCCTCCGGATGGCCTGGAGCTAGTCACCTGGAGCTGGTCAAGCAGGCTAGGGTGGCTGGCCTAAGCAATCCACAGGATCTGCTTA

TCTCTGCCTCCCCAGTCCTGGGATTACAAGAAACGCCTCAGACACCTAGATTTCTGTTTTAATTTTCTATGGGTTCTGGGGATCT

TTCTTAAGTCTTCAAGTATGCACGGAAAGGGCTTTATTGACTAAGATATCTCCCCTGCTCAGGAATGGCCCTTTCATTCTACTTT

GGAGGGAGCTGGGGGTGGGGCGGGGAGCAGCTCAGCTGTGTGTATCCTTGGAGCTTAGAAGTTCTCCTCAGACAGGTGTCAGCAG

CTCCAGG

First part of (i.e. 5' portion of) 3' homology arm of targeting vector
SEQ ID NO: 3
CACCCCTCCCTGCTCACCTCTGGACCCTAGAAGTCACTCTTGGAGTAAGGCTGGGCTAGTGAGTACCAAGACAGAGGACATTAAA GGAGCATGCAACAAACATACCTCCCCGAGTACCTGTCTGTCTTTTCATCCTTTTTATGGGCTATTCTGGGGGAAAGTAACATTAA TTGAGCATGCACTACACACCAAGTCTATGAAAAGAACCTGCTTAACTCCCAAAGCAGTTGTGTAGAAGATCTAGTGGGATCTGAG CTGATATCACTTCTGGGGGTGAGTGGAGGAGATTGATTTAGAGAAAGGAATTTTTTTAGAAGTTACTGTAAGAGACTAATAGAGC CTTTCTCAGGGCCTTGGAAAGAGCCCGTGCTAGTTACATCAGAAAAGCTTGCCAGTGACCAGTGGCCAGTGAGACTCAGAATGGC CATGTGGTGGAGCCAGGATTCAAACCAAGGTCACACTCCCAAACTCAGCTGCTTCTCTTCTTTATTATCCCTGGGTGTGTGCTGG TGTGTGTGTGCGCGCGTGGGTGTGTGGGTGGATACATGCATGTGTGTGTGTGTGTGTGTGTGTGTGTGTGTGTTATATGTT TGGAGACCAGAGGACAACTTCGTTTCTCAACACCATCCACTTGTTTTGTTTTGTGTTTTGTTTTGTTTGTTGACACAGGGTCTCT CACTGTCCTGAAATCTACCCAGTAGGCTAGGCTGGCTGGCTACCAAACCCCACCCCACCCTGGCTTTGACAAGTGGAGACAGAAG ACCAGTAGTCCACTGGAGATGTGACCAGATGCCCAGAAGGTGCTCCTCATGGTGCCCTACAGTTTTGTTGAGGAGTCTGTTTAAT

AATGCAGCTGGGTGCAGTGGCAGCACCTGTAGCCCCCAATACTGAGGCAGCATTGCTGCAGTCTGAGGTGGGG

Second part of (i.e. 3' portion of) 3' homology ar of targeting vector
SEQ ID NO: 4
ACAGCCTGGGCAACACAGCAAAAATCCCTTCCCTTAAAAAAAACAAAAGAGAAGGAAGAAGGACGAAGTAGAATGTGGAGGACAA ACAGGGGAGAGAGGGGAAAGAAAGGGAGGGAATTGTCTTAGAGTTTTACGGCTGTGCACAGACACCATGATCAAGGTAACTCTT GTAAGGATAACATTTAGTTGGGGCTGGCTTACAGGTTCAGAAGTTCAGTCCATTATCATCAAGGCAGGAACATGGCAGCATTCAA GGCAGACATGGTGCAGGAGGAGCTGAGAGTTCTACATCTTCATCTGAAGATTTCTAGTAGAATACTGGCTTCCAGGCAGCTAGGA TGAGGGTCTTAAAGCCCACACCCAGTGACACACCTACTCCAACAGGGCCACACCTCCTAATCATGCCACTCCCTGGGCTGAGCAT ATAGAAACCATCACAGAGTCTAACTAGTGTGGCCCATCCTGCACCCATGGAAGACCATCACTGGGGCATAGACAACCTCCAGAGC CCACCCTGACAGTTCCTGTCTCTGCCTTCTCCAGCAGTCACCAGTTTCAAATAGCTCCTCAAGGACAGATGGGGCCTTGTGAGCT TCACCCCGCTGCAGGCTGGAATGCGCCACCTTTAATCCCAGCACTTGGAAGGCAGAGGCAGGCAGATTTCTGAGTTCGAGGCCAG -continued

```
CCTAGTCTACAGAGTGAGTTCCAGGACAGCCAGGGGCGATACAGAGAAACCCTGTCTCAAAAAACAAAACAAAACAAAACGATAG

AAAAGAGCAAAGTGACCTTGGGCTATGGATGGGATGGACCATCGGGCACTGGGTTGGGAAGCTGAACTGGTCCAGATGCCCAGAG

CCCAGAGCTCTCTCCTCAGCAGTTCATAACCTGGGGTGTTGCCACAGCACACACAGCAAGGTTAGTTCTGCTGGTTGTCGGGACT

TAGGGTAGGAGGAGTAGAAGCCTGCTACTGATTCTGTCTCTCTGTTTCTCTCCTCCCTCCCTCCCTCCTTCCCTCCCTCCC

TCCCTCTTCTTCTTCTTCTCATCCTCCTCCCTCTTCCTCTTCTTCCTCCACCTCCCCACCCCTTATTTTGATACAGGGTTTCTCT

GTGTATCCCTGGCTGTCCTGGAACTCACTCTGTAGCCCAGGTGGGCCTCGAACTCTCAGCCTCAGTCCCCAGAATGCTGAGAACA

CAGGTCTGAGTGATCACTGATGGCTAAAAGTTGGGATTACATTGTTGTTGCTTGTTTGTTTATTCTTTTGTACATGGGACCCAAA

TACAAATAGTAGCCTCAACAATAAACACGGGATAAGTTGCTGCTCTGCTTTAGGGTCTCCCTGACCTCTGTTTTTTGTTTTTTG

TTTTTGGTATGTTTTGTTTTCTGTTGTTGTTGTTATCATGTCTATAAATCTATCTTCCTTCCTCCCTCCTTCCTTCCCTTCCTAC

TTCCCTCTCTTTCTTCATCCCTCCCTTCCCCCTACTCTCTTTCACCCCCAGATAGGAAGCAAGCATGATAAAAACGTGTGGTGTT

TTCCTTTTTATGTAGAGAGTACTGTGTAGTGAGTGTTATCCTATGGGTGCTGCCATTCTGCTGTATGTTACCTGCTGTATGTTAT

ACCAACCTAGATGGTGGTGAACTCACATGGTTGCTTCCATCTTGGTGAGGTTACCAGCCAAGATGTCTGCCCTCCACATGATTGC

CTCCATCTTGGTGAGGTAAATGTTTAATAAAGTAACAAAACAAGACATTAAAAACAAACATTCCAGCACAAAATCTTCTTGAGAT

TAGAGACATAATAGGAAGTCAGGTGAGGTCATACAGGCCATTAATCCCATCACTTGGGGAACAGAGGCAGGTAGAACTTTGAATT

GAAGGCAGGTATATTTAGTGATTTCCAGGGCTATGTAGAGGCCCCTGACCCAACTAATAAGTAAACAGGAAGATAAATAAATATA

ATGAACTTAGAATAAAACAAAGAAAGGAAGAAACAAGGGAAGGCAGTGCTGGGGCCTGGCTTATGGTGGATGGGGGAATTCTGT

GCTAGGGTGCCTGAAACTCTGGGCTCCATCCTCTGTAGTGCATAAACTCTTTGGTACGTTAGCCCCTGTCTGTAACAAGGAGCTG

TCCACGGTTGCAGTACTGCCTTTCCCATCTCAGCTGCCCCTCAGGAGCTGTCCACAGTGGCGACACTTTTTCATCCTCAGCCTAC

AGCTTTAGGGAAACACCACTGCAGGGGCTGTCCCAAAGGTGCTGTCCACAGAGGCAGCACCTTCTCTGTGGTCTCACCCCTCCAG

ACACCCCCCAGCAGCCCCACAGGGATGGCACCTCAGTAAAAGCCAACTGTGGCCAGAGAAGTCTTCCTACCCTAACTCATAGACT

CGATGCAGGGAAAACAGGGTGAAAAAAAGCCACCAAGCCCTGAGCTCCCCCAGCTCAGGACTTAAAATCTCATCAATCCTCACT

ATGGAAATCTCTGCCTTGAGAAGCTCTGCCCCCTCATAAATCCTATATAAGAACTGTCCCTTTGTCCAGTTCCCTGCCATCCGCT

CCCAGGAGCAGAGGGCAGTTATCCCTGGATTCATCCCTCCACACCCTGGACCTGCCAATAAACCTTTCTTGAGATTTCATGCTTC

CTGTGATTCTCAGTGGAAGAAGCCAAGAAGAAAAGAACCAAAGAGAGGGAGCCAGGCTGAGGCTCCTGAGTTCTTCAGCTCAGCT

GTGGATACCTGTGATGGTTTGTATATGCTCTGTCCAGGGAATGGCATGATTAGAAGGTGTGGCCCTGTTGAAGTAGGTGTGTCAC

TGTGGGTGTGGGCTATAAGACCCTCATCTTAACTGCATGGAAGTCATTCTTCCACTGGCAGCCTTCAGATGAAAATGTAGAACTC

TCAGCTCCTCCTGCACCATGCCTGCCTAGATGCTGCCCTGCTCCCACCTTGATGATAATGGACTGAACCTCTGAACCTGTAAGCC

AGCCCCAATTAAATGTTGTTCTTTATAAGTCTTGCCTTGGTTGTGGTGTCTGTTCACAGCAGTAAAACCATGACTAAGACAATAT

CTTCTACTTGGAGCTGCAACAACTCTGCTGAGGAGGCTTCCTCTCAGAGCTATATGGTTCCTGGTATCTGTAAAATTCCCTTCTA

TTGGGGACACTTTCCAACCTCAGATCTGTGTGGTTCCTGGCCCCTGTGTCTCGGGATGCCCTTCCATTAGAACAGCTTCTCCCCT

CAGAGCTGCATGGTTCCTGGACTTCTGAGTCCCAGGAGACCCTTCCATCTGAGCAGAAACACTTACAGGAGCAGAGTCCTCCAAC

ACCACGGTTTTGTTTTGAAAGACCAAGACCAACCCTCAGGAGGTTTCTGGCAAAGGCAGATTCTAGGTGCACCTGGAGGAGACCT

ATAGTGCAGGACCATCCGTCGTAGGTTGCTAGGCACCAATGGGCAAAGGTAGGGAAGAAATCTTACCAGAAGATTCTATTCCATT

CCATTCTCCTCACAATGTAAGAGCCAAAGTTAACCTCTAAGGCCCAAGAACAAGGTAACTCTCCAGAATGCTGGGAGATGTAGTT

CTTGGGTAACAACAAGCCATGTTCTCGCCCTAAACAAGTTTGTTTGAATCAACTACACTGAATGTACTTGATCATATGTAGGAGA

GAGAAGATTGATTCTAGTTCAGGGTTTCAGGCTATTTCAGTCCACCATGATGGGAAAGGCATGACATTGTTTATGACAGTAAGAG

CATGTAGCAGAGGATCCTCACATCACAACAGGCCGAAATGCAGAGGACAGTGCAACCAGAGGACAGTCTGTAACTTTCCAAGTCC

CTCTTCTAGTGGGTTGCTTCCACCACCTCTCAGGTGGTGCTACAGCTCAGGAACAATTGAGATGTGTGATGAAGGGCAGGTACTC
```

```
AACTGTGCTGTATTGTATCCTTTTATAGTTGTCCTCTGTGTGTTGAGCTATGTGCGAGATTCTCAGGTCATCGGAGTACCTGTTT

TACTTTGGCAGGCATAGGAGACTCCTGAGAACTCTGCCTGACATCCTTGCCAGCCCAAGCTTTGGTTTAGTGTGTGCAGTATCAC

TCTTGGGTCTTATCTGCATATCCCTGATGGCCCATCAAGATGTGT
```

UTR sequence in exon 2 of mouse Protein C

SEQ ID NO: 5

```
ACAGGTGTCAGCAGCTCCAGG
```

UTR sequence in exon 9 of mouse Protein C

SEQ ID NO: 6

```
CACCCCTCCCTGCTCACCTCTGGACCCTAGAAGTCACTCTTGGAGTAAGGCTGGGCTAGTGAGTACCAAGACAGAGGACATTAAA

GGAGCATGCAACAAACATA
``` human Protein C coding sequence (Human PROC CDS)

SEQ ID NO: 8

```
ATGTGGCAGCTCACAAGCCTCCTGCTGTTCGTGGCCACCTGGGGAATTTCCGGCACACCAGCTCCTCTTGACTCAGTGTTCTCCA

GCAGCGAGCGTGCCCACCAGGTGCTGCGGATCCGCAAACGTGCCAACTCCTTCCTGGAGGAGCTCCGTCACAGCAGCCTGGAGCG

GGAGTGCATAGAGGAGATCTGTGACTTCGAGGAGGCCAAGGAAATTTTCCAAAATGTGGATGACACACTGGCCTTCTGGTCCAAG

CACGTCGACGGTGACCAGTGCTTGGTCTTGCCCTTGGAGCACCCGTGCGCCAGCCTGTGCTGCGGGCACGGCACGTGCATCGACG

GCATCGGCAGCTTCAGCTGCGACTGCCGCAGCGGCTGGGAGGGCCGCTTCTGCCAGCGCGAGGTGAGCTTCCTCAATTGCTCGCT

GGACAACGGCGGCTGCACGCATTACTGCCTAGAGGGAGGTGGGCTGGCGGCGCTGTAGCTGTGCGCCTGGCTACAAGCTGGGGGA

CGACCTCCTGCAGTGTCACCCCGCAGTGAAGTTCCCTTGTGGGAGGCCCTGGAAGCGGATGGAGAAGAAGCGCAGTCACCTGAAA

CGAGACACAGAAGACCAAGAAGACCAAGTAGATCCGCGGCTCATTGATGGGAAGATGACCAGGCGGGGAGACAGCCCCTGGCAGG

TGGTCCTGCTGGACTCAAAAGAAGAAGCTGGCCTGCGGGGCAGTGCTCATCCACCCCTCCTGGGTGCTGACAGCGGCCCACTGCA

TGGATGAGTCCAAGAAGCTCCTTGTCAGGCTTGGAGAGTATGACCTGCGGCGCTGGGAGAAGTGGGAGCTGGACCTGGACATCAA

GGAGGTCTTCGTCCACCCCAACTACAGCAAGAGCACCACCGACAATGACATCGCACTGCTGCACCTGGCCCAGCCCCGCCACCCT

CTCGCAGACCATAGTGCCCATCTGCCTCCCGACAGCGGCCTTGCAGAGCGCGAGCTCAATCAGGCCGGCCAGGAGACCCTCGTG

ACGGGCTGGGGCTACCACAGCAGCCGAGAGAAGGAGGCCAAGAGAAACCGCACCTTCGTCCTCAACTTCATCAAGATTCCCGTGG

TCCCGCACAATGAGTGCAGCGAGGTCATGAGCAACATGGTGTCTGAGAACATGCTGTGTGCGGGCATCCTCGGGGACCGGCAGGA

TGCCTGCGAGGGCGACAGTGGGGGGCCCATGGTCGCCTCCTTCCACGGCACCTGGTTCCTGGTGGGCCTGGTGAGCTGGGGTGAG

GGCTGTGGGCTCCTTCACAACTACGGCGTTTACACCAAAGTCAGCCGCTACCTCGACTGGATCCATGGGCACATCAGAGACAAGG

AAGCCCCCCAGAAGAGCTGGGCACCTTAG
```

Section of targeting vector from the 5' end of the 5' homology arm to the 3' end of the 3' homology arm

SEQ ID NO: 9

```
TCCCTGCACAGCTAGTCACAACGAAGGAAGGCGCTTAGGGAACCCTGGCAGCTTGCAAAACGCAAAGGGCTACGGCTGCATCGCT

CTTTTCCAGACTTCTCAGCTGGGAGCTTCTGGCAGTTTTCCCGAGTCACTCCTTTCTCTCACTAGCTCACAAAGTGGCCAGCTGA

GTCAGAAGCCTCCTTCTAGTACAGGCCTGCCTCCCACCAACGCCATCAATCAGGACAAGTAAGGAAGACTTCTGAGTCGCCCCCC

CCCCCCACCGGTCAAATAGAGGGGACATCTTATCACTGATGGCATCCTAGATTGGTGATATATGTAATTATTTTTGAGTGTGCTA

CCCACGAACAAGCTATATCTGTTTATGGTTGCTGTTGTTTTGGTTTTTGTTTTCTTTTAAGGTTCTCATCCCTCAGCCACTGCGG

GCAAAATGAGACCACATTTGCCAATAAGTTTGAACACGCTCAACCCTCTCTTTCTCCCTCCCTTTCTGATAGACAATTCCTTCGG

TAGGCAGAGGTGAGCAATGGGCACACGGAGCCTTCCAGAGCTGGGATCAGAAAACCTCTTGTTTGTTTGTCTGGGGAGAGGGAGG

TTCGGCACCAAGGGCTAAGCAAATATTTGCGGTTATGGATTAACCTGACTCCCAGACTGACATGGCGCTACCTGGACGAAATTGC

AGTTTCTCCTTGGCCCACGCCTGTAAGTCCCCCTCATTGCAAGACTGTGAAGGACTGTGGAGGGAGGGGAGGGGAGGAAAGTCCA

GCTGGGAGGAAGGTGACGTTCTTGAGCTAAGGCTCTCCAGGCAGACTGAAATGTGGGGCAAGGAAAATGAGCGCCCAAACTCTA

TCTGGACCAAGGCGTGGGTTCCCTACAATCCAGGTGACCATCTCGACACATGAGATTTTGTGGATCAAGTGGACAGCAGTCAAAG

GGTTCCCTATGATCAGGAACCATCCTCAGAGCAATCTTGAAACCCAGAACCCCACTACTCCCCTCTGCCCTGTTCTCTAAGGTGG

ACTCTACAATTCCGGAAGCCAGCAAAGCCGAAGAGTGAGGCCAGGAGGGGCTGTGCAGCTGGGATAGGCGGGCCTGCCCACCTGG
```

```
TCTGGGGACACTAGAGGCCTTGTGGTTTGACTACTGGTTGGGGGCAGGGGTTAAGGTTCCAGAGTTGGGGCCACATAGGCTTGG
CTTGAAGCCAAACTCTGCCCTCCTCTTAGGTGTAGGCTTGTGACAAGCCGCGTATCTCCTCCAAGCCTTTGGGTCCCTTCCCATG
AAATGGAGGTGAGAATATTCATGCCTTCCTCTTTTAACAGTGATCAGTGTGTGTGTGTGTGTGTGTGTGTGTGTGTGTGTGTG
TGTGTGTGTGTGGTGTAGAGTGTGGTTTCTGGTGTTCAGGGTTGAACCCAGAATCTTAAACATGCCAAGTACGTTCTTTCCTA
CTGAACTGCAACCCTCCAGTATCCTGTACTTGTTGTTTGTTTGTTTGTTTGTTTGTTCGGAAGCACCTGTGGTGGCACACA
CTTACAATCCTAGTGCTAGAGAGCAGAAACAAGTGGATCCCTTGGGCTTGCTGGCTGGCCAGCCTACGTGATGAGTTTCAGGCAG
TGAGAGACCTTGTCCCAAACAATAAGGTGGAAGTAAGCCATGATGGCATACCCCTTTAGAGCTAGTACTCGAGAGGCAGAAGCAG
GTGGAGTTTAAGACCAGCCTGGTCTACATAGAAGTTCCAGGATAGCCAAAAAGTACCCAAGGCCATCCAAAAAAACAAAAACAAA
ACAAAACCTGGAGGGAAAAAAAAAACCAGACAATGCCTGGGGAAGGATGAAGGACAGTCAGTCAGATTATCCCTGGTCAACACGT
GTGCACAAATCTGTGCACACAAGAAAGAGCTTCACATGGGTTACTATTTGTTTTCCAACAACTCATTTTTAAGCCCCCACTCTCT
TTCTCTGTTTTTAAAAAAGGTTTATTTATTTTATGTATATGAGTACATTATTGCTCTCTTCAGACACACCAGAAAAGGACATAAG
ATTCCATTACAGATGGTTGTGAGCCACCATGTGGTTGCTGGAATTTGAACTCAGGTCCTCTGGAAGAGCAGTCGGTGCTCTTAAC
CACTGAACCATCTCCCCAGCCCTTCCAACAACTCTTTATGGAAGAAACCTATTCTATCCATTTTATAAATGACAGAACTGAGGCA
CGGAGCACGTAAACATCTTGTTAAATACCTCTCTCTCTCTCTCTCCCCAGTAGGAAATGGAATTTGCCCCAGGCAATGACTTT
TTTTTTTTTTTTTTGCTTTCATGTACCTAGAGTAAGCCCAGCTCTAAAGGCCACGAGATTGTCTGTCTGTGGACCGTGGTGTAC
CCCACTCCCAGACCCAGCTTCCACACAGACAATGAGCTCACAAACGTCCTTTACTCCCTTCCTTCCTTGCTTGCTCTGTGTGTGT
GTGTGTGTGTGTGTGTTAAGAGATCAACCTCAGACATTTTCTTTAGGAGCTATTTACCTTGCTTTTTGAGACAGGGCCTCC
GGATGGCCTGGAGCTAGTCACCTGGAGCTGGTCAAGCAGGCTAGGGTGGCTGGCCTAAGCAATCCACAGGATCTGCTTATCTCTG
CCTCCCCAGTCCTGGGATTACAAGAAACGCCTCAGACACCTAGATTTCTGTTTTAATTTTCTATGGGTTCTGGGGATCTTTCTTA
AGTCTTCAAGTATGCACGGAAAGGGCTTTATTGACTAAGATATCTCCCCTGCTCAGGAATGGCCCTTTCATTCTACTTTGGAGGG
AGCTGGGGGTGGGCGGGGAGCAGCTCAGCTGTGTGTATCCTTGGAGCTTAGAAGTTCTCCTCAGACAGGTGTCAGCAGCTCCAG
GATGTGGCAGCTCACAAGCCTCCTGCTGTTCGTGGCCACCTGGGGAATTTCCGGCACACCAGCTCCTCTTGACTCAGTGTTCTCC
AGCAGCGAGCGTGCCCACCAGGTGCTGCGGATCCGCAAACGTGCCAACTCCTTCCTGGAGGAGCTCCGTCACAGCAGCCTGGAGC
GGGAGTGCATAGAGGAGATCTGTGACTTCGAGGAGGCCAAGGAAATTTTCCAAAATGTGGATGACACACTGGCCTTCTGGTCCAA
GCACGTCGACGGTGACCAGTGCTTGGTCTTGCCCTTGGAGCACCCGTGCGCCAGCCTGTGCTGCGGGACACGGCACGTGCATCGAC
GGCATCGGCAGCTTCAGCTGCGACTGCCGCAGCGGCTGGGAGGGCCGCTTCTGCCAGCGCGAGGTGAGCTTCCTCAATTGCTCGC
TGGACAACGGCGGCTGCACGCATTACTGCCTAGAGGAGGTGGGCTGGCGGCGCTGTAGCTGTGCGCCTGGCTACAAGCTGGGGGA
CGACCTCCTGCAGTGTCACCCCGCAGTGAAGTTCCCTTGTGGGAGGCCCTGGAAGCGGATGGAGAAGAAGCGCAGTCACCTGAAA
CGAGACACAGAAGACCAAGAAGACCAAGTAGATCCGCGGCTCATTGATGGGAAGATGACCAGGCGGGGAGACAGCCCCTGGCAGG
TGGTCCTGCTGGACTCAAAGAAGAAGCTGGCCTGCGGGGCAGTGCTCATCCACCCCTCCTGGGTGCTGACAGCGGCCCACTGCAT
GGATGAGTCCAAGAAGCTCCTTGTCAGGCTTGGAGAGTATGACCTGCGGCGCTGGGAGAAGTGGGAGCTGGACCTGGACATCAAG
GAGGTCTTCGTCCACCCCAACTACAGCAAGAGCACCACCGACAATGACATCGACACTGCTGCACCTGGCCCAGCCCGCCACCCTC
TCGCAGACCATAGTGCCCATCTGCCTCCCGGACAGCGGCCTTGCAGAGCGCGAGCTCAATCAGGCCGGCCAGGAGACCCTCGTGA
CGGGCTGGGGCTACCACAGCAGCCGAGAGAAGGAGGCCAAGAGAAACCGCACCTTCGTCCTCAACTTCATCAAGATTCCCGTGGT
CCCGCACAATGAGTGCAGCGAGGTCATGAGCAACATGGTGTCTGAGAACATGCTGTGTGCGGGCATCCTCGGGGACCGGCAGGAT
GCCTGCGAGGGCGACAGTGGGGGGCCCATGGTCGCCTCCTTCCACGGCACCTGGTTCCTGGTGGGCCTGGTGAGCTGGGGTGAGG
GCTGTGGGCTCCTTCACAACTACGGCGTTTACACCAAAGTCAGCCGCTACCTCGACTGGATCCATGGGCACATCAGAGACAAGGA
AGCCCCCCAGAAGAGCTGGGCACCTTAGCACCCCTCCCTGCTCACCTCTGGACCCTAGAAGTCACTCTTGGAGTAAGGCTGGGCT
AGTGAGTACCAAGACAGAGGACATTAAAGGAGCATGCAACAAACATACCTCCCCGAGTACCTGTCTGTCTTTTCATCCTTTTTAT
GGGCTATTCTGGGGAAAGTAACATTAATTGAGCATGCACTACACACCAAGTCTATGAAAAGAACCTGCTTAACTCCCAAAGCAG
TTGTGTAGAAGATCTAGTGGGATCTGAGCGATATCACTTCTGGGGGTGAGTGGAGGAGATTGATTTAGAGAAAGGAATTTTTTTA
```

-continued

```
GAAGTTACTGTAAGAGACTAATAGAGCCTTTCTCAGGGCCTTGGAAAGAGCCCGTGCTAGTTACATCAGAAAAGCTTGCCAGTGA
CCAGTGGCCAGTGAGACTCAGAATGGCCATGTGGTGGAGCCAGGATTCAAACCAAGGTCACACTCCCAAACTCAGCTGCTTCTCT
TCTTTATTATCCCTGGGTGTGTGCTGGTGTGTGTGTGCGCGCGTGGGTGTGTGGGTGGATACATGCATGTGTGTGTGTGTGTG
TGTGTGTGTGTGTGTGTGTGTTATATGTTTGGAGACCAGAGGACAACTTCGTTTCTCAACACCATCCACTTGTTTTGTTTTGT
GTTTTGTTTTGTTTGTTGACACAGGGTCTCTCACTGTCCTGAAATCTACCCAGTAGGCTAGGCTGGCTGGCTACCAAACCCCACC
CCACCCTGGCTTTGACAAGTGGAGACAGAAGACCAGTAGTCCACTGGAGATGTGACCAGATGCCCAGAAGGTGCTCCTCATGGTG
CCCTACAGTTTTGTTGAGGAGTCTGTTTAATAATGCAGCTGGGTGCAGTGGCAGCACCTGTAGCCCCCAATACTGAGGCAGCATT
GCTGCAGTCTGAGAGGTGGGGCTCGAGGGACCTAATAACTTCGTATAGCATACATTATACGAAGTTATATTAAGGGTTCCGCAAG
CTCTAGTCGAGCCCCAGCTGGTTCTTTCCGCCTCAGAAGCCATAGAGCCCACCGCATCCCCAGCATGCCTGCTATTGTCTTCCCA
ATCCTCCCCCTTGCTGTCCTGCCCCACCCCACCCCCCAGAATAGAATGACACCTACTCAGACAATGCGATGCAATTTCCTCATTT
TATTAGGAAAGGACAGTGGGAGTGGCACCTTCCAGGGTCAAGGAAGGCACGGGGAGGGGCAAACAACAGATGGCTGGCAACTAG
AAGGCACAGTCGAGGCTGATCAGCGAGCTCTAGAGAATTGATCCCCTCAGAAGAACTCGTCAAGAAGGCGATAGAAGGCGATGCG
CTGCGAATCGGGAGCGGCGATACCGTAAAGCACGAGGAAGCGGTCAGCCCATTCGCCGCCAAGCTCTTCAGCAATATCACGGGTA
GCCAACGCTATGTCCTGATAGCGGTCCGCCACACCCAGCCGGCCACAGTCGATGAATCCAGAAAAGCGGCCATTTTCCACCATGA
TATTCGGCAAGCAGGCATCGCCATGGGTCACGACGAGATCATCGCCGTCGGGCATGCGCGCCTTGAGCCTGGCGAACAGTTCGGC
TGGCGCGAGCCCCTGATGCTCTTCGTCCAGATCATCCTGATCGACAAGACCGGCTTCCATCCGAGTACGTGCTCGCTCGATGCGA
TGTTTCGCTTGGTGGTCGAATGGGCAGGTAGCCGGATCAAGCGTATGCAGCCGCCGCATTGCATCAGCCATGATGGATACTTTCT
CGGCAGGAGCAAGGTGAGATGACAGGAGATCCTGCCCCGGCACTTCGCCCAATAGCAGCCAGTCCCTTCCCGCTTCAGTGACAAC
GTCGAGCACAGCTGCGCAAGGAACGCCCGTCGTGGCCAGCCACGATAGCCGCGCTGCCTCGTCCTGCAGTTCATTCAGGGCACCG
GACAGGTCGGTCTTGACAAAAAGAACCGGGCGCCCCTGCGCTGACAGCCGGAACACGGCGGCATCAGAGCAGCCGATTGTCTGTT
GTGCCCAGTCATAGCCGAAAGCCTCTCCACCCAAGCGGCCGGAGAACCTGCGTGCAATCCATCTTGTTCAATGGCCGATCCCATG
GTTTAGTTCCTCACCTTGTCGTATTATACTATGCCGATATACTATGCCGATGATTAATTGTCAACAGGCTGCAGGTCGAAAGGCC
CGGAGATGAGGAAGAGGAGAACAGCGCGGCAGACGTGCGCTTTTGAAGCGTGCAGAATGCCGGGCCTCCGGAGGACCTTCGGGCG
CCCGCCCCGCCCCTGAGCCCGCCCCTGAGCCCGCCCCCGGACCCACCCCTTCCCAGCCTCTGAGCCCAGAAAGCGAAGGAGCAAA
GCTGCTATTGGCCGCTGCCCCAAAGGCCTACCCGCTTCCATTGCTCAGCGGTGCTGTCCATCTGCACGAGACTAGTGAGACGTGC
TACTTCCATTTGTCACGTCCTGCACGACGCGAGCTGCGGGGCGGGGGGGAACTTCCTGACTAGGGGAGGAGTAGAAGGTGGCGCG
AAGGGGCCACCAAAGAACGGAGCCGGTTGGCGCCTACCGGTGGATGTGGAATGTGTGCGAGGCCAGAGGCCACTTGTGTAGCGCC
AAGTGCCCAGCGGGGCTGCTAAAGCGCATGCTCCAGACTGCCTTGGGAAAAGCGCCTCCCCTACCCGGTAGAATTTCGACGACCT
GCAGCCAAGCTAGCTTCGCGAGCTCGACCGAACAAACGACCCAACACCCGTGCGTTTTATTCTGTCTTTTTATTGCCGCTCAGCT
TTACAGTGACAATGACGGCTGGCGACTGAATATTAGTGCTTACAGACAGCACTACATATTTTCCGTCGATGTTGAAATCCTTTCT
CATATGTCACCATAAATATCAAATAATTATAGCAATCATTTACGCGTTAATGGCTAATCGCCATCTTCCAGCAGGCGCACCATTG
CCCCTGTTTCACTATCCAGGTTACGGATATAGTTCATGACAATATTTACATTGGTCCAGCCACCAGCTTGCATGATCTCCGGTAT
TGAAACTCCAGCGCGGGCCATATCTCGCGCGGCTCCGACACGGGCACTGTGTCCAGACCAGGCCAGGTATCTCTGACCAGAGTCA
TCCTTAGCGCCGTAAATCAATCGATGAGTTGCTTCAAAAATCCCTTCCAGGGCGCGAGTTGATAGCTGGCTGGTGGCAGATGGCG
CGGCAACACCATTTTTTCTGACCCGGCAAAACAGGTAGTTATTCGGATCATCAGCTACACCAGAGACGGAAATCCATCGCTCGAC
CAGTTTAGTTACCCCCAGGCTAAGTGCCTTCTCTACACCTGCGGTGCTAACCAGCGTTTTCGTTCTGCCAATATGGATTAACATT
CTCCCACCGTCAGTACGTGAGATATCTTTAACCCTGATCCTGGCAATTTCGGCTATACGTAACAGGGTGTTATAAGCAATCCCCA
GAAATGCCAGATTACGTATATCCTGGCAGCGATCGCTATTTTCCATGAGTGAACGAACCTGGTCGAAATCAGTGCGTTCGAACGC
TAGAGCCTGTTTTGCACGTTCACCGGCATCAACGTTTTCTTTTCGGATCCGCCGCATAACCAGTGAAACAGCATTGCTGTCACTT
GGTCGTGGCAGCCCGGACCGACGATGAAGCATGTTTAGCTGGCCCAAATGTTGCTGGATAGTTTTTACTGCCAGACCGCGCGCCT
```

-continued

```
GAAGATATAGAAGATAATCGCGAACATCTTCAGGTTCTGCGGGAAACCATTTCCGGTTATTCAACTTGCACCATGCCGCCCACGA
CCGGCAAACGGACAGAAGCATTTTCCAGGTATGCTCAGAAAACGCCTGGCGATCCCTGACATGTCCATCAGGTTCTTGCGAACCT
CATCACTCGTTGCATCGACCGGTAATGCAGGCAAATTTTGGTGTACGGTCAGTAAATTGGACACCTTCCTCTTCTTCTTGGGCAT
GGCCGCAGGAAAGCAGAGCCCTGAAGCTCCCATCACCGGCCAATAAGAGCCAAGCCTGCAGTGTGACCTCATAGAGCAATGTGCC
AGCCAGCCTGACCCCAAGGGCCCTCAGGCTTGGGCACACTGTCTCTAGGACCCTGAGAGAAAGACATACCCATTTCTGCTTAGGG
CCCTGAGGATGAGCCCAGGGGTGGCTTGGCACTGAAGCAAAGGACACTGGGGCTCAGCTGGCAGCAAAGTGACCAGGATGCTGAG
GCTTTGACCCAGAAGCCAGAGGCCAGAGGCCAGGACTTCTCTTGGTCCCAGTCCACCCTCACTCAGAGCTTTACCAATGCCCTCT
GGATAGTTGTCGGGTAACGGTGGACGCCACTGATTCTCTGGCCAGCCTAGGACTTCGCCATTCCGCTGATTCTGCTCTTCCAGCC
ACTGGCTGACCGGTTGGAAGTACTCCAGCAGTGCCTTGGCATCCAGGGCATCTGAGCCTACCAGGTCCTTCAGTACCTCCTGCCA
GGGCCTGGAGCAGCCAGCCTGCAACACCTGCCTGCCAAGCAGAGTGACCACTGTGGGCACAGGGGACACAGGGTGGGGCCCACAA
CAGCACCATTGTCCACTTGTCCCTCACTAGTAAAAGAACTCTAGGGTTGCGGGGGTGGGGGAGGTCTCTGTGAGGCTGGTAAGG
GATATTTGCCTGGCCCATGGAGCTAGCTTGGCTGGACGTAAACTCCTCTTCAGACCTAATAACTTCGTATAGCATACATTATACG
AAGTTATATTAAGGGTTATTGAATATGATCGGAATTGGGCTGCAGGAATTCGATAGCTTGGCTGCAGGTCGACGTACGTAGCAAG
CTTGATGGGCCCTGGTACCACAGCCTGGGCAACACAGCAAAAATCCCTTCCCTTAAAAAAAACAAAAGAGAAGGAAGAAGGACGA
AGTAGAATGTGGAGGACAAACAGGGGAGAGAGGGGAAAGAAAGGGAGGGAATTGTCTTAGAGTTTTACGGCTGTGCACAGACAC
CATGATCAAGGTAACTCTTGTAAGGATAACATTTAGTTGGGGCTGGCTTACAGGTTCAGAAGTTCAGTCCATTATCATCAAGGCA
GGAACATGGCAGCATTCAAGGCAGACATGGTGCAGGAGGAGCTGAGAGTTCTACATCTTCATCTGAAGATTTCTAGTAGAATACT
GGCTTCCAGGCAGCTAGGATGAGGGTCTTAAAGCCCACACCCAGTGACACACCTACTCCAACAGGGCCACACCTCCTAATCATGC
CACTCCCTGGGCTGAGCATATAGAAACCATCACAGAGTCTAACTAGTGTGGCCCATCCTGCACCCATGGAAGACCATCACTGGGG
CATAGACAACCTCCAGAGCCCACCCTGACAGTTCCTGTCTCTGCCTTCTCCAGCAGTCACCAGTTTCAAATAGCTCCTCAAGGAC
AGATGGGGCCTTGTGAGCTTCACCCCGCTGCAGGCTGGAATGCGCCACCTTTAATCCCAGCACTTGGAAGGCAGAGGCAGGCAGA
TTTCTGAGTTCGAGGCCAGCCTAGTCTACAGAGTGAGTTCCAGGACAGCCAGGGCGATACAGAGAAACCCTGTCTCAAAAAACAA
AACAAAACAAAACGATAGAAAAGAGCAAAGTGACCTTGGGCTATGGATGGGATGGACCATCGGGCACTGGGTTGGGAAGCTGAAC
TGGTCCAGATGCCCAGAGCCCAGAGCTCTCTCCTCAGCAGTTCATAACCTGGGGTGTTGCCACAGCACACACAGCAAGGTTAGTT
CTGCTGGTTGTCGGGACTTAGGGTAGGAGGAGTAGAAGCCTGCTACTGATTCTGTCTCTCTGTTTCTCTCTCCTCCCTCCCTC
CCTCCTTCCCTCCCTCCCTCCCTCTTCTTCTTCTTCTCATCCTCCTCCCTCTTCCTCTTCTTCCTCCACCTCCCCACCCCTTATT
TTGATACAGGGTTTCTCTGTGTATCCCTGGCTGTCCTGGAACTCACTCTGTAGCCCAGGTGGGCCTCGAACTCTCAGCCTCAGTC
CCCAGAATGCTGAGAACACAGGTCTGAGTGATCACTGATGGCTAAAAGTTGGGATTACATTGTTGTTGCTTGTTTGTTTATTCTT
TTGTACATGGGACCCAAATACAAATAGTAGCCTCAACAATAAACACGGGATAAGTTGCTGCTCTGCTTTAGGGTCTCCCTGACCT
CTGTTTTTTTGTTTTTTGTTTTTGGTATGTTTTGTTTTCTGTTGTTGTTGTTATCATGTCTATAAATCTATCTTCCTTCCTCCCT
CCTTCCTTCCCTTCCTACTTCCCTCTCTTTCTTCATCCCTCCCTTCCCCCTACTCTCTTTCACCCCCAGATAGGAAGCAAGCATG
ATAAAAACGTGTGGTGTTTTCCTTTTTATGTAGAGAGTACTGTGTAGTGAGTGTTATCCTATGGGTGCTGCCATTCTGCTGTATG
TTACCTGCTGTATGTTATACCAACCTAGATGGTGGTGAACTCACATGGTTGCTTCCATCTTGGTGAGGTTACCAGCCAAGATGTC
TGCCCTCCACATGATTGCCTCCATCTTGGTGAGGTAAATGTTTAATAAAGTAACAAAACAAGACATTAAAAACAAACATTCCAGC
ACAAAATCTTCTTGAGATTAGAGACATAATAGGAAGTCAGGTGAGGTCATACAGGCCATTAATCCCATCACTTGGGGAACAGAGG
CAGGTAGAACTTTGAATTGAAGGCAGGTATATTTAGTGATTTCCAGGGCTATGTAGAGAGGCCCCTGACCCAACTAATAAGTAAA
CAGGAAGATAAATAAATATAATGAACTTAGAATAAAACAAAGAAAGGAAGAAACAAGGGAAGGCAGTGCTGGGGGCCTGGCTTAT
GGTGGATGGGGAATTCTGTGCTAGGGTGCCTGAAACTCTGGGCTCCATCCTCTGTAGTGCATAAACTCTTTGGTACGTTAGCCC
CTGTCTGTAACAAGGAGCTGTCCACGGTTGCAGTACTGCCTTTCCCATCTCAGCTGCCCCTCAGGAGCTGTCCACAGTGGCGACA
CTTTTTTCATCCTCAGCCTACAGCTTTAGGGAAACACCACTGCAGGGGCTGTCCCAAAGGTGCTGTCCACAGAGGCAGCACCTTCT
CTGTGGTCTCACCCCTCCAGACACCCCCCAGCAGCCCCACAGGGATGGCACCTCAGTAAAAGCCAACTGTGGCCAGAGAAGTCTT
```

```
CCTACCCTAACTCATAGACTCGATGCAGGGAAAACAGGGTGAAAAAAGCCACCAAGCCCTGAGCTCCCCCAGCTCAGGACTTA

AAATCTCATCAATCCTCACTATGGAAATCTCTGCCTTGAGAAGCTCTGCCCCCTCATAAATCCTATATAAGAACTGTCCCTTTGT

CCAGTTCCCTGCCATCCGCTCCCAGGAGCAGAGGGCAGTTATCCCTGGATTCATCCCTCCACACCCTGGACCTGCCAATAAACCT

TTCTTGAGATTTCATGCTTCCTGTGATTCTCAGTGGAAGAAGCCAAGAAGAAAAGAACCAAAGAGAGGGAGCCAGGCTGAGGCTC

CTGAGTTCTTCAGCTCAGCTGTGGATACCTGTGATGGTTTGTATATGCTCTGTCCAGGGAATGGCATGATTAGAAGGTGTGGCCC

TGTTGAAGTGAGGTGTGTCACTGTGGGTGTGGGCTATAAGACCCTCATCTTAACTGCATGGAAGTCATTCTTCCACTGGCAGCCT

TCAGATGAAAATGTAGAACTCTCAGCTCCTCCTGCACCATGCCTGCCAGATGCTGCCCTGCTCCCACCTTGATGATAATGGACTG

AACCTCTGAACCTGTAAGCCAGCCCCAATTAAATGTTGTTCTTTATAAGTCTTGCCTTGGTTGTGGTGTCTGTTCACAGCAGTAA

AACCATGACTAAGACAATATCTTCTACTTGGAGCTGCAACAACTCTGCTGAGGAGGCTTCCTCTCAGAGCTATATGGTTCCTGGT

ATCTGTAAAATTCCCTTCTATTGGGACACTTTCCAACCTCAGATCTGTGTGGTTCCTGGCCCCTGTGTCTCGGGATGCCCTTCCA

TTAGAACAGCTTCTCCCCTCAGAGCTGCATGGTTCCTGGACTTCTGAGTCCCAGGAGACCCTTCCATCTGAGCAGAAACACTTAC

AGGAGCAGAGTCCTCCAACACCACGGTTTTGTTTTGAAAGACCAAGACCAACCCTCAGGAGGTTTCTGGCAAAGGCAGATTCTAG

GTGCACCTGGAGGAGACCTATAGTGCAGGACCATCCGTCGTAGGTTGCTAGGCACCAATGGGCAAAGGTAGGGAAGAAATCTTAC

CAGAAGATTCTATTCCATTCCATTCTCCTCACAATGTAAGAGCCAAAGTTAACCTCTAAGGCCCAAGAACAAGGTAACTCTCCAG

AATGCTGGGAGATGTAGTTCTTGGGTAACAACAAGCCATGTTCTCGCCCTAAACAAGTTTGTTTGAATCAACTACACTGAATGTA

CTTGATCATATGTAGGAGAGAGAAGATTGATTCTAGTTCAGGGTTTCAGGCTATTTCAGTCCACCATGATGGGAAAGGCATGACA

TTGTTTATGACAGTAAGAGCATGTAGCAGAGGATCCTCACATCACAACAGGCCGAAATGCAGAGGACAGTGCAACCAGAGGACAG

TCTGTAACTTTCCAAGTCCCTCTTCTAGTGGGTTGCTTCCACCACCTCTCAGGTGGTGCTACAGCTCAGGAACAATTGAGATGTG

TGATGAAGGGCAGGTACTCAACTGTGGCTGTATTGTATCCTTTTATAGTTGTCCTCTGTGTGTTGAGCTATGTGCGAGATTCTCA

GGTCATCGGAGTACCTGTTTTACTTTGGCAGGCATAGGAGACTCCTGAGAACTCTGCCTGACATCCTTGCCAGCCCAAGCTTTGG

TTTAGTGTGTGCAGTATCACTCTTGGGTCTTATCTGCATATCCCTGATGGCCCATCAAGATGTGT
``` mouse Protein C coding sequence (Mouse ProC CDS)
SEQ ID NO: 10
```
ATGTGGCAATTCAGAGTCTTCCTGCTGCTCATGTCCACCTGGGGAATATCTAGCATACCGGCCCATCCTGACCCAGTGTTCTCCA GCAGCGAGCATGCCCACCAGGTGCTTCGGGTCAGACGTGCCAACAGCTTCCTGGAAGAGATGCGGCCAGGCAGCCTGGAACGGGA GTGTATGGAGGAGATCTGTGACTTCGAGGAGGCCCAGGAGATTTTCCAAAATGTGGAAGACACACTGGCCTTCTGGATCAAGTAC TTTGACGGTGACCAGTGCTCGGCTCCACCCTTGGACCACCAGTGCGACAGCCCATGCTGCGGGCATGGCACTTGCATCGACGGCA TAGGCAGCTTCAGCTGCAGCTGCGATAAGGGCTGGGAGGGCAAGTTCTGTCAGCAGGAGTTGCGCTTCCAGGACTGTCGGGTGAA CAATGGCGGCTGCTTGCACTACTGCCTGGAGGAGAGCAATGGGCGGCGCTGCGCTTGTGCCCCGGGCTATGAGCTGGCAGACGAC CACATGCGCTGCAAGTCCACTGTGAATTTTCCATGTGGGAAACTGGGGAGGTGGATAGAGAAGAAACGCAAGATCCTCAAACGAG ACACAGACTTAGAAGATGAACTGGAACCAGATCCAAGGATAGTCAACGAACGCTGACGAAGCAGGGTGACAGTCCTTGGCAGGC AATCCTTCTGGACTCCAAGAAGAAGCTGGCCTGCGGAGGGGTGCTCATCCACACTTCCTGGGTGCTGACGGCAGCCCACTGCGTG GAGGGCACCAAGAAGCTTACCGTGAGGCTTGGTGAGTATGATCTGCGACGCAGGGACCACTGGGAGCTGGACCTGGACATCAAGG AGATCCTCGTCCACCCTAACTACACCCGGAGCAGCAGTGACAACGACATTGCTCTGCTCCGCCTAGCCCAGCCAGCCACTCTCTC CAAAACCATAGTGCCCATCTGCCTGCCGAACAATGGGCTCGCTCAGCAGGAGCTCACTCAGGCTGGCCAGGAGACAGTGGTGACA GGCTGGGGCTATCAAAGCGACAGAATCAAGGATGGCAGAAGGAACCGCACCTTCATCCTCACCTTCATCCGCATCCCTTTGGTTG CTCGAAATGAGTGCGTGGAGGTCATGAAGAATGTGGTCTCGGAGAACATGCTGTGTGCAGGCATCATTGGGAACACGAGAGACGC
```

-continued
```
CTGTGATGGTGACAGTGGGGGGCCCATGGTGGTCTTCTTTCGGGGTACCTGGTTCCTGGTGGGCCTGGTGAGCTGGGGTGAGGGC TGTGGGCACACCAACAACTATGGCATCTACACCAAAGTGGGAAGCTACCTCAAATGGATTCACAGTTACATTGGGGAAAAGGGTG

TCTCCCTTAAGAGCCAGAAGCTATAG
```

Amino acid sequence of human Protein C

SEQ ID NO: 11

```
MWQLTSLLLFVATWGISGTPAPLDSVFSSSERAHQVLRIRKRANSFLEELRHSSLERECIEEICDFEEAKEIFQNVDDTLAFWSK

HVDGDQCLVLPLEHPCASLCCGHGTCIDGIGSFSCDCRSGWEGRFCQREVSFLNCSLDNGGCTHYCLEEVGWRRCSAPGYKLGD

DLLQCHPAVKFPCGRPWKRMEKKRSHLKRDTEDQEDQVDPRLIDGKMTRRGDSPWQVVLLDSKKKLACGAVLIHPSWVLTAAHCM

DESKKLLVRLGEYDLRRWEKWELDLDIKEVFVHPNYSKSTTDNDIALLHLAQPATLSQTIVPICLPDSGLAERELNQAGQETLVT

GWGYHSSREKEAKRNRTFVLNFIKIPVVPHNECSEVMSNMVSENMLCAGILGDRQDACEGDSGGPMVASFHGTWFLVGLVSWGEG

CGLLHNYGVYTKVSRYLDWIHGHIRDKEAPQKSWAP
```

Amino acid sequence of mouse Protein C

SEQ ID NO: 12

```
MWQFRVFLLLMSTWGISSIPAHPDPVFSSSEHAHQVLRVRRANSFLEEMRPGSLERECMEEICDFEEAQEIFQNVEDTLAFWIKY

FDGDQCSAPPLDHQCDSPCCGHGTCIDGIGSFSCSCDKGWEGKFCQQELRFQDCRVNNGGCLHYCLEESNGRRCACAPGYELADD

HMRCKSTVNFPCGKLGRWIEKKRKILKRDTDLEDELEPDPRIVNGTLTKQGDSPWQAILLDSKKKLACGGVLIHTSWVLTAAHCV

EGTKKLTVRLGEYDLRRRDHWELDLDIKEILVHPNYTRSSSDNDIALLRLAQPATLSKTIVPICLPNNGLAQQELTQAGQETVVT

GWGYQSDRIKDGRRNRTFILTFIRIPLVARNECVEVMKNVVSENMLCAGIIGNTRDACDGDSGGPMVVFFRGTWFLVGLVSWGEG

CGHTNYYGIYTKVGSYLKWIHSYIGEKGVSLKSQKL
```

Neo-F (P1) primer

SEQ ID NO: 13

5'-AGGCTGGTAAGGGATATTTGCCTG-3'

3'arm-R (P2) primer

SEQ ID NO: 14

5'-GAGTGAGCCCAGACCCATAACAAT-3'

5'arm-F (P3) primer

SEQ ID NO: 15

5'-TGGGATTACAAGAAACGCCTCAGAC-3'

KI-R (P4) primer

SEQ ID NO: 16

5'-AGGAGTTGGCACGTTTGCGGAT-3'

KI-F (F1) primer

SEQ ID NO: 17

5'-TGGGATTACAAGAAACGCCTCAGAC-3'

KI-R (R1) primer

SEQ ID NO: 18

5'-AGGAGTTGGCACGTTTGCGGAT-3'

KI2-F (F2) primer

SEQ ID NO: 19

5'-GGCTGTGGGCTCCTTCACAACTAC-3'

KI2-R (R2) primer

SEQ ID NO: 20

5'-CAGGTTCTTTTCATAGACTTGGTGTGT-3'

Neo-del-F (F3) primer

SEQ ID NO: 21

5'-AGGGACCTAATAACTTCGTATAGC-3'

Neo-del-R (R3) primer

SEQ ID NO: 22

5'-CCTGTTTGTCCTCCACATTCTACT-3'

WT-F (F4) primer

SEQ ID NO: 23

5'-CATCTACACCAAAGTGGGAAGC-3'

KI2-R (R2) primer

SEQ ID NO: 24

5'-CAGGTTCTTTTCATAGACTTGGTGTGT-3'

```
Seq-F (F1) primer
                                                            SEQ ID NO: 25
5'-TGGGATTACAAGAAACGCCTCAGAC-3'

Seq-R (R3) primer
                                                            SEQ ID NO: 26
5'-CCTGTTTGTCCTCCACATTCTACT-3' hproC 1-F primer
                                                            SEQ ID NO: 27
5'-TGGGATTACAAGAAACGCCTCAGAC-3' hproC 1-R primer
                                                            SEQ ID NO: 28
5'-AGGAGTTGGCACGTTTGCGGAT-3' mproC-F primer
                                                            SEQ ID NO: 29
5'-CATCTACACCAAAGTGGGAAGC-3' mproC-R primer
                                                            SEQ ID NO: 30
5'-CAGGTTCTTTTCATAGACTTGGTGTGT-3'

F8-Common primer
                                                            SEQ ID NO: 31
5'-GAG CAA ATT CCT GTA CTG AC-3'

F8-WT-Forward primer
                                                            SEQ ID NO: 32
5'-TGC AAG GCC TGG GCT TAT TT-3'

F8-Mut-Forward primer
                                                            SEQ ID NO: 33
5'-TGT GTC CCG CCC CTT CCT TT-3'

F9-Common primer
                                                            SEQ ID NO: 34
5'-AAC AGG GAT AGT AAG ATT GTT CC-3'

F9-WT primer
                                                            SEQ ID NO: 35
5'-TGG AAG CAG TAT GTT GGT AAG C-3'

F9-Mut primer
                                                            SEQ ID NO: 36
5'-TCC TGT CAT CTC ACC TTG CTC-3'
```

The invention will now be further described in the following non-limiting Example with reference to the following drawings.

FIG. 1: Schematic depiction of the wildtype mouse Protein C allele (A), the targeting vector (B), the targeted allele (C), and the constitutive knock-in (KI) allele (after Ned deletion) (D). The elements labelled 1, 2 and 9 are exons. A 5' UTR (untranslated region) is part of exon 2 of mouse Protein C and a 3' UTR is part of exon 9 of mouse Protein C. These UTRs are present in the targeting vector and in the targeted allele. Exon 1 consists only of UTR. Human PROC CDS is the coding sequence of human protein C. Neo$^r$=Neo selection cassette. DTA=diphtheria toxin A negative selection marker. Although not depicted in FIG. 1A, the wildtype mouse Protein C allele also comprises exons 3, 4, 5, 6, 7 and 8 (and intervening introns) between exons 2 and 9.

Figure 2:
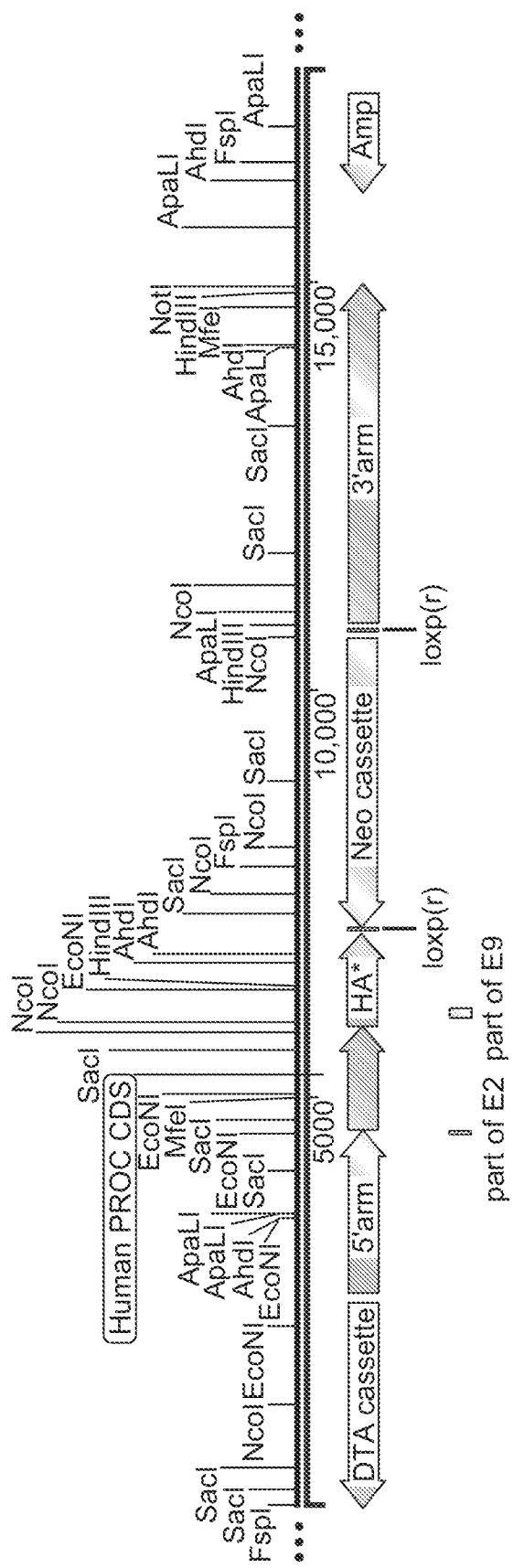

FIG. 2: Further schematic depiction of the targeting vector.

Figure 3:
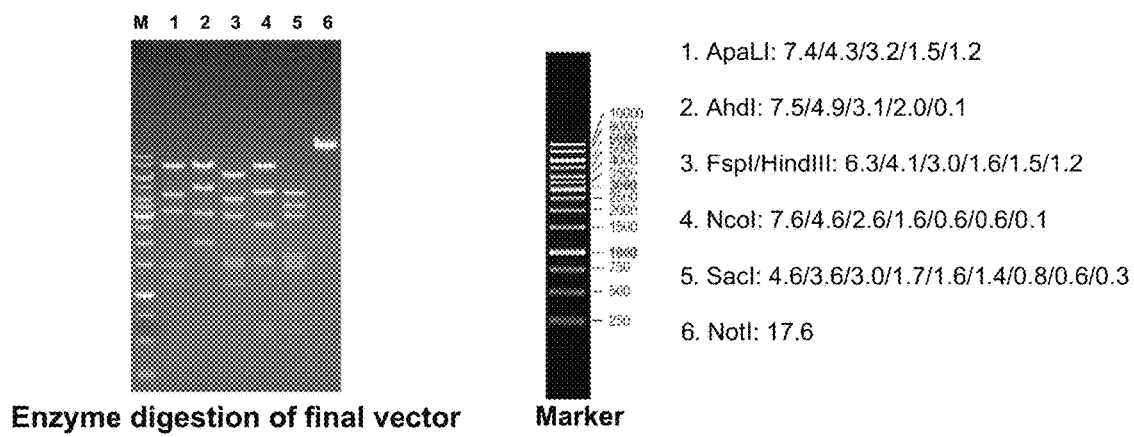

FIG. 3: The targeting vector was digested with the indicated restriction enzymes and the resultant digest products were separated by gel electrophoresis. The left-hand image shows the results of digestion with the indicated restriction enzymes (M: Marker; 1: ApaL1; 2: AhdI; 3: FspI/HindIII; 4: NcoI; 5: SacI; 6: NotI). The nucleic acid fragment sizes (in kilo-base pairs (kb)) with the various restriction enzyme digests are indicated.

FIG. 4: Schematic depiction of the PCR screening strategy for screening in homologous recombination of the targeting construct in mouse embryonic stem (ES) cells. P1, P2, P3 and P4 are oligonucleotide primers used for the PCR screening. Human PROC CDS is the coding sequence of human protein C. Ned=Neo selection cassette.

Figure 5:
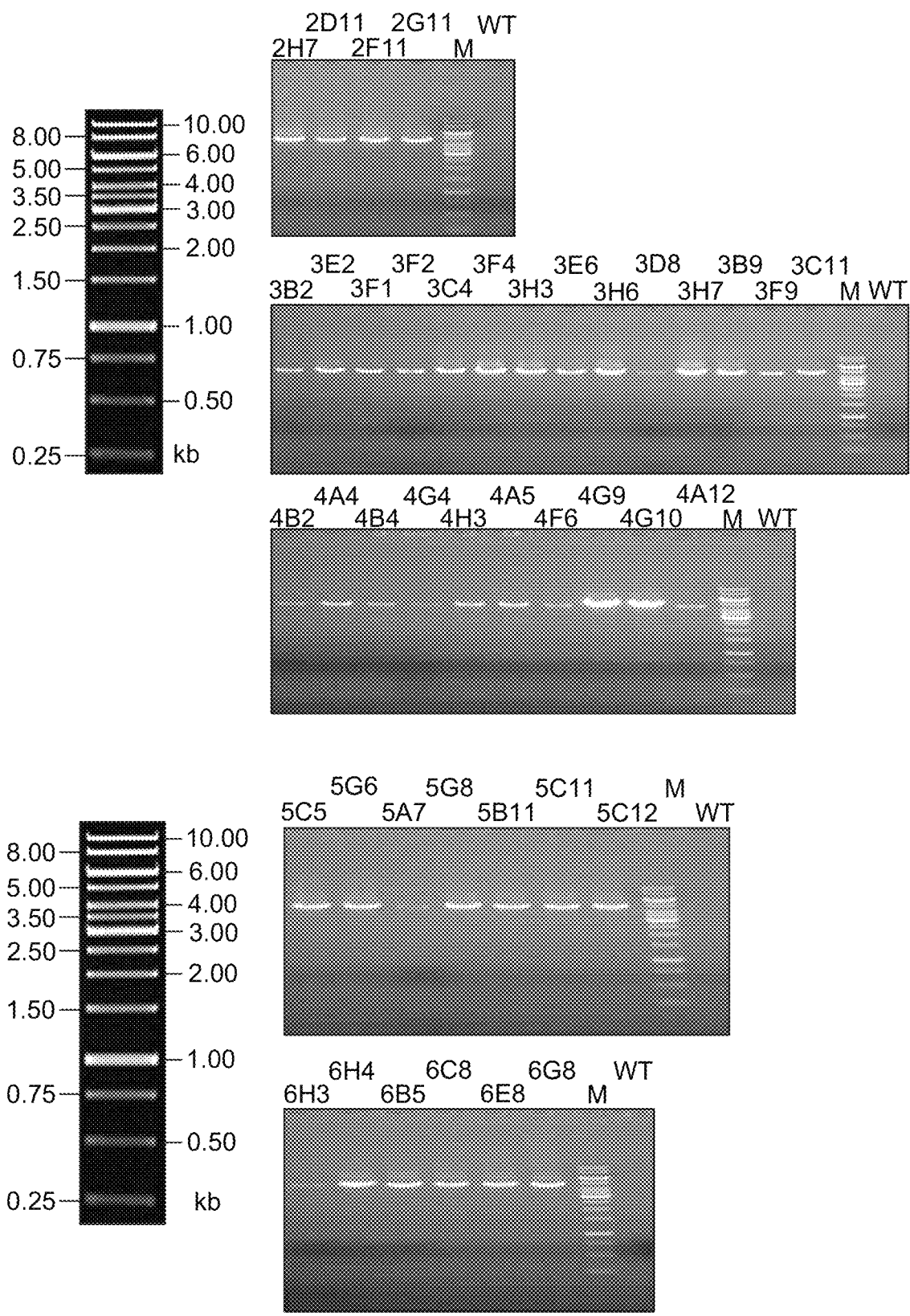

FIG. 5: Gel electrophoresis of PCR products obtained following the 3' arm PCR using primers P1 and P2 as depicted in FIG. 4. M: Marker. An expanded view of the Marker is shown in the left hand panels. WT: Wildtype. The various identifiers (e.g. 2H7, etc.) are the identifiers of the ES clones being screened.

Figure 6:
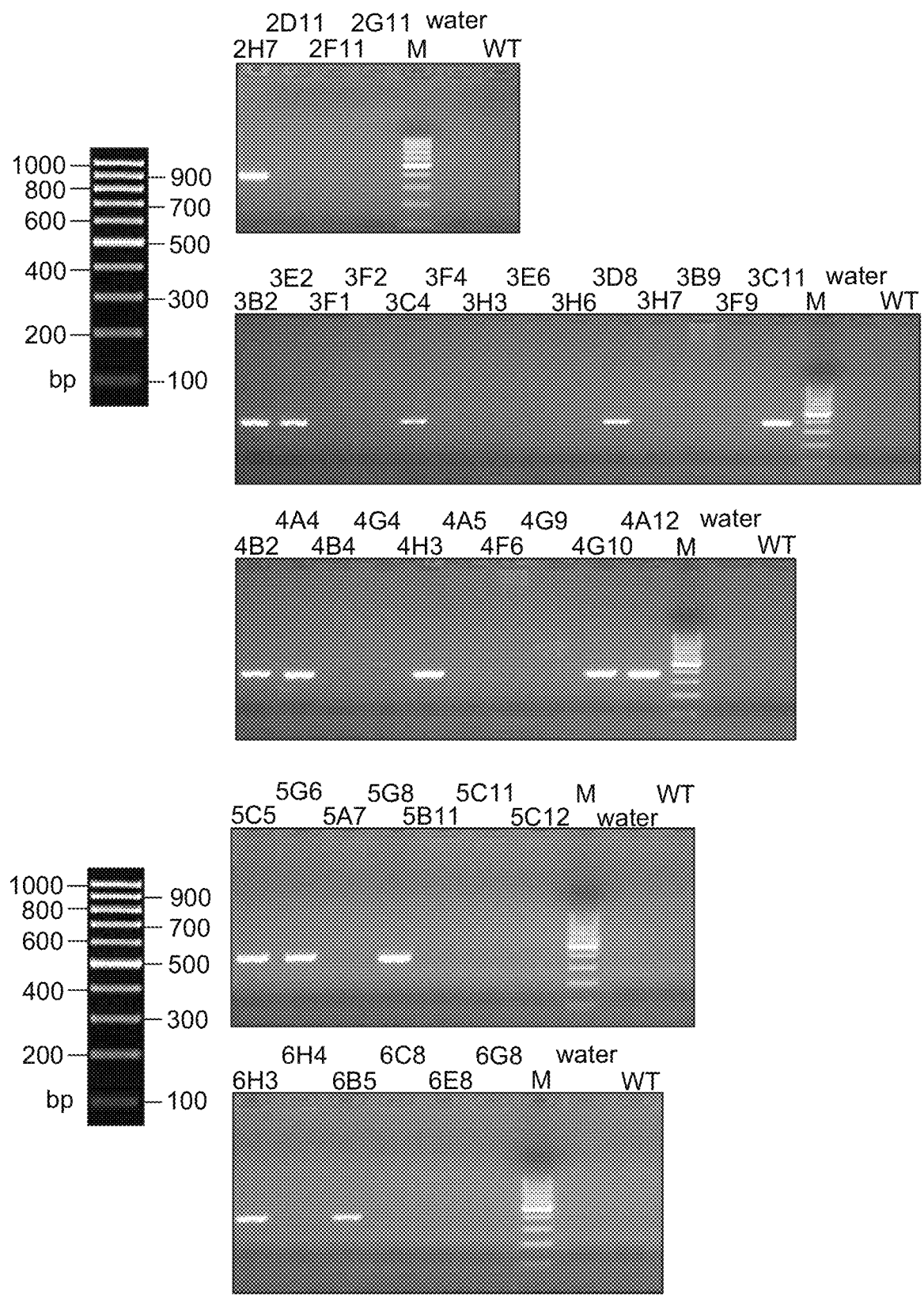

FIG. 6: Gel electrophoresis of PCR products obtained following the KI PCR using primers P3 and P4 as depicted in FIG. 4. M: Marker. An expanded view of the Marker is shown in the left hand panels. WT: Wildtype. The various identifiers (e.g. 2H7, etc.) are the identifiers of the ES clones being screened.

FIG. 7: Schematic depiction of the Southern blot strategy for screening correct targeting of the construct in mouse embryonic stem (ES) cells. The elements labelled 1, 2 and 9 are exons. A 5' UTR (untranslated region) is part of exon 2 of mouse Protein C and a 3' UTR is part of exon 9 of mouse Protein C. These UTRs are present in the targeting vector and in the targeted allele. Exon 1 consists only of UTR. Human PROC CDS is the coding sequence of human protein C. Neo$^r$=Neo selection cassette (also known as the neomycin resistance gene). EcoNI and Bsu36I are restriction enzymes. Although not depicted in FIG. 7A, the wildtype mouse Protein C allele also comprises exons 3, 4, 5, 6, 7 and 8 (and intervening introns) between exons 2 and 9.

Figure 8:
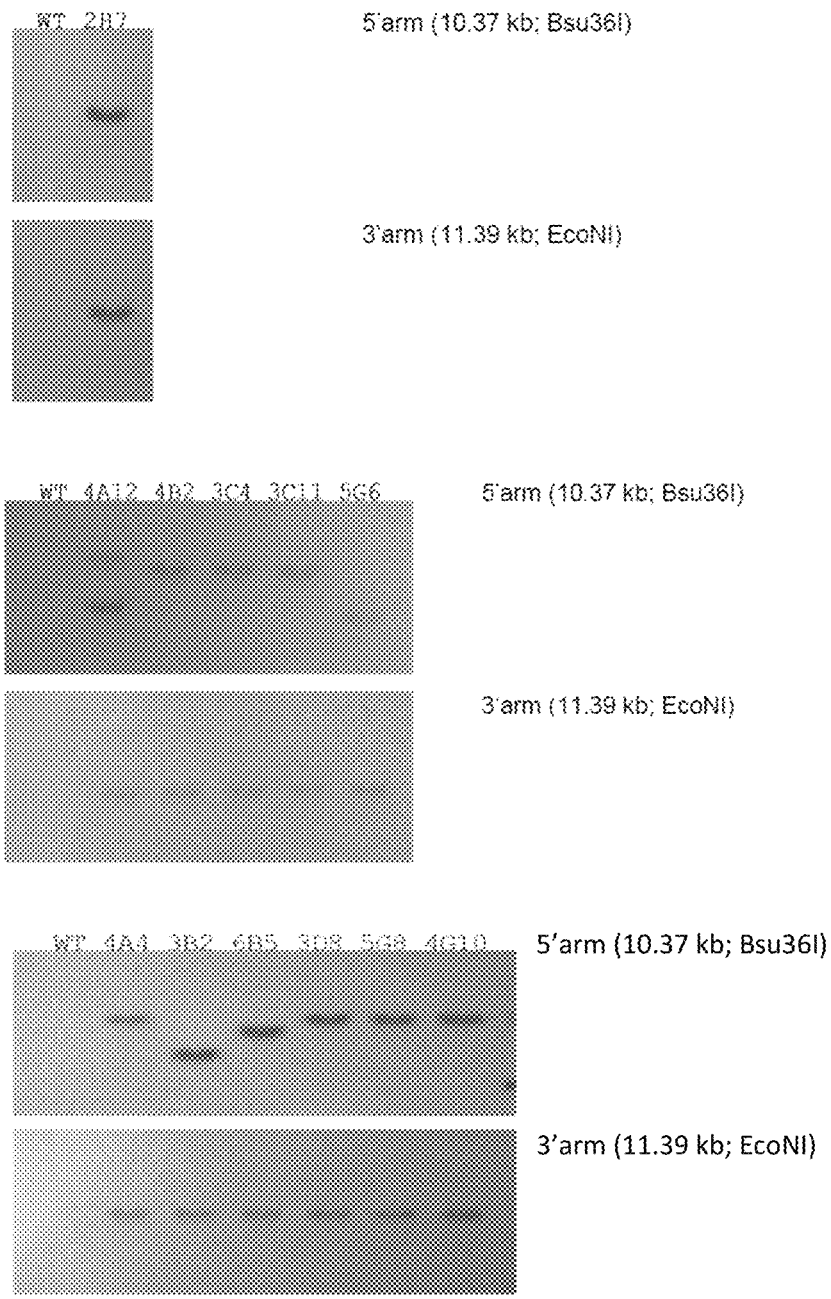

FIG. 8: Results of Southern blot analysis following digestion of genomic DNA from the ES cell clones with the indicated restriction enzymes, electrophoresis of the digestion products and probing with a probe which hybridises to the Neo cassette. WT: Wildtype. The various identifiers (e.g. 2H7, etc.) are the identifiers of the ES clones being screened.

Figure 9:
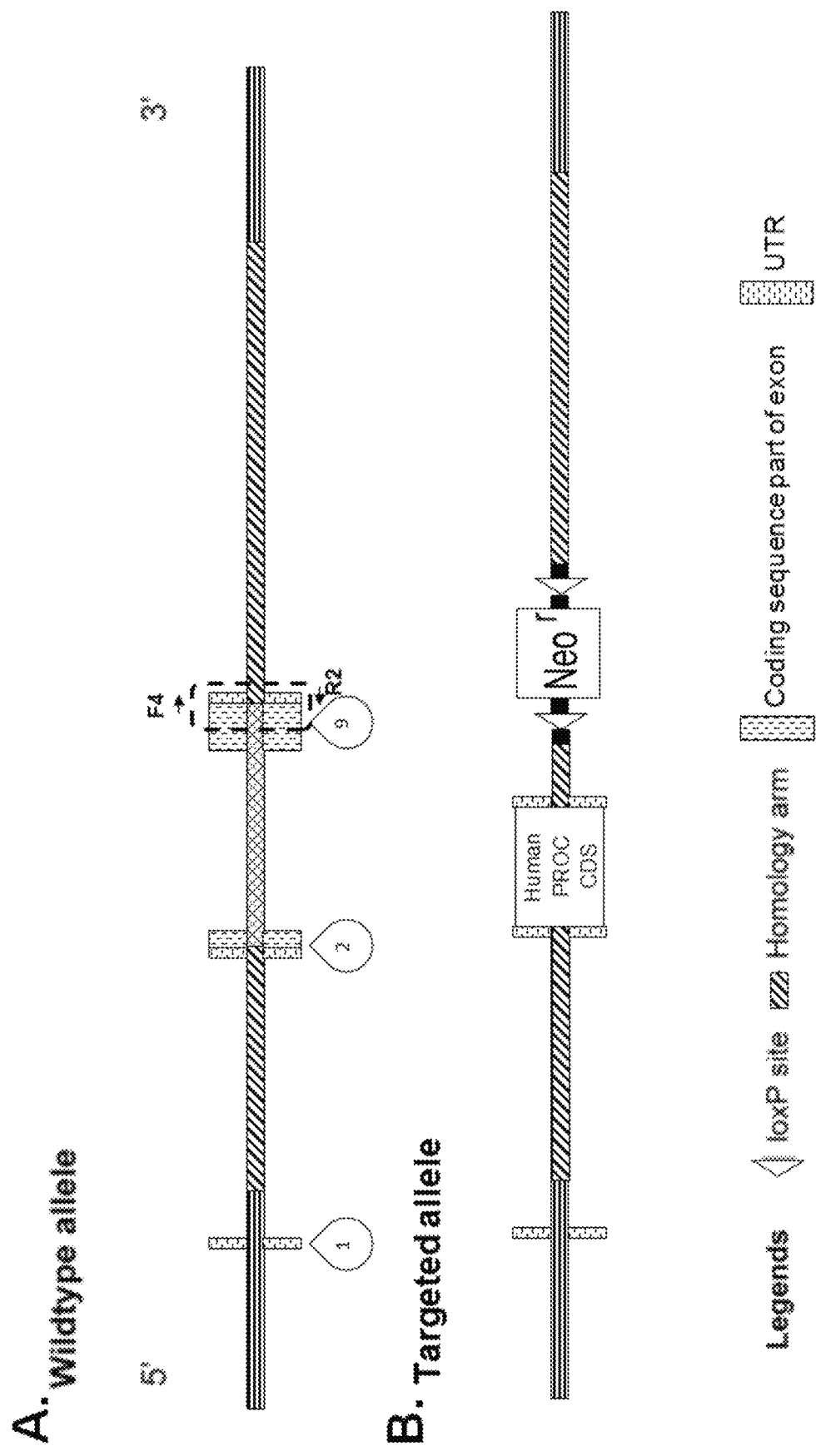
Figure 9:
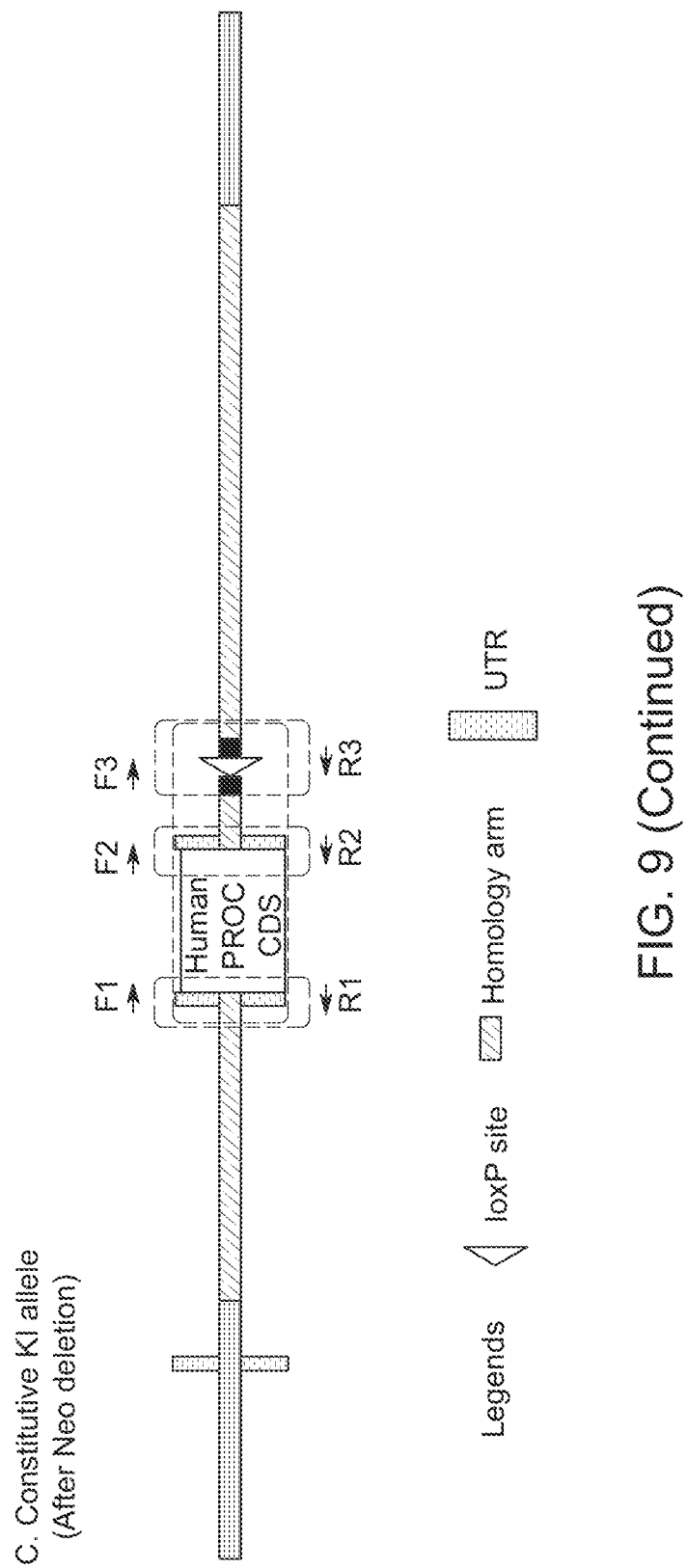

FIG. 9: Schematic depiction of the mouse genotyping strategy. F1, F2, F3, F4, R1, R2 and R3 are oligonucleotide primers used for this PCR-based genotyping screening. The elements labelled 1, 2 and 9 are exons. A 5' UTR (untranslated region) is part of exon 2 of mouse Protein C and a 3' UTR is part of exon 9 of mouse Protein C. Exon 1 consists only of UTR. Human PROC CDS is the coding sequence of human protein C. Neo$^r$=Neo selection cassette. Although not depicted in FIG. 9A, the wildtype mouse Protein C allele also comprises exons 3, 4, 5, 6, 7 and 8 (and intervening introns) between exons 2 and 9.

Figure 10A:
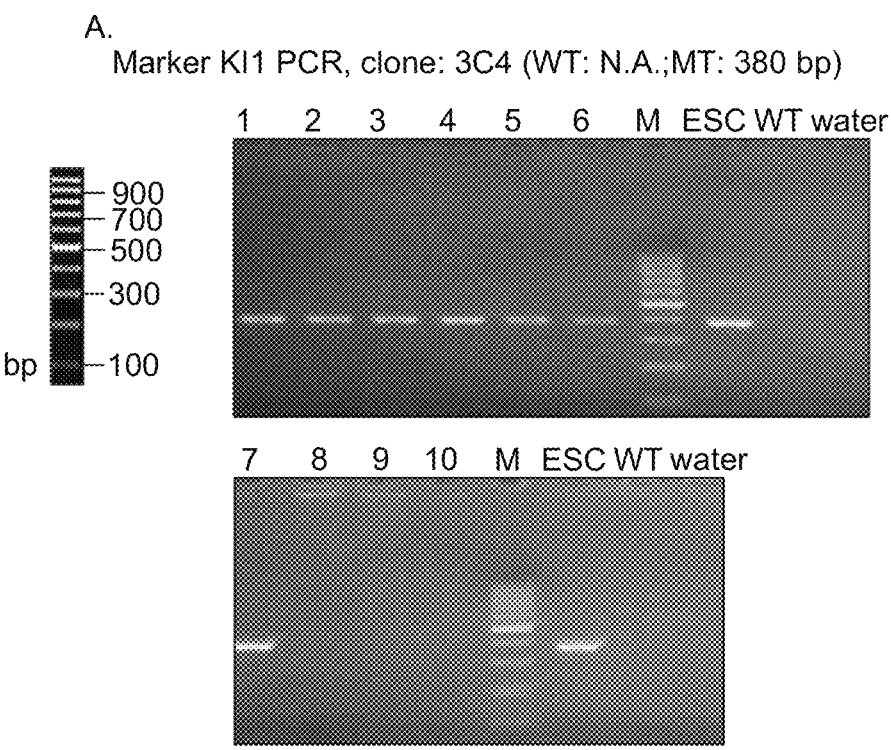
Figure 10B:
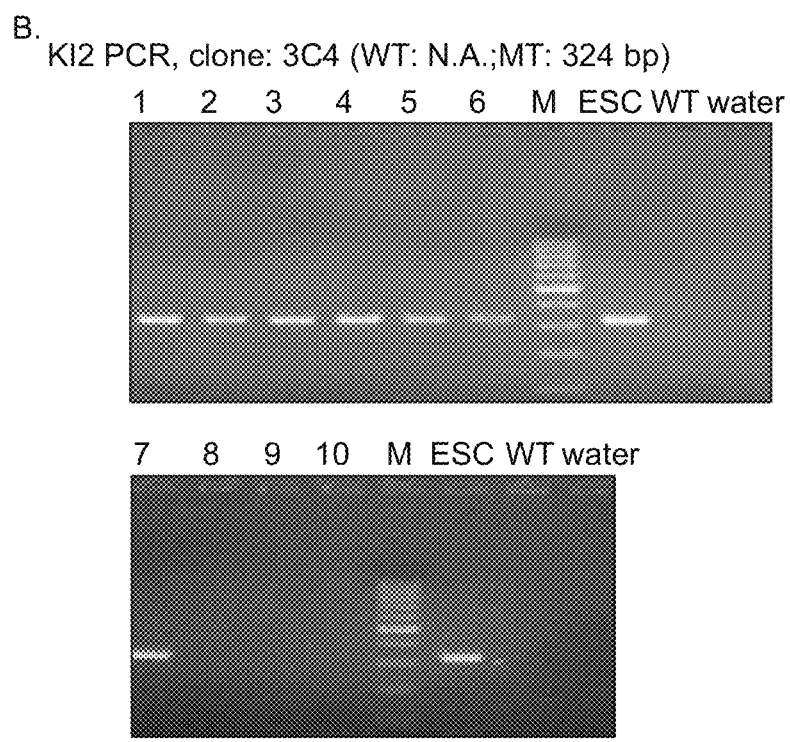
Figure 10:
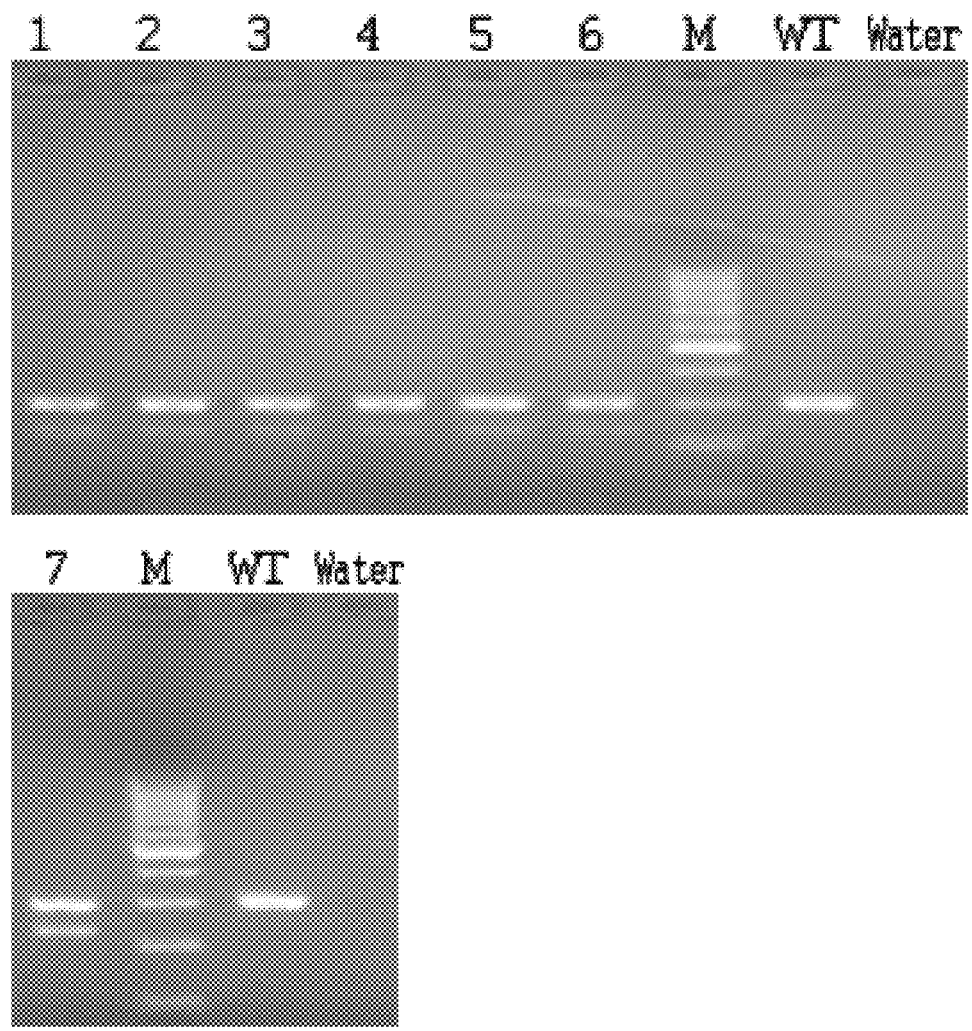

FIG. 10: (A) Gel electrophoresis of PCR products obtained following the KI1 PCR using primers F1 and R1 as depicted in FIG. 9. (B) Gel electrophoresis of PCR products obtained following the KI2 PCR using primers F2 and R2 as depicted in FIG. 9. (C) Gel electrophoresis of PCR products obtained following the Neo deletion PCR using primers F3, R3, F4 and R2 as depicted in FIG. 9. M: Marker. An expanded view of the Marker is provided. ESC: Embryonic Stem Cell. WT: Wildtype. MT: mutant allele (i.e. constitutive knock-in (KI) allele after Neo deletion). The lanes numbered 1-7 correspond to samples obtained from pups 1 #-7 #.

Figure 11:
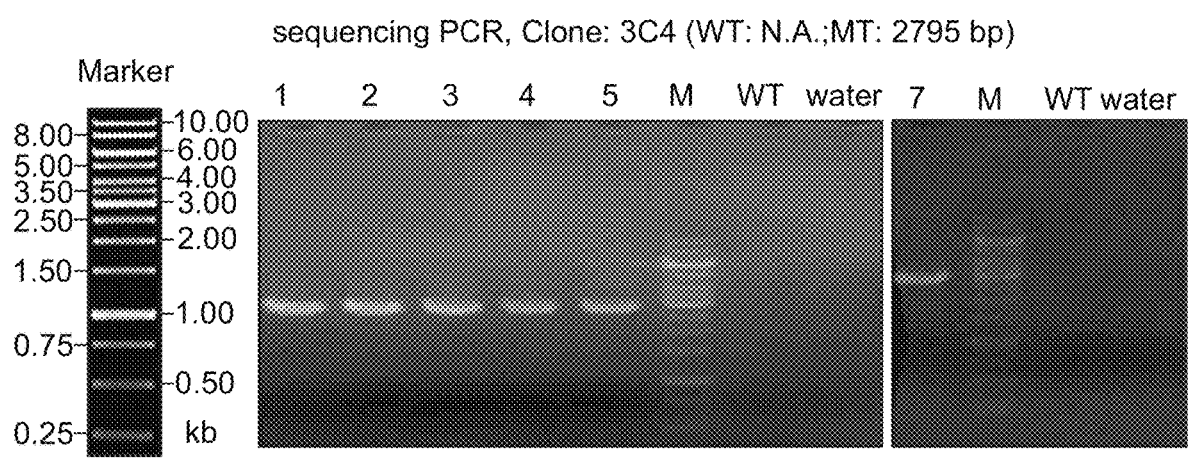

FIG. 11: Gel electrophoresis of PCR products obtained following PCR using primers F1 and R3 as depicted in FIG. 9. M: Marker. An expanded view of the Marker is provided. WT: Wildtype. MT: mutant allele (i.e. constitutive knock-in (KI) allele after Neo deletion).

Figure 12:
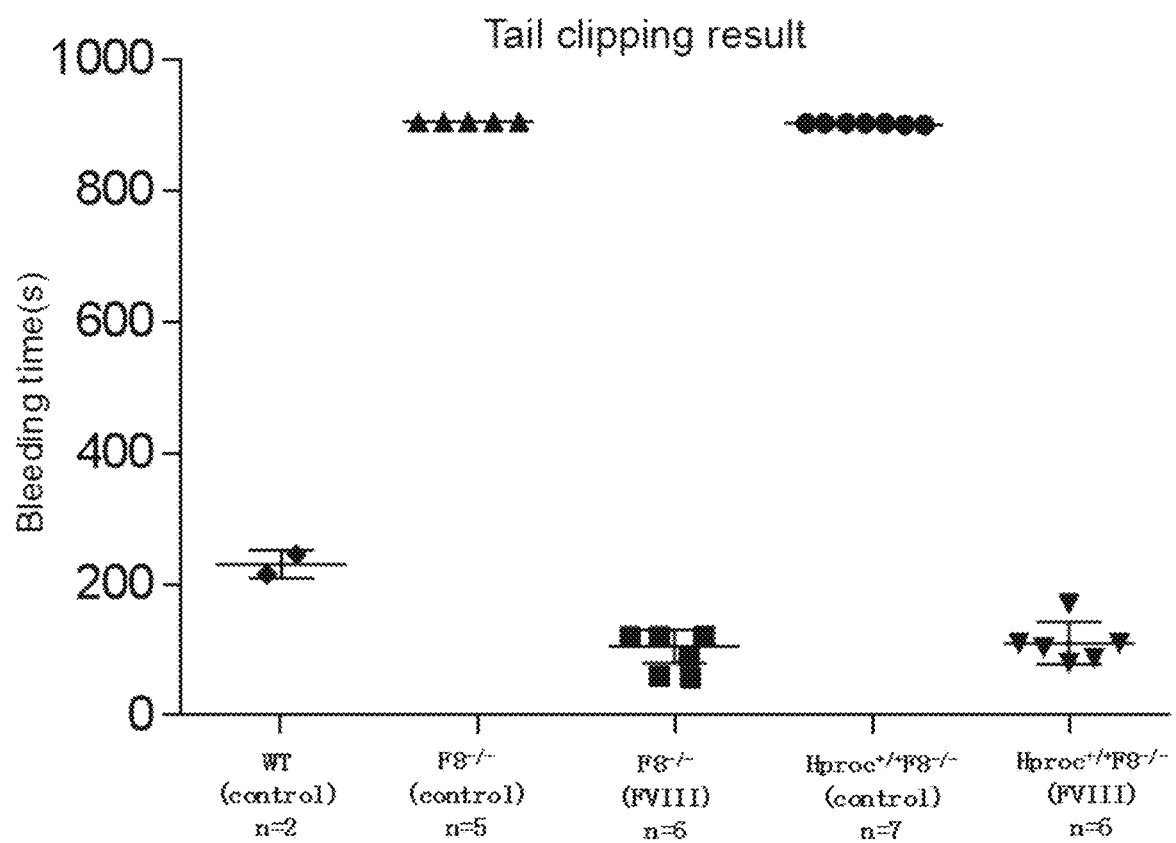
Figure 12:
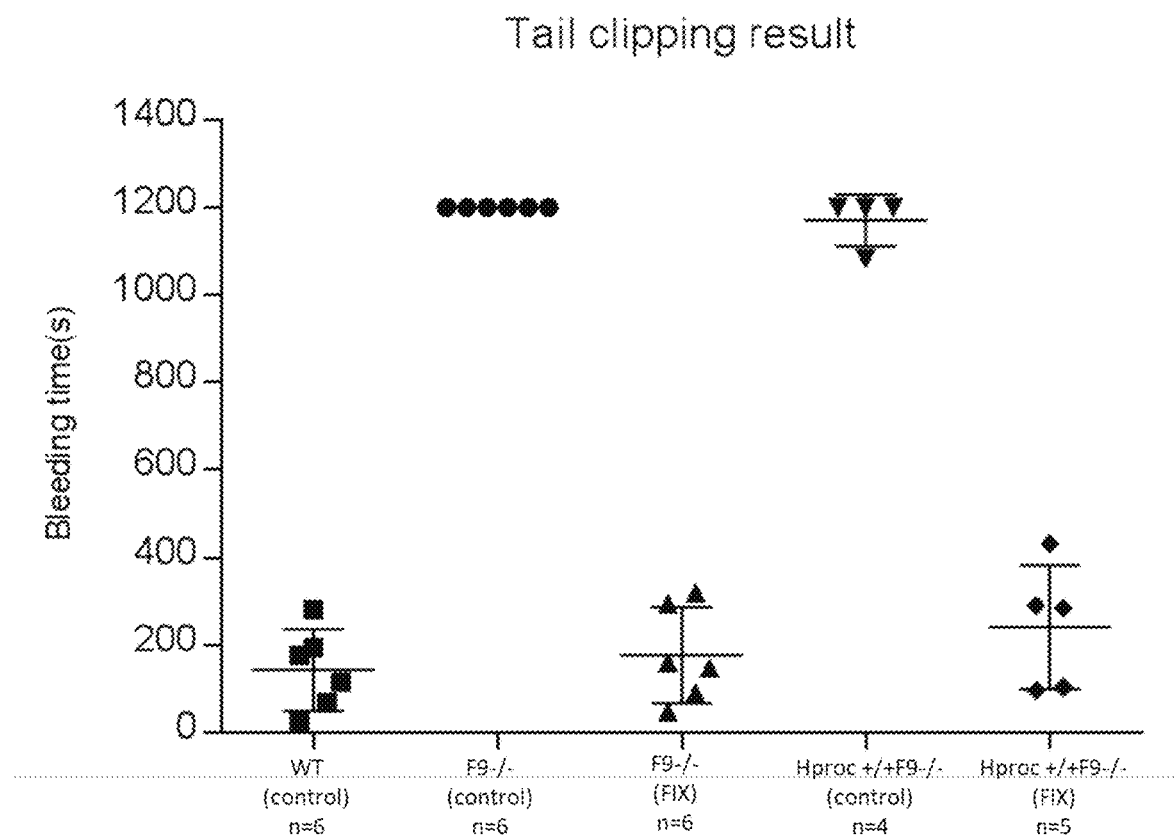

FIG. 12: Graphs showing bleeding times in mouse tail clipping experiments. (A) Hemophilia A model. (B) Hemophilia B model. n=number of mice. WT=Wildtype. F8-/-(control)=F8-/- mice without Factor VIII administration. F8-/-(FVIII)=F8-/- mice with Factor VIII administration. Hproc+/+F8-/-(control)=Hproc+/+F8-/- mice without Factor VIII administration. Hproc+/+F8-/-(FVIII): Hproc+/+F8-/- mice with Factor VIII administration. F9-/-(control)=F9-/- mice without Factor IX administration. F9-/-(FIX)=F9-/- mice with Factor IX administration. Hproc+/+F9-/-(control)=Hproc+/+F9-/- mice without Factor IX administration. Hproc+/+F9-/-(FIX): Hproc+/+ F9-/- mice with Factor IX administration.

Figure 13:
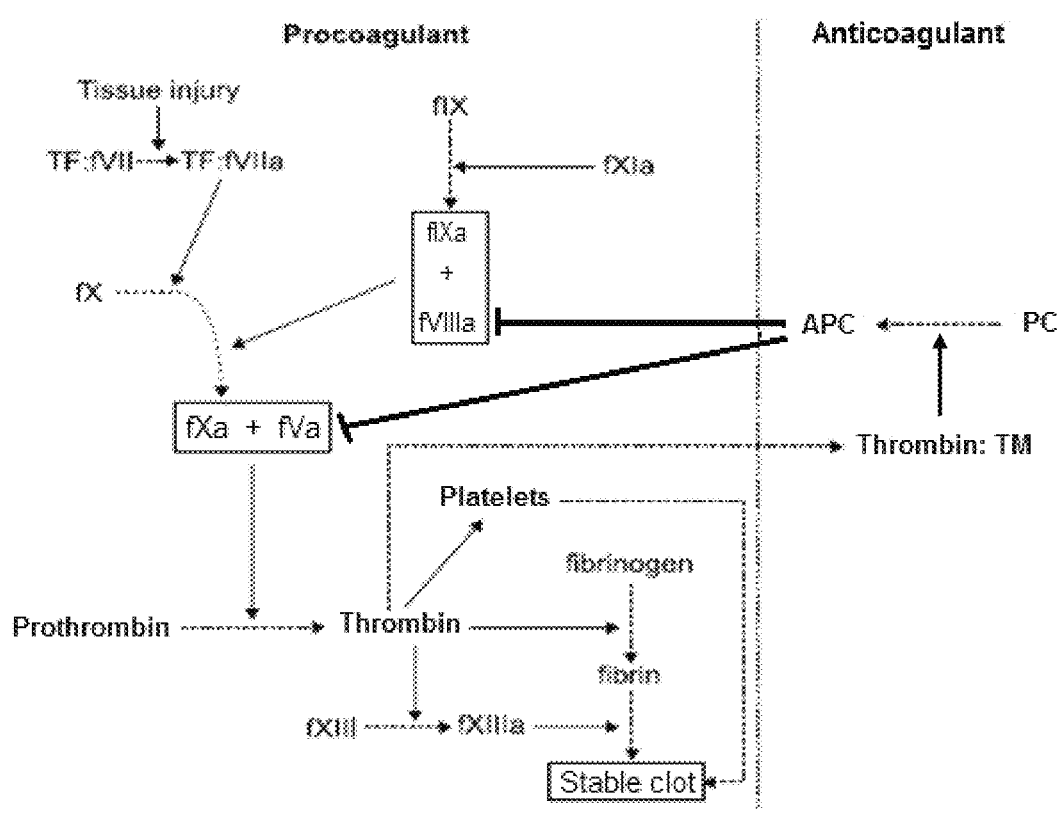

FIG. 13: Schematic depiction of clotting cascade. TF=Tissue Factor. fVII=factor VII. fVIIa=activated factor VII. fX=factor X. fXa=activated factor X. fVa=activated factor V. fIX=factor IX. fIXa=activated factor IX. fXIa=activated factor XI. fVIIIa=activated factor VIII. fXIII=factor XIII. fXIIIa=activated factor XIII APC: Activated Protein C. PC: Protein C. TM: Thrombomodulin. (Adapted from Polderdijk and Huntington, 2018, Scientific Reports, 8:8793; adapted under a Creative Commons Attribution 4.0 International License, available at: creativecommons.org/licenses/by/4.0/.)

EXAMPLE

Human Protein C Constitutive Knock-in Mouse Model Targeting Vector

A targeting vector for generating a knock-in of human protein C into the mouse (C57BL/6) protein C locus was constructed. The nucleotide sequence of the targeting vector is set forth in SEQ ID NO:1.

The mouse protein C gene (NCBI Reference Sequence: NM_001042767.3) is located on mouse chromosome 18. Nine exons have been identified, with the ATG start codon in exon 2 and TAG stop codon in exon 9.

The human protein C gene (NCBI Reference Sequence: NM_000312.3) is located on human chromosome 2. Nine exons have been identified, with the ATG start codon in exon 2 and TAG stop codon in exon 9.

For the knock-in model mouse described herein, the region from ATG start codon to TAG stop codon of mouse protein C was replaced with the coding sequence of human protein C. Thus, the targeting vector includes the coding sequence of human protein C flanked by homology arms for targeting to the mouse protein C locus to achieve targeted replacement of the nucleotide sequence encoding mouse protein C with the human protein C coding sequence.

The targeting vector further comprises, positioned 3' with respect to the human protein C coding sequence (human PROC CDS), a Neo cassette (Neo) flanked by loxP sites. Expression of the Neo cassette can be selected for using the antibiotic G418. The targeting vector further comprises, positioned outside of the homology arms and positioned 5' with respect to the 5' end of the 5' homology arm, a DTA (diphtheria toxin A) negative selection marker.

Mouse genomic fragments containing homology arms (HAs) were amplified from BAC clone by using high fidelity Taq DNA polymerase, and were sequentially assembled into a targeting vector together with site-specific (loxP) recombination sites and selection markers, and the human Protein C coding sequence.

A schematic depiction of the wildtype mouse Protein C allele, the targeting vector, the targeted allele, and the constitutive knock-in (KI) allele (after Neo$^r$ deletion) is set forth in FIG. 1.

A further depiction of the targeting vector is provided in FIG. 2.

The targeting vector was digested by restriction enzymes for confirmation purposes. The results of these confirmatory restriction enzyme digests are shown in FIG. 3. These results demonstrate that the targeting vector was correctly constructed.

Correct construction of the targeting vector was also confirmed by nucleic acid sequencing.

Generation of Human Protein C Constitutive Knock-in Mouse Embryonic Stem (ES) Cells The human protein C targeting construct (SEQ ID NO:1) was linearized by restriction digestion with NotI, followed by phenol/chloroform extraction and ethanol precipitation. The linearized vector was transfected into C57BL/6 ES cells according to standard electroporation procedures. The transfected ES cells were subject to G418 selection (200 μg/mL) 24 hours post electroporation. 564 G418 resistant clones were picked and amplified in 96-well plates. Two copies of 96-well plates were made, one copy was frozen down and stored at −80° C. and the other copy of the 96-well plates was used for DNA isolation and subsequence PCR screening for homologous recombination. The PCR screening identified 16 potential targeted clones, from among which 12 were expanded and further characterized by Southern blot analysis. Eight of the twelve expanded clones were confirmed to be correctly targeted. The PCR screening and Southern blot analysis is described in more detail below.

The regions shown in FIG. 4 were selected for PCR screening. The PCR screening was performed as follows:

3' Arm PCR
Primers for 3'Arm PCR:

```
Neo-F (P1):
                                          (SEQ ID NO: 13)
5'-AGGCTGGTAAGGGATATTTGCCTG-3'

3'arm-R (P2):
                                          (SEQ ID NO: 14)
5'-GAGTGAGCCCAGACCCATAACAAT-3'
```

Expected PCR Product:
Wildtype: None
Targeted: ~4.5 kb
Reaction Mix:

| Component | x1 |
|---|---|
| ES cell genomic DNA | 2.0 μl |
| Forward primer (10 μM) | 0.8 μl |
| Reverse primer (10 μM) | 0.8 μl |
| dNTPs (2.5 mM) | 2.4 μl |
| 5X LongAmp Taq Reaction | 4.0 μl |
| LongAmp Taq DNA Polymerase | 1.2 μl |
| ddH₂O | 8.8 μl |
| Total | 20.0 μl |

Cycling Condition:

| Step | Temp. | Time | Cycles |
|---|---|---|---|
| Initial denaturation | 94° C. | 3 min | |
| Denaturation | 94° C. | 30 s | 33 x |
| Annealing | 60° C. | 30 s | |
| Extension | 65° C. | 50 s/kb | |
| Additional extension | 65° C. | 10 min | |

The results of the 3' arm PCR screening are shown in FIG. 5.

The potentially targeted clones were further screened by PCR for the presence of the knock-in (KI) site.

Primers for KI PCR:

```
5'arm-F (P3):
                                          (SEQ ID NO: 15)
5'-TGGGATTACAAGAAACGCCTCAGAC-3'

KI-R (P4):
                                          (SEQ ID NO: 16)
5'-AGGAGTTGGCACGTTTGCGGAT-3'
```

Expected PCR Product:
Wildtype: None
Targeted: 380 bp
Reaction Mix:

| Component | x1 |
|---|---|
| ES cell genomic DNA | 1.5 μl |
| Forward primer (10 μM) | 1.0 μl |
| Reverse primer (10 μM) | 1.0 μl |
| P112 Taq DNA Polymerase | 12.5 μl |
| ddH₂O | 9.0 μl |
| Total | 25.0 μl |

Cycling Condition:

| Step | Temp. | Time | Cycles |
|---|---|---|---|
| Initial denaturation | 94° C. | 3 min | |
| Denaturation | 94° C. | 30 s | 33 x |
| Annealing | 60° C. | 30 s | |
| Extension | 72° C. | 30 s | |
| Additional extension | 72° C. | 5 min | |
| Storage temperature | 25° C. | | |

The results of the KI PCR screening are shown in FIG. 6. Based on the PCR screening, samples 2H7, 3B2, 3E2, 3C4, 3D8, 3C11, 4B2, 4A4, 4H3, 4G10, 4A12, 5C5, 5G6, 5G8, 6H3 and 6B5 were shown as potentially targeted ES clones.

Positive clones (2H7, 4A12, 4B2, 3C4, 3C11, 5G6, 4A4, 3B2, 6B5, 3D8, 5G8 and 4G10) from PCR screening were expanded and further characterized by Southern blot analysis. The Southern strategy is shown in FIG. 7. The genomic DNA was digested with either Bsu36I or EcoNI, and hybridized using a Neo probe. The Neo probe is expected to detect the following DNA fragment from targeted allele in the Southern analysis: ~10.37 kb (with Bsu36I digestion) and ~11.39 kb (with EcoNI digestion).

Expected Fragment Sizes for Southern Blot:
Neo Probe (containing 5' arm)—10.37 kb-Bsu36I
Neo Probe (containing 3' arm)—11.39 kb-EcoNI Eight of the twelve clones (2H7, 4B2, 3C4, 3C11, 4A4, 3D8, 5G8 and 4G10) were confirmed to be correctly targeted by Southern blot analysis. The results of the Southern blot analysis are shown in FIG. 8.

Generation of Human Protein C Constitutive Knock-in Mice

Targeted ES cell clone 3C4 was injected into C57BL/6 albino embryos, which were then re-implanted into CD-1 pseudo-pregnant females. Founder animals were identified by their coat color, their germline transmission was confirmed by breeding with C57BL/6 females and subsequent genotyping of the offspring. Cre mouse (i.e. a Cre recombinase expressing mouse) was used to mate with F0 (founder animals) to generate F1 mice in which the Neo' cassette that was flanked by loxP sites was deleted. Four male and two female heterozygous targeted mice were generated from clone 3C4. Further details of the mouse genotyping strategy are provided below:

The regions shown in FIG. 9 were selected for PCR-based genotyping of the mice.

KI1 PCR
Primers for KI1 PCR:

```
KI-F (F1):
                                          (SEQ ID NO: 17)
5'-TGGGATTACAAGAAACGCCTCAGAC-3'

KI-R (R1):
                                          (SEQ ID NO: 18)
5'-AGGAGTTGGCACGTTTGCGGAT-3'
```

Expected PCR Product:
Wildtype: N.A.
Targeted: 380 bp
Reaction Mix:

| Component | x1 |
|---|---|
| Mouse genomic DNA | 1.5 μl |
| Forward primer (10 μM) | 1.0 μl |
| Reverse primer (10 μM) | 1.0 μl |
| Premix Taq Polymerase | 12.5 μl |
| ddH$_2$O | 9.0 μl |
| Total | 25.0 μl |

Cycling Condition:

| Step | Temp. | Time | Cycles |
|---|---|---|---|
| Initial denaturation | 94° C. | 3 min | |
| Denaturation | 94° C. | 30 s | 33 x |
| Annealing | 62° C. | 35 s | |
| Extension | 72° C. | 35 s | |
| Additional extension | 72° C. | 5 min | |

KI2 PCR
Primers for KI2 PCR:

```
KI2-F (F2):
                                    (SEQ ID NO: 19)
5'-GGCTGTGGGCTCCTTCACAACTAC-3'

KI2-R (R2):
                                    (SEQ ID NO: 20)
5'-CAGGTTCTTTTCATAGACTTGGTGTGT-3'
```

Expected PCR Product:
Wildtype: N.A.
Targeted: 324 bp
Reaction Mix:

| Component | x1 |
|---|---|
| Mouse genomic DNA | 1.5 μl |
| Forward primer (10 μM) | 1.0 μl |
| Reverse primer (10 μM) | 1.0 μl |
| Premix Taq Polymerase | 12.5 μl |
| ddH$_2$O | 9.0 μl |
| Total | 25.0 μl |

Cycling Condition:

| Step | Temp. | Time | Cycles |
|---|---|---|---|
| Initial denaturation | 94° C. | 3 min | |
| Denaturation | 94° C. | 30 s | 33 x |
| Annealing | 62° C. | 35 s | |
| Extension | 72° C. | 35 s | |
| Additional extension | 72° C. | 5 min | |

Neo Deletion PCR
Primers for Neo Deletion PCR:

```
Neo-del-F (F3):
                                    (SEQ ID NO: 21)
5'-AGGGACCTAATAACTTCGTATAGC-3'

Neo-del-R (R3):
                                    (SEQ ID NO: 22)
5'-CCTGTTTGTCCTCCACATTCTACT-3'

WT-F (F4):
                                    (SEQ ID NO: 23)
5'-CATCTACACCAAAGTGGGAAGC-3'

KI2-R (R2):
                                    (SEQ ID NO: 24)
5'-CAGGTTCTTTTCATAGACTTGGTGTGT-3'
```

Expected PCR Product:
Wildtype: 298 bp
Targeted: 230 bp
Reaction Mix:

| Component | x1 |
|---|---|
| Mouse genomic DNA | 1.5 μl |
| Forward primer1 (F3) (10 μM) | 1.0 μl |
| Reverse primer1 (R3) (10 μM) | 1.0 μl |
| Forward primer2 (F4) (10 μM) | 0.5 μl |
| Reverse primer2 (R2) (10 μM) | 0.5 μl |
| Premix Taq Polymerase | 12.5 μl |
| ddH$_2$O | 8.0 μl |
| Total | 25.0 μl |

Cycling Condition:

| Step | Temp. | Time | Cycles |
|---|---|---|---|
| Initial denaturation | 94° C. | 3 min | |
| Denaturation | 94° C. | 30 s | 33 x |
| Annealing | 62° C. | 35 s | |
| Extension | 72° C. | 35 s | |
| Additional extension | 72° C. | 5 min | |

Results of the Mouse Genotyping PCRs:
Seven pups (1 #, 2 #, 3 #, 4 #, 5 #, 6 # and 7 #) from clone 3C4 were identified positive (i.e. positive for the presence of the constitutive human protein C knock-in (KI) allele) by PCR screening for KI1, KI2 and Neo deletion as described above, the positive pups were reconfirmed by PCR screening for Neo deletion. The PCR results for the Neo deletion PCR confirmed that these pups were heterozygous for the constitutive human protein C knock-in (KI) allele. The Neo deletion PCR also confirms that the 3C4 ES cells were heterozygous for the targeted allele. Note: one mouse (6 #) died. The results of the mouse PCR-based genotyping are shown in FIG. 10.

PCR amplification from mouse DNA was also done using primers F1 and R3 and the PCR amplified fragment (which includes the coding sequence (CDS) of human Protein C and also mouse UTR sequence) was sequenced and no mutations were found. An image of the PCR amplified fragments run on an electrophoretic gel is presented in FIG. 11.

Primers for Sequencing PCR:

```
Seq-F (F1):
                                    (SEQ ID NO: 25)
5'-TGGGATTACAAGAAACGCCTCAGAC-3'

Seq-R (R3):
                                    (SEQ ID NO: 26)
5'-CCTGTTTGTCCTCCACATTCTACT-3'
```

Expected PCR Product:

Wildtype: N.A.

Product Size: 2795 bp

Reaction Mix:

| Component | x1 |
|---|---|
| DNA | 2.0 μL |
| Forward primer (10 μM) | 0.8 μL |
| Reverse primer (10 μM) | 0.8 μL |
| dNTPs (2.5 mM) | 2.4 μL |
| 5X LongAmp Taq Reaction | 4.0 μL |
| Long Amp Taq DNA Polymerase | 1.2 μL |
| ddH₂O | 8.8 μL |
| Total | 20.0 μL |

Cycling Condition:

| Step | Temp. | Time | Cycles |
|---|---|---|---|
| Initial denaturation | 94° C. | 3 min | |
| Denaturation | 94° C. | 30 s | 33 x |
| Annealing | 60° C. | 30 s | |
| Extension | 65° C. | 50 s/kb | |
| Additional extension | 65° C. | 10 min | |

Generating Homozygous Human Protein C Knock-in Mice and Generation of Further Mice Having the Human Protein C Knock-in and Also Factor VIII Deficiency and Generation of Further Mice Having the Human Protein C Knock-in and Also Factor IX Deficiency A. Heterozygous human protein C (hproC+/−) mice mated and 58 offspring mice were genotyped by PCR using the following primers:

```
hproC 1-F:
                                     (SEQ ID NO: 27)
5'-TGGGATTACAAGAAACGCCTCAGAC-3' hproC 1-R:
                                     (SEQ ID NO: 28)
5'-AGGAGTTGGCACGTTTGCGGAT-3'
```

Expected PCR Product: Wildtype: None, Targeted: 380 bp. This hproC primer pair recognizes the human protein C knock-in allele but does not recognize the wildtype (i.e. non-targeted) mouse protein C allele.

```
mproC-F:
                                     (SEQ ID NO: 29)
5'-CATCTACACCAAAGTGGGAAGC-3' mpro-R:
                                     (SEQ ID NO: 30)
5'-CAGGTTCTTTTCATAGACTTGGTGTGT-3'
```

Expected PCR Product: 280 bp from wildtype mice and heterozygous human protein C mice. This mproC primer pair can detect the mouse protein C allele (but not the human protein C targeted allele) and thus can detect wildtype mice, heterozygous human protein C knock-in mice, but not homozygous human protein C knock-in mice.

| Genotype | Mice quantity | Theory yield | Actual yield |
|---|---|---|---|
| hproC+/+ | 3 | 25% | 5.2% |
| hproC+/− | 39 | 50% | 67.2% |
| hproC−/− | 16 | 25% | 27.6% |

For the avoidance of doubt, the genotype hproC+/+ means that the mouse is homozygous for the human Protein C coding sequence (i.e. homozygous for the human Protein C "knock-in" allele). As the targeting vector results in the replacement of the mouse Protein C coding sequence with the human Protein C coding sequence it thus follows that mice of the genotype hproC+/+ do not comprise the mouse Protein C coding sequence. The genotype hproC+/− means that the mouse is heterozygous for the human Protein C coding sequence (i.e. heterozygous for the human Protein C "knock-in"). Thus, a mouse with the genotype hproC+/− comprises the coding sequence for human Protein C (human Protein C "knock-in") and the coding sequence for mouse Protein C. The genotype hproC−/− means that the mouse is homozygous for mouse Protein C and does not comprise the human Protein C coding sequence (i.e. does not comprise the human Protein C "knock-in").

B. Male heterozygous human protein C (hproC+/−) mice mated with female factor VIII deficient mice (F8−/−; the F8−/− mice are completely devoid of factor VIII; F8−/− mice are from Jackson Laboratory, US) and 37 offspring mice were genotyped by PCR using the following primers for F8 genotyping (and also the mproC and hproC primers described above in part A):

```
F8-Common:
                                     (SEQ ID NO: 31)
5'-GAG CAA ATT CCT GTA CTG AC-3'

F8-WT-Forward:
                                     (SEQ ID NO: 32)
5'-TGC AAG GCC TGG GCT TAT TT-3'

F8-Mut-Forward:
                                     (SEQ ID NO: 33)
5'-TGT GTC CCG CCC CTT CCT TT-3'
```

Expected PCR Product: WT (+) F8=620 bp, Mutant (−) F8=420 bp

| Genotype | Mice quantity | Theory yield | Actual yield |
|---|---|---|---|
| hproC+/−, F8+/− | 18 | 50% | 48.6% |
| hproC−/−, F8+/− | 19 | 50% | 51.4% |

For the avoidance of doubt, the F8-WT-Forward and F8-Mut-Forward primers discriminate between the wildtype Factor VIII (F8) allele and the mutant Factor VIII (F8) allele.

C. Male heterozygous human protein C and heterozygous factor VIII (hproC+/−, F8+/−) mice mated with female factor VIII deficient mice (F8−/−) and 31 offspring mice were genotyped by PCR. Note: The F8 (factor VIII) gene is located on X chromosome in mouse. Therefore male heterozygous F8 deficient mice do not have wildtype F8 gene and are equivalent to homozygous F8 deficient mice for mating purposes.

| Genotype | Mice quantity | Theory yield | Actual yield |
|---|---|---|---|
| hproC+/−, F8−/− | 17 | 50% | 54.8% |
| hproC−/−, F8−/− | 14 | 50% | 45.2% |

D. Heterozygous human protein C mice (hproC+/−) mated with heterozygous human protein C and heterozygous factor VIII mice (hproC+/−, F8+/−) and 12 offspring mice were genotyped by PCR

| Genotype | Mice quantity | Theory yield | Actual yield |
|---|---|---|---|
| hproC+/+, F8+/− | 2 | 25% | 16.7% |
| hproC+/−, F8+/−; hproC+/−, F8+/+ | 5 | 50% | 41.7% |
| hproC−/−, F8+/−; hproC−/−, F8+/+ | 5 | 25% | 41.7% |

E. Male homozygous human protein C and heterozygous factor VIII mice (hproC+/+, F8+/−) mated with female heterozygous human protein C and factor VIII deficient mice (hproC+/−, F8−/−) and 25 offspring mice were genotyped by PCR

| Genotype | Mice quantity | Expected yield | Actual yield |
|---|---|---|---|
| hproC+/+, F8−/− | 12 | 50% | 48% |
| hproC+/−, F8−/− | 13 | 50% | 52% |

F. Male heterozygous human protein C (hproC+/−) mice mated with female factor IX deficient mice (F9+/−; the F9+/− mice are partially devoid of factor IX; F9+/− mice are from Jackson Laboratory, US) and 10 offspring mice were genotyped by PCR using the following primers for F9 genotyping (and also the mproC and hproC primers described above in part A):

```
F9-Common:
                                     (SEQ ID NO: 34)
5'-AAC AGG GAT AGT AAG ATT GTT CC-3'

F9-WT:
                                     (SEQ ID NO: 35)
5'-TGG AAG CAG TAT GTT GGT AA GC-3'

F9-Mut:
                                     (SEQ ID NO: 36)
5'-TCC TGT CAT CTC ACC TTG CTC-3'
```

Expected PCR Product: WT(+)F9=620 bp, Mutant(−) F9=420 bp

| Genotype | Mice quantity | Theory yield | Actual yield |
|---|---|---|---|
| hproC+/−, F9+/+ | 5 | 50% | 50% |
| hproC+/−, F9+/− | 2 | 25% | 20% |
| hproC+/−, F9−/− | 3 | 25% | 30% |

For the avoidance of doubt, the F9-WT and F9-Mut primers discriminate between the wildtype Factor IX (F9) allele and the mutant Factor IX (F9) allele. Note: The F9 (factor IX) gene is located on X chromosome in mouse. Therefore, male heterozygous F9 deficient mice do not have wildtype F9 gene and are equivalent to homozygous F9 deficient mice for mating purposes.

G. Male heterozygous human protein C and factor IX deficient mice (hproC+/−, F9+/−) mated with female heterozygous factor IX mice (F9+/−) and 5 offspring mice were genotyped by PCR.

| Genotype | Mice quantity | Theory yield | Actual yield |
|---|---|---|---|
| hproC+/−, F9+/+ | 0 | 12.5% | 0 |
| hproC+/−, F9+/− | 0 | 25% | 0 |
| hproC+/−, F9−/− | 1 | 12.5% | 20% |
| hproC−/−, F9+/+ | 1 | 12.5% | 20% |
| hproC−/−, F9+/− | 1 | 25% | 20% |
| hproC−/−, F9−/− | 2 | 12.5% | 40% |

H. Male heterozygous human protein C and factor IX deficient mice (hproC+/−, F9+/−) mated with female heterozygous human protein C and heterozygous factor IX mice (hproC+/−, F9+/−) and 21 offspring mice were genotyped by PCR.

| Genotype | Mice quantity | Theory yield | Actual yield |
|---|---|---|---|
| hproC+/−, F9+/+ | 3 | 12.5% | 14.3% |
| hproC+/−, F9+/− | 4 | 12.5% | 19% |
| hproC+/−, F9−/− | 2 | 25% | 9.5% |
| hproC−/−, F9+/+ | 2 | 6.75% | 9.5% |
| hproC−/−, F9+/− | 0 | 6.75% | 0 |
| hproC−/−, F9−/− | 3 | 12.5% | 14.3% |
| hproC+/+, F9+/+ | 2 | 6.75% | 9.5% |
| hproC+/+, F9+/− | 1 | 6.75% | 4.75% |
| hproC+/+, F9−/− | 4 | 12.5% | 19% |

I. Male heterozygous human protein C and factor IX deficient mice (hproC+/−, F9+/−) mated with female heterozygous human protein C and factor IX deficient mice (hproC+/−, F9−/−) and 4 offspring mice were genotyped by PCR

| Genotype | Mice quantity | Theory yield | Actual yield |
|---|---|---|---|
| hproC−/−, F9−/− | 1 | 25% | 25% |
| hproC+/−, F9−/− | 1 | 50% | 25% |
| hproC+/+, F9−/− | 2 | 25% | 50% |

Hemophilia Mouse Models

For hemophilia A model, 8 to 10-week-old mice including WT mice, factor VIII deficient mice (F8−/−) and human protein C knockin and factor VIII deficient double mutant mice (hproC+/+, F8−/−) anesthetized using 80 mg/kg sodium pentobarbital i.p. were placed on their abdomen with the tail immersed in 37° C. saline. The distal tail of mice was transected at 4 mm (severe injury), and the bleeding was arterial and venous. Human factor VIII was injected into an orbital vein 5 min before the tail was transected. Controls were also performed in which no Human Factor VIII was injected. For hemophilia B model, the same procedures were conducted except that factor IX deficient mice (F9−/−), human protein C knockin and factor IX deficient double mutant mice (hproC+/+, F9−/−), and human factor IX were used. Bleeding time was measured following the tail-tip transection and immediate immersion of the tail in 10 ml of saline at 37° C. Bleeding time was set at cessation of blood leakage for at least 1 min. After 15 min, the tail was removed from the saline and the bleeding time measure was ended.

RESULTS AND DISCUSSION

Humanized protein C knockin mice were generated by targeted inactivation of the murine protein C gene with a human protein C expression cassette, as described above. The mice (hproC+/+) are viable and able to cross with mouse disease models such as coagulation factor VIII deficient (F8−/−) or factor IX deficient (F9−/−) mice and such models are useful to study the functions of human protein C and activated protein C in mice in vivo.

Human protein C knockin and factor VIII deficient (hproC+/+, F8−/−) or humanized protein C knockin and factor IX deficient (hproC+/+, F9−/−) double mutant mice were generated as described above. These mice appear to be normal and healthy without challenges. If the double mutant hproC+/+F8−/− or double mutant hproC+/+F9−/− mice are challenged by tail cut bleeding, the prolonged bleeding time is comparable to the factor VIII deficient mice (F8−/−) or factor IX deficient mice (F9−/−), respectively. Prolonged bleeding time is the characteristic symptom of hemophilia. Human factor VIII or human factor IX could correct the prolonged bleeding time in factor VIII deficient mice or factor IX deficient mice, respectively, as well as in the respective double mutant mice. The results of the bleeding time study are shown in FIG. 12.

That the bleeding characteristics observed with the double mutant mice (hproC+/+, F8−/−) or (hproC+/+, F9−/−) which express human Protein C (but not mouse protein C) are very consistent with the bleeding characteristics observed with the respective factor VIII deficient mice (F8−/−) or factor IX deficient mice (F9−/−) which express endogenous mouse Protein C (but do not contain the human Protein C knock-in) is desirable and advantageous as this indicates that the human Protein C can functionally complement for the mouse Protein C that has been removed in the double mutant mice. These results indicate that mice having the human Protein C knock-in will be useful models for studying haemophilia or other pathophysiological conditions involving protein C pathway. The double mutant models described in this example (hproC+/+, F8−/−; and hproC+/+, F9−/−) are such models. These models are invaluable and represent the first mouse model for in vivo testing therapeutic candidate agents targeting human protein C or APC.

The double mutant mouse model (hproC+/+, F8−/−) described herein is useful as a model for testing potential candidate therapeutic agents targeting human protein C or APC. This double mutant mouse model is particularly useful as Factor VIII deficiency is characteristic of haemophilia A (classic haemophilia) and thus these mice provide a model of the situation in haemophilia A subjects. Without wishing to be bound by theory, blood clotting in Factor VIII deficient subjects (e.g. haemophilia A sufferers) can still occur, albeit at a much slower rate. Although Factor VIII is a major target of APC, in a Factor VIII deficient subject APC can still exert anticoagulant activity via its inhibitory effect on activated Factor V (fVa). Activated Factor V is essential for clotting and is a major target of APC. Without wishing to be bound by theory, targeting (inhibiting) human Protein C/APC in a Factor VIII deficient animal (e.g. a haemophilia sufferer characterised by a Factor VIII deficiency) can improve clotting by reducing the inhibition of activated Factor V (fVa). FIG. 13 provides a schematic diagram of the clotting cascade.

The double mutant mouse model (hproC+/+, F9−/−) described herein is useful as a model for testing potential candidate therapeutic agents targeting human protein C or APC. This double mutant mouse model is particularly useful as Factor IX deficiency is characteristic of haemophilia B and thus these mice provide a model of the situation in haemophilia B subjects.

Other hproC+/+ knock-in mice of the invention (i.e. other than the hproC+/+F8−/− or hproC+/+F9−/− double mutants described in the present Example) would also be useful mouse models for studying human Protein C (or human activated Protein C, APC) in vivo and identifying potential Protein C/APC targeting therapeutic agents. For example, hproC+/+ knock-in mice that are also deficient in Factor X or Factor XI would represent a useful mouse model as it would represent the situation in human patients who are deficient in Factor X or Factor XI.

In the context of Factor VIII and/or Factor IX deficiency or absence (which characterise certain haemophilias), factor X could still be activated by tissue factor (TF) and activated Factor VII (fVIIa). In the presence of activated factor X (fXa) and activated Factor V (fVa) (which as mentioned above is essential for clotting), prothrombin could be activated into thrombin to initiate clotting. Without wishing to be bound by theory, targeting (inhibiting) human Protein C/APC, e.g. in Factor VIII and/or Factor IX deficient animals, could improve clotting by reducing the inhibition of activated Factor V (fVa).

hproC+/+ knock-in mice that do not contain any further genetic modifications (e.g. no knockouts of other genes) would also be useful mouse models for studying human Protein C/APC activity in vivo and testing potential candidate therapeutic agents targeting human protein C or APC, not only with a view to identifying potential haemophilia therapies, but also therapeutic agents useful in other pathophysiological conditions involving the protein C pathway.

SEQUENCE LISTING

```
<160> NUMBER OF SEQ ID NOS: 36

<210> SEQ ID NO 1
<211> LENGTH: 17617
<212> TYPE: DNA
<213> ORGANISM: Artificial Sequence
<220> FEATURE:
<223> OTHER INFORMATION: Nucleotide sequence of targeting vector

<400> SEQUENCE: 1
cgcttacaat ttccattcgc cattcaggct gcgcaactgt tgggaagggc gatcggtgcg      60
ggcctcttcg ctattacgcc agctggcgaa aggggatgt gctgcaaggc gattaagttg     120
ggtaacgcca gggttttccc agtcacgacg ttgtaaaacg acggccagtg aattgtaata     180
cgactcacta tagggcgaat tggagctcca ccgcccgggc tggttctttc cgcctcagaa     240
```

```
gccatagagc caccgcatc cccagcatgc ctgctattgt cttcccaatc ctccccttg      300 ctgtcctgcc ccaccccacc ccccagaata gaatgacacc tactcagaca atgcgatgca    360
atttcctcat tttattagga aaggacagtg ggagtggcac cttccagggt caaggaaggc    420 acggggagg ggcaaacaac agatggctgg caactagaag gcacagtcga ggctgatcag     480
cgagctctag gatctgcatt ccaccactgc tcccattcat cagttccata ggttggaatc    540
taaaatacac aaacaattag aatcagtagt ttaacacatt atacacttaa aaattttata    600
tttaccttag agctttaaat ctctgtaggt agtttgtcca attatgtcac accacagaag    660
taaggttcct tcacaaagag atcgcctgac acgatttcct gcacaggctt gagccatata    720
ctcatacatc gcatcttggc cacgttttcc acgggtttca aaattaatct caagttctac    780
gcttaacgct ttcgcctgtt cccagttatt aatatattca acgctagaac tcccctcagc    840
gaagggaagg ctgagcacta cacgcgaagc accatcaccg aaccttttga taaactcttc    900
cgttccgact tgctccatca acggttcagt gagacttaaa cctaactctt tcttaatagt    960
ttcggcatta tccacttttta gtgcgagaac cttcgtcagt cctggatacg tcactttgac   1020
cacgcctcca gcttttccag agagcgggtt ttcattatct acagagtatc ccgcagcgtc    1080
gtatttattg tcggtactat aaaacccttt ccaatcatcg tcataatttc cttgtgtacc    1140
agattttggc ttttgtatac cttttttgaat ggaatctaca taaccaggtt tagtcccgtg   1200
gtacgaagaa aagttttcca tcacaaaaga tttagaagaa tcaacaacat catcaggatc    1260
catggcacgc gcttctacaa ggcgctggcc aagaggtgc gggagtttca cgccaccaag     1320
atctgcggca cgctgttgac gctgttaagc gggtcgctgc agggtcgctc ggtgttcgag    1380
gccacacgcg tcaccttaat atgcgaagtg acctgggac cgcgccgccc cgactgcatc     1440
tgcgtgttcg aattcgccaa tgacaagacg ctgggcgggg tttgctcgac attgggtgga   1500
aacattccag gcctgggtgg agaggctttt tgcttcctct tgcaaaacca cactgctcga    1560
cattgggtgg aaacattcca ggcctgggtg gagaggcttt ttgcttcctc ttgaaaacca    1620
cactgctcga tttgttagca gcctcgaatc aacccgggcg atcctaggcg atgagatcta    1680
gctgtcgcga agagtggcgc gcctccctgc acagctagtc acaacgaagg aaggcgctta    1740
gggaaccctg gcagcttgca aaacgcaaag ggctacggct gcatcgctct tttccagact    1800
tctcagctgg gagcttctgg cagttttccc gagtcactcc tttctctcac tagctcacaa    1860
agtggccagc tgagtcagaa gcctccttct agtacaggcc tgcctccac caacgccatc     1920 aatcaggaca agtaaggaag acttctgagt cgccccccc ccccaccggt caaatagagg      1980
ggacatctta tcactgatgg catcctagat tggtgatata tgtaattatt tttgagtgtg    2040
ctacccacga acaagctata tctgtttatg gttgctgttg ttttggtttt tgttttcttt    2100
taaggttctc atccctcagc cactgcgggc aaaaatgaga ccacatttgc caataagttt    2160
gaacacgctc aaccctctct ttctccctcc ctttctgata acaattcct tcggtaggca     2220 gaggtgagca atgggcacac ggagccttcc agagctggga tcagaaaacc tcttgtttgt    2280
ttgtctgggg agagggaggt tcggcaccaa gggctaagca aatatttgcg gttatggatt    2340
aacctgactc ccagactgac atggcgctac ctggacgaaa ttgcagtttc tccttggccc    2400
acgcctgtaa gtccccctca ttgcaagact gtgaaggact gtggagggag gggaggggag    2460
gaaagtccag ctgggaggaa ggtgacgttc ttgagctaag gctctccagg cagactgaaa    2520
tgtggggcca aggaaaatga gcgcccaaac tctatctgga ccaaggcgtg ggttccctac    2580
```

```
aatccaggtg accatctcga cacatgagat tttgtggatc aagtggacag cagtcaaagg    2640
gttccctatg atcaggaacc atcctcagag caatcttgaa acccagaacc ccactactcc    2700
cctctgccct gttctctaag gtggactcta caattccgga agccagcaaa gccgaagagt    2760
gaggccagga ggggctgtgc agctgggata ggcgggcctg cccacctggt ctgggggaca    2820
ctagaggcct tgtggtttga ctactggttg ggggcagggg ttaaggttcc agagttgggg    2880
ccacataggc ttggccttga agccaaactc tgccctcctc ttaggtgtag gcttgtgaca    2940
agccgcgtat ctcctccaag cctttgggtc ccttcccatg aaatggaggt gagaatattc    3000
atgccttcct cttttaacag tgatcagtgt gtgtgtgtgt gtgtgtgtgt gtgtgtgtgt    3060
gtgtgtgtgt gtgtgtgtgt gtggtgtaga gtgtggtttc tggtgttcag ggttgaaccc    3120
agaatcttaa acatgccaag tacgttcttt cctactgaac tgcaaccctc cagtatcctg    3180
tacttgttgt ttgtttgttt gtttgtttgt ttgttcggaa gcacctgtgg tggcacacac    3240
ttacaatcct agtgctagag agcagaaaca agtggatccc ttgggcttgc tggctggcca    3300
gcctacgtga tgagtttcag gcagtgagag accttgtccc aaacaataag gtggaagtaa    3360
gccatgatgg catacccctt tagagctagt actcgagagg cagaagcagg tggagtttaa    3420
gaccagcctg gtctacatag aagttccagg atagccaaaa agtacccaag gccatccaaa    3480
aaaacaaaaa caaaacaaaa cctggaggga aaaaaaaaac cagacaatgc ctggggaagg    3540
atgaaggaca gtcagtcaga ttatccctgg tcaaacgtg  tgcacaaatc tgtgcacaca    3600
agaaagagct tcacatgggt tactatttgt tttccaacaa ctcattttta agcccccact    3660
ctctttctct gttttttaaaa aaggtttatt tattttatgt atatgagtac attattgctc    3720
tcttcagaca caccagaaaa ggacataaga ttccattaca gatggttgtg agccaccatg    3780
tggttgctgg aatttgaact caggtcctct ggaagagcag tcggtgctct taaccactga    3840
accatctccc cagcccttcc aacaactctt tatggaagaa acctattcta tccattttat    3900
aaatgacaga actgaggcac ggagcacgta aacatcttgt taaataccctc tctctctctc    3960 tctctctccc cagtaggaaa tggaatttgc cccaggcaat gacttttttt tttttttttt    4020
tgctttcatg tacctagagt aagcccagct ctaaaggcca cgagattgtc tgtctgtgga    4080
ccgtggtgta ccccactccc agacccagct tccacacaga caatgagctc acaaacgtcc    4140 tttactcccct tccttccttg cttgctctgt gtgtgtgtgt gtgtgtgtgt gtgtgtgtta    4200
agagatcaac ctcagacatt ttctttagga gctatttacc ttgcttttg  agacagggcc    4260 tccggatggc ctggagctag tcacctggag ctggtcaagc aggctagggt ggctggccta    4320
agcaatccac aggatctgct tatctctgcc tccccagtcc tgggattaca agaaacgcct    4380
cagacaccta gatttctgtt ttaattttct atgggttctg gggatctttc ttaagtcttc    4440
aagtatgcac ggaaagggct ttattgacta agatatctcc cctgctcagg aatggccctt    4500
tcattctact ttggagggag ctgggggtgg ggcggggagc agctcagctg tgtgtatcct    4560
tggagcttag aagttctcct cagacaggtg tcagcagctc caggatgtgg cagctcacaa    4620
gcctcctgct gttcgtggcc acctgggaa ttccggcac accagctcct cttgactcag     4680
tgttctccag cagcgagcgt gcccaccagg tgctgcggat ccgcaaacgt gccaactcct    4740
tcctggagga gctccgtcac agcagcctgg agcgggagtg catagaggag atctgtgact    4800
tcgaggaggc caaggaaatt ttccaaaatg tggatgacac actggccttc tggtccaagc    4860
acgtcgacgg tgaccagtgc ttggtcttgc ccttggagca cccgtgcgcc agcctgtgct    4920
gcgggcacgg cacgtgcatc gacggcatcg gcagcttcag ctgcgactgc cgcagcggct    4980
```

```
gggagggccg cttctgccag cgcgaggtga gcttcctcaa ttgctcgctg gacaacggcg    5040
gctgcacgca ttactgccta gaggaggtgg gctggcggcg ctgtagctgt gcgcctggct    5100
acaagctggg ggacgacctc ctgcagtgtc accccgcagt gaagttccct tgtgggaggc    5160
cctggaagcg gatggagaag aagcgcagtc acctgaaacg agacacagaa gaccaagaag    5220
accaagtaga tccgcggctc attgatggga agatgaccag gcggggagac agcccctggc    5280
aggtggtcct gctggactca aagaagaagc tggcctgcgg ggcagtgctc atccacccct    5340
cctgggtgct gacagcggcc cactgcatgg atgagtccaa gaagctcctt gtcaggcttg    5400
gagagtatga cctgcggcgc tgggagaagt gggagctgga cctggacatc aaggaggtct    5460
tcgtccaccc caactacagc aagagcacca ccgacaatga catcgcactg ctgcacctgg    5520
cccagcccgc caccctctcg cagaccatag tgcccatctg cctcccggac agcggccttg    5580
cagagcgcga gctcaatcag gccggccagg agaccctcgt gacgggctgg ggctaccaca    5640
gcagccgaga gaaggaggcc aagagaaacc gcaccttcgt cctcaacttc atcaagattc    5700
ccgtggtccc gcacaatgag tgcagcgagg tcatgagcaa catggtgtct gagaacatgc    5760
tgtgtgcggg catcctcggg gaccggcagg atgcctgcga gggcgacagt ggggggccca    5820
tggtcgcctc cttccacggc acctggttcc tggtgggcct ggtgagctgg ggtgagggct    5880
gtgggctcct tcacaactac ggcgtttaca ccaaagtcag ccgctacctc gactggatcc    5940
atgggcacat cagagacaag gaagccccc agaagagctg ggcaccttag cacccctccc    6000
tgctcacctc tggaccctag aagtcactct tggagtaagg ctgggctagt gagtaccaag    6060
acagaggaca ttaaggagc atgcaacaaa catacctccc cgagtacctg tctgtctttt    6120 catcctttt atgggctatt ctggggaaa gtaacattaa ttgagcatgc actacacacc    6180
aagtctatga aaagaacctg cttaactccc aaagcagttg tgtagaagat ctagtgggat    6240
ctgagctgat atcacttctg ggggtgagtg gaggagattg atttagagaa aggaattttt    6300
ttagaagtta ctgtaagaga ctaatagagc ctttctcagg gccttggaaa gagcccgtgc    6360
tagttacatc agaaaagctt gccagtgacc agtggccagt gagactcaga atggccatgt    6420
ggtggagcca ggattcaaac caaggtcaca ctcccaaact cagctgcttc tcttctttat    6480
tatccctggg tgtgtgctgg tgtgtgtgtg cgcgcgtggg tgtgtgggtg gatacatgca    6540
tgtgtgtgtg tgtgtgtgtg tgtgtgtgtg tgtgtgtgtg tgttatatgt ttggagacca    6600
gaggacaact tcgtttctca acaccatcca cttgttttgt tttgtgtttt gttttgtttg    6660
ttgacacagg gtctctcact gtcctgaaat ctacccagta ggctaggctg gctggctacc    6720 aaacccccacc ccaccctggc tttgacaagt ggagacagaa gaccagtagt ccactggaga    6780
tgtgaccaga tgcccagaag gtgctcctca tggtgcccta cagttttgtt gaggagtctg    6840
tttaataatg cagctgggtg cagtggcagc acctgtagcc cccaatactg aggcagcatt    6900
gctgcagtct gagaggtggg gctcgaggga cctaataact tcgtatagca tacattatac    6960
gaagttatat taagggttcc gcaagctcta gtcgagcccc agctggttct ttccgcctca    7020
gaagccatag agcccaccgc atccccagca tgcctgctat tgtcttccca atcctccccc    7080
ttgctgtcct gccccacccc acccccagaa atagaatgac acctactcag acaatgcgat    7140
gcaatttcct cattttatta ggaaaggaca gtgggagtgg caccttccag ggtcaaggaa    7200
ggcacggggg aggggcaaac aacagatggc tggcaactag aaggcacagt cgaggctgat    7260
cagcgagctc tagagaattg atcccctcag aagaactcgt caagaaggcg atagaaggcg    7320
```

```
atgcgctgcg aatcgggagc ggcgataccg taaagcacga ggaagcggtc agcccattcg   7380
ccgccaagct cttcagcaat atcacgggta gccaacgcta tgtcctgata gcggtccgcc   7440
acacccagcc ggccacagtc gatgaatcca gaaaagcggc cattttccac catgatattc   7500
ggcaagcagg catcgccatg ggtcacgacg agatcatcgc cgtcgggcat gcgcgccttg   7560
agcctggcga acagttcggc tggcgcgagc ccctgatgct cttcgtccag atcatcctga   7620
tcgacaagac cggcttccat ccgagtacgt gctcgctcga tgcgatgttt cgcttggtgg   7680
tcgaatgggc aggtagccgg atcaagcgta tgcagccgcc gcattgcatc agccatgatg   7740
gatactttct cggcaggagc aaggtgagat gacaggagat cctgccccgg cacttcgccc   7800
aatagcagcc agtcccttcc cgcttcagtg acaacgtcga gcacagctgc gcaaggaacg   7860
cccgtcgtgg ccagccacga tagccgcgct gcctcgtcct gcagttcatt cagggcaccg   7920
gacaggtcgg tcttgacaaa aagaaccggg cgcccctgcg ctgacagccg gaacacggcg   7980
gcatcagagc agccgattgt ctgttgtgcc cagtcatagc cgaatagcct ctccacccaa   8040
gcggccggag aacctgcgtg caatccatct tgttcaatgg ccgatccat ggtttagttc     8100
ctcaccttgt cgtattatac tatgccgata tactatgccg atgattaatt gtcaacaggc   8160
tgcaggtcga aaggcccgga gatgaggaag aggagaacag cgcggcagac gtgcgctttt   8220
gaagcgtgca gaatgccggg cctccggagg accttcgggc gcccgccccg cccctgagcc   8280
cgcccctgag cccgccccg gacccacccc ttcccagcct ctgagcccag aaagcgaagg     8340
agcaaagctg ctattggccg ctgccccaaa ggcctacccg cttccattgc tcagcggtgc   8400
tgtccatctg cacgagacta gtgagacgtg ctacttccat ttgtcacgtc ctgcacgacg   8460
cgagctgcgg ggcggggggg aacttcctga ctaggggagg agtagaaggt ggcgcgaagg   8520
ggccaccaaa gaacggagcc ggttggcgcc taccggtgga tgtggaatgt gtgcgaggcc   8580
agaggccact tgtgtagcgc caagtgccca gcggggctgc taaagcgcat gctccagact   8640
gccttgggaa aagcgcctcc cctacccggt agaatttcga cgacctgcag ccaagctagc   8700
ttcgcgagct cgaccgaaca aacgacccaa cacccgtgcg ttttattctg tctttttatt   8760
gccgctcagc tttacagtga caatgacggc tggcgactga atattagtgc ttacagacag   8820
cactacatat tttccgtcga tgttgaaatc ctttctcata tgtcaccata aatatcaaat   8880
aattatagca atcatttacg cgttaatggc taatcgccat cttccagcag gcgcaccatt   8940
gcccctgttt cactatccag gttacggata tagttcatga caatatttac attggtccag   9000
ccaccagctt gcatgatctc cggtattgaa actccagcgc gggccatatc tcgcgcggct   9060
ccgacacggg cactgtgtcc agaccaggcc aggtatctct gaccagagtc atccttagcg   9120
ccgtaaatca atcgatgagt tgcttcaaaa atcccttcca gggcgcgagt tgatagctgg   9180
ctggtggcag atggcgcggc aacaccattt tttctgaccc ggcaaaacag gtagttattc   9240
ggatcatcag ctacaccaga gacggaaatc catcgctcga ccagtttagt tacccccagg   9300
ctaagtgcct tctctacacc tgcggtgcta accagcgttt cgttctgcc aatatggatt     9360
aacattctcc caccgtcagt acgtgagata tctttaaccc tgatcctggc aatttcggct   9420
atacgtaaca gggtgttata agcaatcccc agaaatgcca gattacgtat atcctggcag   9480
cgatcgctat tttccatgag tgaacgaacc tggtcgaaat cagtgcgttc gaacgctaga   9540
gcctgttttg cacgttcacc ggcatcaacg ttttcttttc ggatccgccg cataaccagt   9600
gaaacagcat tgctgtcact tggtcgtggc agcccggacc gacgatgaag catgtttagc   9660
tggcccaaat gttgctggat agttttact gccagaccgc gcgcctgaag atatagaaga      9720
```

```
taatcgcgaa catcttcagg ttctgcggga aaccatttcc ggttattcaa cttgcaccat    9780
gccgcccacg accggcaaac ggacagaagc attttccagg tatgctcaga aaacgcctgg    9840
cgatccctga acatgtccat caggttcttg cgaacctcat cactcgttgc atcgaccggt    9900
aatgcaggca aattttggtg tacggtcagt aaattggaca ccttcctctt cttcttgggc    9960
atggccgcag gaaagcagag ccctgaagct cccatcaccg gccaataaga gccaagcctg   10020
cagtgtgacc tcatagagca atgtgccagc cagcctgacc ccaagggccc tcaggcttgg   10080
gcacactgtc tctaggaccc tgagagaaag acatacccat ttctgcttag ggccctgagg   10140
atgagcccag gggtggcttg gcactgaagc aaaggacact ggggctcagc tggcagcaaa   10200
gtgaccagga tgctgaggct ttgacccaga agccagaggc cagaggccag gacttctctt   10260
ggtcccagtc caccctcact cagagcttta ccaatgccct ctggatagtt gtcgggtaac   10320
ggtggacgcc actgattctc tggccagcct aggacttcgc cattccgctg attctgctct   10380
tccagccact ggctgaccgg ttggaagtac tccagcagtg ccttggcatc cagggcatct   10440
gagcctacca ggtccttcag tacctcctgc cagggcctgg agcagccagc ctgcaacacc   10500
tgcctgccaa gcagagtgac cactgtgggc acagggacca cagggtgggg cccacaacag   10560
caccattgtc cacttgtccc tcactagtaa aagaactcta gggttgcggg gggtgggga    10620 ggtctctgtg aggctggtaa gggatatttg cctggcccat ggagctagct tggctggacg   10680
taaactcctc ttcagaccta ataacttcgt atagcataca ttatacgaag ttatattaag   10740
ggttattgaa tatgatcgga attgggctgc aggaattcga tagcttggct gcaggtcgac   10800
gtacgtagca agcttgatgg gccctggtac cacagcctgg gcaacacagc aaaaatccct   10860
tcccttaaaa aaacaaaag agaaggaaga aggacgaagt agaatgtgga ggacaaacag    10920
gggagagagg gggaaagaaa gggagggaat tgtcttagag ttttacggct gtgcacagac   10980
accatgatca aggtaactct tgtaaggata acatttagtt ggggctggct tacaggttca   11040
gaagttcagt ccattatcat caaggcagga acatggcagc attcaaggca gacatggtgc   11100
aggaggagct gagagttcta catcttcatc tgaagatttc tagtagaata ctggcttcca   11160
ggcagctagg atgagggtct taaagcccac acccagtgac acacctactc caacagggcc   11220
acacctccta atcatgccac tccctgggct gagcatatag aaaccatcac agagtctaac   11280
tagtgtggcc catcctgcac ccatggaaga ccatcactgg ggcatagaca acctccagag   11340
cccaccctga cagttcctgt ctctgccttc tccagcagtc accagtttca aatagctcct   11400
caaggacaga tggggccttg tgagcttcac cccgctgcag gctggaatgc gccacccttta  11460 atcccagcac ttggaaggca gaggcaggca gatttctgag ttcgaggcca gcctagtcta   11520
cagagtgagt tccaggacag ccagggcgat acagagaaac cctgtctcaa aaacaaaac    11580 aaaacaaaac gatagaaaag agcaaagtga ccttgggcta tggatgggat ggaccatcgg   11640
gcactgggtt gggaagctga actggtccag atgcccagag cccagagctc tctcctcagc   11700
agttcataac ctggggtgtt gccacagcac acacagcaag gttagttctg ctggttgtcg   11760
ggacttaggg taggaggagt agaagcctgc tactgattct gtctctctct gtttctctct   11820
cctccctccc tccctccttc cctccctccc tcctcttct tcttcttctc atcctcctcc    11880
ctcttcctct tcttcctcca cctcccacc ccttatttg atacagggtt tctctgtgta     11940
tccctggctg tcctggaact cactctgtag cccaggtggg cctcgaactc tcagcctcag   12000
tccccagaat gctgagaaca caggtctgag tgatcactga tggctaaaag ttgggattac   12060
```

```
attgttgttg cttgtttgtt tattcttttg tacatgggac ccaaatacaa atagtagcct      12120
caacaataaa cacgggataa gttgctgctc tgctttaggg tctccctgac ctctgttttt      12180
ttgttttttg ttttggtat gttttgtttt ctgttgttgt tgttatcatg tctataaatc      12240
tatcttcctt cctccctcct tccttcccct cctacttccc tctctttctt catccctccc      12300 ttcccctac tctctttcac ccccagatag gaagcaagca tgataaaaac gtgtggtgtt      12360 ttcctttta tgtagagagt actgtgtagt gagtgttatc ctatgggtgc tgccattctg      12420
ctgtatgtta cctgctgtat gttataccaa cctagatggt ggtgaactca catggttgct      12480
tccatcttgg tgaggttacc agccaagatg tctgccctcc acatgattgc ctccatcttg      12540
gtgaggtaaa tgtttaataa agtaacaaaa caagacatta aaacaaaca ttccagcaca      12600 aaatcttctt gagattagag acataatagg aagtcaggtg aggtcataca ggccattaat      12660
cccatcactt ggggaacaga ggcaggtaga actttgaatt gaaggcaggt atatttagtg      12720
atttccaggg ctatgtagag aggcccctga cccaactaat aagtaaacag gaagataaat      12780
aaatataatg aacttagaat aaaacaaaga aggaagaaa caagggaagg cagtgctggg      12840
ggcctggctt atggtggatg ggggaattct gtgctagggt gcctgaaact ctgggctcca      12900
tcctctgtag tgcataaact cttttggtacg ttagcccctg tctgtaacaa ggagctgtcc      12960
acggttgcag tactgccttt cccatctcag ctgcccctca ggagctgtcc acagtggcga      13020
cactttttca tcctcagcct acagcttag ggaaacacca ctgcaggggc tgtcccaaag      13080
gtgctgtcca cagaggcagc accttctctg tggtctcacc cctccagaca cccccagca      13140 gccccacagg gatggcacct cagtaaaagc caactgtggc cagagaagtc ttcctaccct      13200
aactcataga ctcgatgcag ggaaaacagg gtgaaaaaaa gccaccaagc cctgagctcc      13260
ccccagctca ggacttaaaa tctcatcaat cctcactatg gaaatctctg ccttgagaag      13320
ctctgccccc tcataaatcc tatataagaa ctgtcccttt gtccagttcc ctgccatccg      13380
ctcccaggag cagagggcag ttatccctgg attcatccct ccacaccctg gacctgccaa      13440
taaacctttc ttgagatttc atgcttcctg tgattctcag tggaagaagc caagaagaaa      13500
agaaccaaag agagggagcc aggctgaggc tcctgagttc ttcagctcag ctgtggatac      13560
ctgtgatggt ttgtatatgc tctgtccagg gaatggcatg attagaaggt gtggccctgt      13620
tgaagtaggt gtgtcactgt gggtgtgggc tataagaccc tcatcttaac tgcatggaag      13680
tcattcttcc actggcagcc ttcagatgaa aatgtagaac tctcagctcc tcctgcacca      13740
tgcctgccta gatgctgccc tgctcccacc ttgatgataa tggactgaac ctctgaacct      13800
gtaagccagc cccaattaaa tgttgttctt tataagtctt gccttggttg tggtgtctgt      13860
tcacagcagt aaaaccatga ctaagacaat atcttctact tggagctgca acaactctgc      13920
tgaggaggct tcctctcaga gctatatggt tcctggtatc tgtaaaattc ccttctattg      13980
ggacactttc caacctcaga tctgtgtggt tcctggcccc tgtgtctcgg gatgcccttc      14040
cattagaaca gcttctcccc tcagagctgc atggttcctg gacttctgag tcccaggaga      14100
cccttccatc tgagcagaaa cacttacagg agcagagtcc tccaacacca cggttttgtt      14160 ttgaaagacaaagaccaacc ctcaggaggt ttctggcaaa gcagattct aggtgcacct      14220 ggaggagacc tatagtgcag gaccatccgt cgtaggttgc taggcaccaa tgggcaaagg      14280
tagggaagaa atcttaccag aagattctat tccattccat tctcctcaca atgtaagagc      14340
caaagttaac ctctaaggcc caagaacaag gtaactctcc agaatgctgg gagatgtagt      14400
tcttgggtaa caacaagcca tgttctcgcc ctaaacaagt ttgtttgaat caactacact      14460
```

```
gaatgtactt gatcatatgt aggagagaga agattgattc tagttcaggg tttcaggcta    14520
tttcagtcca ccatgatggg aaaggcatga cattgtttat gacagtaaga gcatgtagca    14580
gaggatcctc acatcacaac aggccgaaat gcagaggaca gtgcaaccag aggacagtct    14640
gtaactttcc aagtccctct tctagtgggt tgcttccacc acctctcagg tggtgctaca    14700
gctcaggaac aattgagatg tgtgatgaag ggcaggtact caactgtggc tgtattgtat    14760 cctttttatag ttgtcctctg tgtgttgagc tatgtgcgag attctcaggt catcggagta    14820
cctgttttac tttggcaggc ataggagact cctgagaact ctgcctgaca tccttgccag    14880
cccaagcttt ggtttagtgt gtgcagtatc actcttgggt cttatctgca tatccctgat    14940
ggcccatcaa gatgtgtgcg gccgcgtacc agcttttgtt ccctttagtg agggttaatt    15000
tcgagcttgg cgtaatcatg gtcatagctg tttcctgtgt gaaattgtta ccgctcaca     15060 attccacaca acatacgagc cggaagcata aagtgtaaag cctggggtgc ctaatgagtg    15120
agctaactca cattaattgc gttgcgctca ctgcccgctt tccagtcggg aaacctgtcg    15180
tgccagctgc attaatgaat cggccaacgc gcggggagag cggtttgcg tattgggcgc     15240 tcttccgctt cctcgctcac tgactcgctg cgctcggtcg ttcggctgcg gcgagcggta    15300
tcagctcact caaaggcggt aatacggtta ccacagaat cagggggataa cgcaggaaag    15360 aacatgtgag caaaaggcca gcaaaaggcc aggaaccgta aaaaggccgc gttgctggcg    15420 ttttccata ggctccgccc ccctgacgag catcacaaaa atcgacgctc aagtcagagg     15480
tggcgaaacc cgacaggact ataaagatac caggcgtttc ccctggaag ctccctcgtg     15540 cgctctcctg ttccgaccct gccgcttacc ggatacctgt ccgcctttct cccttcggga    15600
agcgtggcgc tttctcatag ctcacgctgt aggtatctca gttcggtgta ggtcgttcgc    15660
tccaagctgg gctgtgtgca cgaaccccc gttcagcccg accgctgcgc cttatccggt     15720
aactatcgtc ttgagtccaa cccggtaaga cacgacttat cgccactggc agcagccact    15780
ggtaacagga ttagcagagc gaggtatgta ggcggtgcta cagagttctt gaagtggtgg    15840
cctaactacg gctacactag aagaacagta tttggtatct gcgctctgct gaagccagtt    15900
accttcggaa aaagagttgg tagctcttga tccggcaaac aaaccaccgc tggtagcggt    15960 ggttttttg tttgcaagca gcagattacg cgcagaaaa aaggatctca agaagatcct      16020
ttgatctttt ctacggggtc tgacgctcag tggaacgaaa actcacgtta agggattttg    16080
gtcatgagat tatcaaaaag gatcttcacc tagatccttt taaattaaaa atgaagtttt    16140
aaatcaatct aaagtatata tgagtaaact tggtctgaca gttaccaatg cttaatcagt    16200
gaggcaccta tctcagcgat ctgtctattt cgttcatcca tagttgcctg actccccgtc    16260
gtgtagataa ctacgatacg ggagggctta ccatctggcc ccagtgctgc aatgataccg    16320
cgagacccac gctcaccggc tccagattta tcagcaataa accagccagc cggaagggcc    16380
gagcgcagaa gtggtcctgc aactttatcc gcctccatcc agtctattaa ttgttgccgg    16440
gaagctagag taagtagttc gccagttaat agtttgcgca acgttgttgc cattgctaca    16500
ggcatcgtgg tgtcacgctc gtcgtttggt atggcttcat tcagctccgg ttcccaacga    16560
tcaaggcgag ttacatgatc ccccatgttg tgcaaaaaag cggttagctc cttcggtcct    16620
ccgatcgttg tcagaagtaa gttggccgca gtgttatcac tcatggttat ggcagcactg    16680
cataattctc ttactgtcat gccatccgta agatgctttt ctgtgactgg tgagtactca    16740
accaagtcat tctgagaata gtgtatgcgg cgaccgagtt gctcttgccc ggcgtcaata    16800
```

| | | | | |
|---|---|---|---|---|
| cgggataata | ccgcgccaca | tagcagaact | ttaaaagtgc | tcatcattgg aaaacgttct | 16860 |
| tcggggcgaa | aactctcaag | gatcttaccg | ctgttgagat | ccagttcgat gtaacccact | 16920 |
| cgtgcaccca | actgatcttc | agcatctttt | actttcacca | gcgtttctgg gtgagcaaaa | 16980 |
| acaggaaggc | aaaatgccgc | aaaaaaggga | ataagggcga | cacggaaatg ttgaatactc | 17040 |
| atactcttcc | tttttcaata | ttattgaagc | atttatcagg | gttattgtct catgagcgga | 17100 |
| tacatatttg | aatgtattta | gaaaaataaa | caaataggggg | ttccgcgcac atttccccga | 17160 |
| aaagtgccac | ctgacgcgcc | ctgtagcggc | gcattaagcg | cggcgggtgt ggtggttacg | 17220 |
| cgcagcgtga | ccgctacact | tgccagcgcc | ctagcgcccg | ctcctttcgc tttcttccct | 17280 |
| tcctttctcg | ccacgttcgc | cggctttccc | cgtcaagctc | taaatcgggg gctcccttta | 17340 |
| gggttccgat | ttagtgcttt | acggcacctc | gaccccaaaa | aacttgatta gggtgatggt | 17400 |
| tcacgtagtg | ggccatcgcc | ctgatagacg | gttttttcgcc | ctttgacgtt ggagtccacg | 17460 |
| ttctttaata | gtggactctt | gttccaaact | ggaacaacac | tcaaccctat ctcggtctat | 17520 |
| tcttttgatt | tataagggat | tttgccgatt | tcggcctatt | ggttaaaaaa tgagctgatt | 17580 |
| taacaaaaat | ttaacgcgaa | ttttaacaaa | atattaa | | 17617 |

<210> SEQ ID NO 2
<211> LENGTH: 2901
<212> TYPE: DNA
<213> ORGANISM: Artificial Sequence
<220> FEATURE:
<223> OTHER INFORMATION: 5' homology arm of targeting vector

<400> SEQUENCE: 2

| | | | | |
|---|---|---|---|---|
| tccctgcaca | gctagtcaca | acgaaggaag | gcgcttaggg | aaccctggca gcttgcaaaa | 60 |
| cgcaaagggc | tacggctgca | tcgctctttt | ccagacttct | cagctgggag cttctggcag | 120 |
| ttttcccgag | tcactccttt | ctctcactag | ctcacaaagt | ggccagctga gtcagaagcc | 180 |
| tccttctagt | acaggcctgc | ctcccaccaa | cgccatcaat | caggacaagt aaggaagact | 240 |
| tctgagtcgc | ccccccccc | caccggtcaa | atagagggga | catcttatca ctgatggcat | 300 |
| cctagattgg | tgatatatgt | aattattttt | gagtgtgcta | cccacgaaca agctatatct | 360 |
| gtttatggtt | gctgttgttt | tggttttttgt | tttcttttaa | ggttctcatc cctcagccac | 420 |
| tgcgggcaaa | aatgagacca | catttgccaa | taagtttgaa | cacgctcaac cctctctttc | 480 |
| tccctcccctt | tctgatagac | aattccttcg | gtaggcagag | gtgagcaatg gcacacggaa | 540 |
| gccttccaga | gctgggatca | gaaaacctct | tgtttgtttg | tctggggaga gggaggttcg | 600 |
| gcaccaaggg | ctaagcaaat | atttgcggtt | atggattaac | ctgactccca gactgacatg | 660 |
| gcgctacctg | gacgaaattg | cagtttctcc | ttggcccacg | cctgtaagtc ccctcattg | 720 |
| caagactgtg | aaggactgtg | gagggagggg | agggagggaa | agtccagctg ggaggaaggt | 780 |
| gacgttcttg | agctaaggct | ctccaggcag | actgaaatgt | ggggccaagg aaaatgagcg | 840 |
| cccaaactct | atctggacca | aggcgtgggt | tccctacaat | ccaggtgacc atctcgacac | 900 |
| atgagatttt | gtggatcaag | tggacagcag | tcaaagggtt | ccctatgatc aggaaccatc | 960 |
| ctcagagcaa | tcttgaaacc | cagaacccca | ctactcccct | ctgccctgtt ctctaaggtg | 1020 |
| gactctacaa | ttccggaagc | cagcaaagcc | gaagagtgag | gccaggaggg gctgtgcagc | 1080 |
| tgggataggc | gggcctgccc | acctggtctg | ggggacacta | gaggccttgt ggtttgacta | 1140 |
| ctggttgggg | gcagggggtta | aggttccaga | gttgggccca | cataggcttg gccttgaagc | 1200 |
| caaactctgc | cctcctctta | ggtgtaggct | tgtgacaagc | cgcgtatctc ctccaagcct | 1260 |

-continued

```
ttgggtccct tcccatgaaa tggaggtgag aatattcatg ccttcctctt ttaacagtga    1320
tcagtgtgtg tgtgtgtgtg tgtgtgtgtg tgtgtgtgtg tgtgtgtgtg tgtgtgtgtg    1380
gtgtagagtg tggtttctgg tgttcagggt tgaacccaga atcttaaaca tgccaagtac    1440
gttctttcct actgaactgc aaccctccag tatcctgtac ttgttgtttg tttgtttgtt    1500
tgtttgtttg ttcggaagca cctgtggtgg cacacactta caatcctagt gctagagagc    1560
agaaacaagt ggatcccttg ggcttgctgg ctggccagcc tacgtgatga gtttcaggca    1620
gtgagagacc ttgtcccaaa caataaggtg gaagtaagcc atgatggcat accccttag     1680 agctagtact cgagaggcag aagcaggtgg agtttaagac cagcctggtc tacatagaag    1740
ttccaggata gccaaaaagt acccaaggcc atccaaaaaa acaaaaacaa aacaaaacct    1800
ggagggaaaa aaaaaaccag acaatgcctg gggaaggatg aaggacagtc agtcagatta    1860
tccctggtca acacgtgtgc acaaatctgt gcacacaaga aagagcttca catgggttac    1920
tatttgtttt ccaacaactc attttttaagc ccccactctc tttctctgtt tttaaaaaag    1980
gtttatttat tttatgtata tgagtacatt attgctctct tcagacacac cagaaaagga    2040
cataagattc cattacagat ggttgtgagc caccatgtgg ttgctggaat ttgaactcag    2100
gtcctctgga agagcagtcg gtgctcttaa ccactgaacc atctccccag cccttccaac    2160
aactctttat ggaagaaacc tattctatcc attttataaa tgacagaact gaggcacgga    2220
gcacgtaaac atcttgttaa atacctctct ctctctctct ctctcccag taggaaatgg     2280 aatttgcccc aggcaatgac ttttttttt tttttttgc tttcatgtac ctagagtaag      2340
cccagctcta aaggccacga gattgtctgt ctgtggaccg tggtgtaccc cactcccaga    2400
cccagcttcc acacagacaa tgagctcaca aacgtccttt actcccttcc ttccttgctt    2460
gctctgtgtg tgtgtgtgtg tgtgtgtgtg tgtgttaaga gatcaacctc agacattttc    2520
tttaggagct atttaccttg ctttttgaga cagggcctcc ggatggcctg gagctagtca    2580
cctggagctg gtcaagcagg ctagggtggc tggcctaagc aatccacagg atctgcttat    2640
ctctgcctcc ccagtcctgg gattacaaga aacgcctcag acaccctagat ttctgttta    2700 attttctatg ggttctgggg atctttctta agtcttcaag tatgcacgga aagggcttta    2760
ttgactaaga tatctcccct gctcaggaat ggccctttca ttctactttg gagggagctg    2820
ggggtggggc ggggagcagc tcagctgtgt gtatccttgg agcttagaag ttctcctcag    2880
acaggtgtca gcagctccag g                                              2901
```

<210> SEQ ID NO 3
<211> LENGTH: 931
<212> TYPE: DNA
<213> ORGANISM: Artificial Sequence
<220> FEATURE:
<223> OTHER INFORMATION: First part of (i.e. 5' portion of) 3' homology
arm of targeting vector

<400> SEQUENCE: 3

```
cacccctccc tgctcacctc tggaccctag aagtcactct tggagtaagg ctgggctagt      60
gagtaccaag acagaggaca ttaaaggagc atgcaacaaa catacctccc cgagtacctg     120
tctgtctttt catccttttt atgggctatt ctggggaaaa gtaacattaa ttgagcatgc     180
actacacacc aagtctatga aaagaacctg cttaactccc aaagcagttg tgtagaagat     240
ctagtgggat ctgagctgat atcacttctg ggggtgagtg gaggagattg atttagagaa     300
aggaattttt ttagaagtta ctgtaagaga ctaatagagc cttctcagg gccttggaaa     360
```

```
gagcccgtgc tagttacatc agaaaagctt gccagtgacc agtggccagt gagactcaga    420
atggccatgt ggtggagcca ggattcaaac caaggtcaca ctcccaaact cagctgcttc    480
tcttctttat tatccctggg tgtgtgctgg tgtgtgtgtg cgcgcgtggg tgtgtgggtg    540
gatacatgca tgtgtgtgtg tgtgtgtgtg tgtgtgtgtg tgtgtgtgtg tgttatatgt    600
ttggagacca gaggacaact tcgtttctca acaccatcca cttgttttgt tttgtgtttt    660
gttttgtttg ttgacacagg gtctctcact gtcctgaaat ctacccagta ggctaggctg    720
gctggctacc aaaccccacc ccaccctggc tttgacaagt ggagacagaa gaccagtagt    780
ccactggaga tgtgaccaga tgcccagaag gtgctcctca tggtgcccta cagttttgtt    840
gaggagtctg tttaataatg cagctgggtg cagtggcagc acctgtagcc cccaatactg    900
aggcagcatt gctgcagtct gagaggtggg g                                   931
```

```
<210> SEQ ID NO 4
<211> LENGTH: 4126
<212> TYPE: DNA
<213> ORGANISM: Artificial Sequence
<220> FEATURE:
<223> OTHER INFORMATION: Second part of (i.e. 3' portion of) 3' homology
      arm of targeting vector

<400> SEQUENCE: 4
acagcctggg caacacagca aaaatccctt cccttaaaaa aaacaaaaga gaaggaagaa     60
ggacgaagta gaatgtggag gacaaacagg ggagagaggg ggaaagaaag ggagggaatt    120
gtcttagagt tttacggctg tgcacagaca ccatgatcaa ggtaactctt gtaaggataa    180
catttagttg gggctggctt acaggttcag aagttcagtc cattatcatc aaggcaggaa    240
catggcagca ttcaaggcag acatggtgca ggaggagctg agagttctac atcttcatct    300
gaagatttct agtagaatac tggcttccag gcagctagga tgagggtctt aaagcccaca    360
cccagtgaca cacctactcc aacagggcca cacctcctaa tcatgccact ccctgggctg    420
agcatataga aaccatcaca gagtctaact agtgtggccc atcctgcacc catggaagac    480
catcactggg gcatagacaa cctccagagc ccaccctgac agttcctgtc tctgccttct    540
ccagcagtca ccagtttcaa atagctcctc aaggacagat ggggccttgt gagcttcacc    600
ccgctgcagc ctggaatgcg ccacctttaa tcccagcact tggaaggcag aggcaggcag    660
atttctgagt tcgaggccag cctagtctac agagtgagtt ccaggacagc cagggcgata    720
cagagaaacc ctgtctcaaa aaacaaaaca aacaaaacg atagaaaaga gcaaagtgac    780
cttgggctat ggatgggatg gaccatcggg cactgggttg ggaagctgaa ctggtccaga    840
tgcccagagc ccagagctct ctcctcagca gttcataacc tggggtgttg ccacagcaca    900
cacagcaagg ttagttctgc tggttgtcgg gacttagggt aggaggagta gaagcctgct    960
actgattctg tctctctctg tttctctctc ctccctccct ccctccttcc ctccctccct   1020
ccctcttctt cttcttctca tcctcctccc tcttcctctt cttcctccac ctccccaccc   1080
cttattttga tacagggttt ctctgtgtat ccctggctgt cctggaactc actctgtagc   1140
ccaggtgggc ctcgaactct cagcctcagt ccccagaatg ctgagaacac aggtctgagt   1200
gatcactgat ggctaaaagt tgggattaca ttgttgttgc ttgtttgttt attcttttgt   1260
acatgggacc caaatacaaa tagtagcctc aacaataaac acgggataag ttgctgctct   1320
gctttagggt ctccctgacc tctgtttttt tgttttttgt tttggtatg ttttgttttc   1380 tgttgttgtt gttatcatgt ctataaatct atcttccttc ctccctcctt ccttcccttc   1440
```

```
ctacttccct ctctttcttc atccctccct tccccctact ctctttcacc cccagatagg   1500
aagcaagcat gataaaaacg tgtggtgttt tccttttat gtagagagta ctgtgtagtg    1560
agtgttatcc tatgggtgct gccattctgc tgtatgttac ctgctgtatg ttataccaac   1620
ctagatggtg gtgaactcac atggttgctt ccatcttggt gaggttacca gccaagatgt   1680
ctgccctcca catgattgcc tccatcttgg tgaggtaaat gtttaataaa gtaacaaaac   1740
aagacattaa aaacaaacat tccagcacaa aatcttcttg agattagaga cataatagga   1800
agtcaggtga ggtcatacag gccattaatc ccatcacttg gggaacagag gcaggtagaa   1860 cttttgaattg aaggcaggta tatttagtga tttccagggc tatgtagaga ggcccctgac   1920
ccaactaata agtaaacagg aagataaata aatataatga acttagaata aaacaaagaa   1980
aggaagaaac aagggaaggc agtgctgggg gcctggctta tggtggatgg gggaattctg   2040
tgctagggtg cctgaaactc tgggctccat cctctgtagt gcataaactc tttggtacgt   2100
tagcccctgt ctgtaacaag gagctgtcca cggttgcagt actgcctttc ccatctcagc   2160 tgccctcag gagctgtcca cagtggcgac actttttcat cctcagccta cagctttagg    2220
gaaacaccac tgcagggct gtcccaaagg tgctgtccac agaggcagca ccttctctgt    2280
ggtctcaccc ctccagacac cccccagcag ccccacaggg atggcacctc agtaaaagcc   2340
aactgtggcc agagaagtct tcctacccta actcatagac tcgatgcagg gaaaacaggg   2400
tgaaaaaaag ccaccaagcc ctgagctccc cccagctcag gacttaaaat ctcatcaatc   2460
ctcactatgg aaatctctgc cttgagaagc tctgccccct cataaatcct atataagaac   2520
tgtccctttg tccagttccc tgccatccgc tcccaggagc agagggcagt tatccctgga   2580
ttcatccctc cacaccctgg acctgccaat aaacctttct tgagatttca tgcttcctgt   2640
gattctcagt ggaagaagcc aagaagaaaa gaaccaaaga gagggagcca ggctgaggct   2700
cctgagttct tcagctcagc tgtggatacc tgtgatggtt tgtatatgct ctgtccaggg   2760
aatggcatga ttagaaggtg tggccctgtt gaagtaggtg tgtcactgtg ggtgtgggct   2820
ataagaccct catcttaact gcatggaagt cattcttcca ctggcagcct tcagatgaaa   2880
atgtagaact ctcagctcct cctgcaccat gcctgcctag atgctgccct gctcccacct   2940
tgatgataat ggactgaacc tctgaacctg taagccagcc ccaattaaat gttgttcttt   3000
ataagtcttg ccttggttgt ggtgtctgtt cacagcagta aaaccatgac taagacaata   3060
tcttctactt ggagctgcaa caactctgct gaggaggctt cctctcagag ctatatggtt   3120
cctggtatct gtaaaattcc cttctattgg gacactttcc aacctcagat ctgtgtggtt   3180
cctggcccct gtgtctcggg atgcccttcc attagaacag cttctcccct cagagctgca   3240
tggttcctgg acttctgagt cccaggagac ccttccatct gagcagaaac acttacagga   3300
gcagagtcct ccaacaccac ggttttgttt tgaaagacca agaccaaccc tcaggaggtt   3360
tctggcaaag gcagattcta ggtgcacctg gaggagacct atagtgcagg accatccgtc   3420
gtaggttgct aggcaccaat gggcaaaggt agggaagaaa tcttaccaga agattctatt   3480
ccattccatt ctcctcacaa tgtaagagcc aaagttaacc tctaaggccc aagaacaagg   3540
taactctcca gaatgctggg agatgtagtt cttgggtaac aacaagccat gttctcgccc   3600
taaacaagtt tgtttgaatc aactacactg aatgtacttg atcatatgta ggagagagaa   3660
gattgattct agttcagggt ttcaggctat ttcagtccac catgatggga aaggcatgac   3720
attgtttatg acagtaagag catgtagcag aggatcctca catcacaaca ggccgaaatg   3780
```

| | |
|---|---|
| cagaggacag tgcaaccaga ggacagtctg taactttcca agtccctctt ctagtgggtt | 3840 |
| gcttccacca cctctcaggt ggtgctacag ctcaggaaca attgagatgt gtgatgaagg | 3900 |
| gcaggtactc aactgtggct gtattgtatc cttttatagt tgtcctctgt gtgttgagct | 3960 |
| atgtgcgaga ttctcaggtc atcggagtac ctgttttact ttggcaggca taggagactc | 4020 |
| ctgagaactc tgcctgacat ccttgccagc ccaagctttg gtttagtgtg tgcagtatca | 4080 |
| ctcttgggtc ttatctgcat atccctgatg gcccatcaag atgtgt | 4126 |

<210> SEQ ID NO 5
<211> LENGTH: 21
<212> TYPE: DNA
<213> ORGANISM: Mouse

<400> SEQUENCE: 5

| | |
|---|---|
| acaggtgtca gcagctccag g | 21 |

<210> SEQ ID NO 6
<211> LENGTH: 104
<212> TYPE: DNA
<213> ORGANISM: Mouse

<400> SEQUENCE: 6

| | |
|---|---|
| caccsctccc tgctcacctc tggaccctag aagtcactct tggagtaagg ctgggctagt | 60 |
| gagtaccaag acagaggaca ttaaaggagc atgcaacaaa cata | 104 |

<210> SEQ ID NO 7
<211> LENGTH: 34
<212> TYPE: DNA
<213> ORGANISM: Artificial Sequence
<220> FEATURE:
<223> OTHER INFORMATION: LoxP site

<400> SEQUENCE: 7

| | |
|---|---|
| ataacttcgt atagcataca ttatacgaag ttat | 34 |

<210> SEQ ID NO 8
<211> LENGTH: 1386
<212> TYPE: DNA
<213> ORGANISM: Human

<400> SEQUENCE: 8

| | |
|---|---|
| atgtggcagc tcacaagcct cctgctgttc gtggccacct ggggaatttc cggcacacca | 60 |
| gctcctcttg actcagtgtt ctccagcagc gagcgtgccc accaggtgct gcggatccgc | 120 |
| aaacgtgcca actccttcct ggaggagctc cgtcacagca gcctggagcg ggagtgcata | 180 |
| gaggagatct gtgacttcga ggaggccaag gaaattttcc aaaatgtgga tgacacactg | 240 |
| gccttctggt ccaagcacgt cgacggtgac cagtgcttgg tcttgccctt ggagcacccg | 300 |
| tgcgccagcc tgtgctgcgg gcacggcacg tgcatcgacg gcatcggcag cttcagctgc | 360 |
| gactgccgca gcggctggga gggccgcttc tgccagcgcg aggtgagctt cctcaattgc | 420 |
| tcgctggaca acggcggctg cacgcattac tgcctagagg aggtgggctg gcggcgctgt | 480 |
| agctgtgcgc ctggctacaa gctggggac gacctcctgc agtgtcaccc cgcagtgaag | 540 |
| ttcccttgtg ggaggccctg gaagcggatg gagaagaagc gcagtcacct gaaacgagac | 600 |
| acagaagacc aagaagacca agtagatccg cggctcattg atgggaagat gaccaggcgg | 660 |
| ggagacagcc cctggcaggt ggtcctgctg gactcaaaga agaagctggc ctgcggggca | 720 |
| gtgctcatcc acccctcctg ggtgctgaca gcggcccact gcatggatga gtccaagaag | 780 |

```
ctccttgtca ggcttggaga gtatgacctg cggcgctggg agaagtggga gctggacctg      840
gacatcaagg aggtcttcgt ccaccccaac tacagcaaga gcaccaccga caatgacatc      900
gcactgctgc acctggccca gcccgccacc ctctcgcaga ccatagtgcc catctgcctc      960
ccggacagcg gccttgcaga gcgcgagctc aatcaggccg ccaggagac cctcgtgacg      1020 ggctggggct accacagcag ccgagagaag gaggccaaga gaaaccgcac cttcgtcctc      1080
aacttcatca agattcccgt ggtcccgcac aatgagtgca gcgaggtcat gagcaacatg      1140
gtgtctgaga acatgctgtg tgcgggcatc ctcggggacc ggcaggatgc ctgcgagggc      1200
gacagtgggg ggcccatggt cgcctccttc cacggcacct ggttcctggt gggcctggtg      1260
agctggggtg agggctgtgg gctccttcac aactacggcg tttacaccaa agtcagccgc      1320
tacctcgact ggatccatgg gcacatcaga gacaaggaag ccccccagaa gagctgggca      1380
ccttag      1386
```

<210> SEQ ID NO 9
<211> LENGTH: 13254
<212> TYPE: DNA
<213> ORGANISM: Artificial Sequence
<220> FEATURE:
<223> OTHER INFORMATION: Section of targeting vector from the 5' end of
      the 5' homology arm to the 3' end of the 3' homology arm

<400> SEQUENCE: 9

```
tccctgcaca gctagtcaca acgaaggaag gcgcttaggg aaccctggca gcttgcaaaa      60
cgcaaagggc tacggctgca tcgctctttt ccagacttct cagctgggag cttctggcag      120
ttttcccgag tcactccttt ctctcactag ctcacaaagt ggccagctga gtcagaagcc      180
tccttctagt acaggcctgc ctcccaccaa cgccatcaat caggacaagt aaggaagact      240
tctgagtcgc cccccccccc caccggtcaa atagagggga catcttatca ctgatggcat      300
cctagattgg tgatatatgt aattatttt gagtgtgcta cccacgaaca agctatatct      360
gtttatggtt gctgttgttt tggtttttgt tttcttttaa ggttctcatc cctcagccac      420
tgcgggcaaa aatgagacca catttgccaa taagtttgaa cacgctcaac cctctctttc      480
tccctccctt tctgatagac aattccttcg gtaggcagag gtgagcaatg gcacacgga      540 gccttccaga gctgggatca gaaaacctct tgtttgtttg tctggggaga gggaggttcg      600
gcaccaaggg ctaagcaaat atttgcggtt atggattaac ctgactccca gactgacatg      660
gcgctacctg gacgaaattg cagtttctcc ttggcccacg cctgtaagtc cccctcattg      720
caagactgtg aaggactgtg gagggagggg aggggaggaa agtccagctg ggaggaaggt      780
gacgttcttg agctaaggct ctccaggcag actgaaatgt ggggccaagg aaaatgagcg      840
cccaaactct atctggacca aggcgtgggt tccctacaat ccaggtgacc atctcgacac      900
atgagatttt gtggatcaag tggacagcag tcaaagggtt ccctatgatc aggaaccatc      960
ctcagagcaa tcttgaaacc cagaaccccca ctactcccct ctgccctgtt ctctaaggtg     1020
gactctacaa ttccggaagc cagcaaagcc gaagagtgag gccaggaggg gctgtgcagc     1080
tgggataggc gggcctgccc acctggtctg ggggacacta gaggcttgt ggtttgacta     1140 ctggttgggg gcaggggtta aggttccaga gttggggcca cataggcttg gccttgaagc     1200
caaactctgc cctcctctta ggtgtaggct tgtgacaagc gcgtatctc tccaagcct      1260 ttgggtccct tcccatgaaa tggaggtgag aatattcatg ccttcctctt ttaacagtga     1320
tcagtgtgtg tgtgtgtgtg tgtgtgtgtg tgtgtgtgtg tgtgtgtgtg tgtgtgtgtg     1380
```

-continued

```
gtgtagagtg tggtttctgg tgttcagggt tgaacccaga atcttaaaca tgccaagtac      1440
gttctttcct actgaactgc aaccctccag tatcctgtac ttgttgtttg tttgtttgtt      1500
tgtttgtttg ttcggaagca cctgtggtgg cacacactta caatcctagt gctagagagc      1560
agaaacaagt ggatcccttg ggcttgctgg ctggccagcc tacgtgatga gtttcaggca      1620
gtgagagacc ttgtcccaaa caataaggtg gaagtaagcc atgatggcat accccttag       1680
agctagtact cgagaggcag aagcaggtgg agtttaagac cagcctggtc tacatagaag      1740
ttccaggata gccaaaaagt acccaaggcc atccaaaaaa acaaaaacaa aacaaaacct      1800
ggagggaaaa aaaaaaccag acaatgcctg gggaaggatg aaggacagtc agtcagatta      1860
tccctggtca cacgtgtgc acaaatctgt gcacacaaga aagagcttca catgggttac       1920
tatttgtttt ccaacaactc attttttaagc ccccactctc tttctctgtt tttaaaaaag     1980
gtttatttat tttatgtata tgagtacatt attgctctct tcagacacac cagaaaagga     2040
cataagattc cattacagat ggttgtgagc caccatgtgg ttgctggaat ttgaactcag     2100
gtcctctgga agagcagtcg gtgctcttaa ccactgaacc atctccccag cccttccaac     2160
aactctttat ggaagaaacc tattctatcc attttataaa tgacagaact gaggcacgga     2220
gcacgtaaac atcttgttaa atacctctct ctctctctct ctctccccag taggaaatgg     2280
aatttgcccc aggcaatgac tttttttttt tttttttgc tttcatgtac ctagagtaag     2340
cccagctcta aaggccacga gattgtctgt ctgtggaccg tggtgtaccc cactcccaga     2400
cccagcttcc acacagacaa tgagctcaca aacgtccttt actcccttcc ttccttgctt     2460
gctctgtgtg tgtgtgtgtg tgtgtgtgtg tgtgttaaga gatcaacctc agacattttc     2520
tttaggagct atttaccttg cttttttgaga cagggcctcc ggatggcctg gagctagtca     2580
cctggagctg gtcaagcagg ctagggtggc tggcctaagc aatccacagg atctgcttat     2640
ctctgcctcc ccagtcctgg gattacaaga aacgcctcag acacctagat ttctgtttta     2700
atttctctatg ggttctgggg atctttctta agtcttcaag tatgcacgga aagggcttta    2760
ttgactaaga tatctcccct gctcaggaat ggcccttca ttctactttg gagggagctg      2820
ggggtggggc ggggagcagc tcagctgtgt gtatccttgg agcttagaag ttctcctcag     2880
acaggtgtca gcagctccag gatgtggcag ctcacaagcc tcctgctgtt cgtggccacc     2940
tggggaattt ccggcacacc agctcctctt gactcagtgt tctccagcag cgagcgtgcc    3000
caccaggtgc tgcggatccg caaacgtgcc aactccttcc tggaggagct ccgtcacagc    3060
agcctggagc gggagtgcat agaggagatc tgtgacttcg aggaggccaa ggaaattttc    3120
caaaatgtgg atgacacact ggccttctgg tccaagcacg tcgacggtga ccagtgcttg    3180
gtcttgccct tggagcaccc gtgcgccagc ctgtgctgcg ggcacggcac gtgcatcgac    3240
ggcatcggca gcttcagctg cgactgccgc agcggctggg agggccgctt ctgccagcgc    3300
gaggtgagct tcctcaattg ctcgctggac aacggcggct gcacgcatta ctgcctagag    3360
gaggtgggct ggcggcgctg tagctgtgcg cctggctaca agctggggga cgacctcctg    3420
cagtgtcacc ccgcagtgaa gttcccttgt gggaggccct ggaagcggat ggagaagaag    3480
cgcagtcacc tgaaacgaga cacagaagac caagaagacc aagtagatcc gcggctcatt    3540
gatgggaaga tgaccaggcg gggagacagc ccctggcagg tggtcctgct ggactcaaag    3600
aagaagctgg cctgcgggc agtgctcatc caccctcct gggtgctgac agcggccac      3660
tgcatggatg agtccaagaa gctccttgtc aggcttggag agtatgacct gcggcgctgg    3720
```

```
gagaagtggg agctggacct ggacatcaag gaggtcttcg tccaccccaa ctacagcaag    3780
agcaccaccg acaatgacat cgcactgctg cacctggccc agcccgccac cctctcgcag    3840
accatagtgc ccatctgcct cccggacagc ggccttgcag agcgcgagct caatcaggcc    3900
ggccaggaga ccctcgtgac gggctggggc taccacagca gccgagagaa ggaggccaag    3960
agaaaccgca ccttcgtcct caacttcatc aagattcccg tggtcccgca caatgagtgc    4020
agcgaggtca tgagcaacat ggtgtctgag aacatgctgt gtgcgggcat cctcggggac    4080
cggcaggatg cctgcgaggg cgacagtggg gggcccatgg tcgcctcctt ccacggcacc    4140
tggttcctgg tgggcctggt gagctggggt gagggctgtg ggctccttca caactacggc    4200
gtttacacca aagtcagccg ctacctcgac tggatccatg gcacatcag agacaaggaa    4260 gcccccagA agagctgggc accttagcac ccctccctgc tcacctctgg acctagaag    4320 tcactcttgg agtaaggctg ggctagtgag taccaagaca gaggacatta aggagcatg    4380 caacaaacat acctcccga gtacctgtct gtcttttcat ccttttatg ggctattctg    4440 ggggaaagta acattaattg agcatgcact acacaccaag tctatgaaaa gaacctgctt    4500
aactcccaaa gcagttgtgt agaagatcta gtgggatctg agctgatatc acttctgggg    4560
gtgagtggag gagattgatt tagagaaagg aattttttta gaagttactg taagagacta    4620
atagagcctt tctcagggcc ttggaaagag cccgtgctag ttacatcaga aaagcttgcc    4680
agtgaccagt ggccagtgag actcagaatg ccatgtggt ggagccagga ttcaaaccaa    4740
ggtcacactc ccaaactcag ctgcttctct tctttattat ccctgggtgt gtgctggtgt    4800
gtgtgtgcgc gcgtgggtgt gtgggtggat acatgcatgt gtgtgtgtgt gtgtgtgtgt    4860
gtgtgtgtgt gtgtgtgtgt tatatgtttg gagaccagag gacaacttcg tttctcaaca    4920
ccatccactt gttttgtttt gtgttttgtt ttgtttgttg acacagggtc tctcactgtc    4980
ctgaaatcta cccagtaggc taggctggct ggctaccaaa ccccaccca cctggctttt    5040 gacaagtgga gacagaagac cagtagtcca ctggagatgt gaccagatgc ccagaaggtg    5100
ctcctcatgg tgccctacag ttttgttgag gagtctgttt aataatgcag ctgggtgcag    5160
tggcagcacc tgtagccccc aatactgagg cagcattgct gcagtctgag aggtggggct    5220
cgagggacct aataacttcg tatagcatac attatacgaa gttatattaa gggttccgca    5280
agctctagtc gagccccagc tggttctttc cgcctcagaa gccatagagc ccaccgcatc    5340
cccagcatgc ctgctattgt cttcccaatc ctccccttg ctgtcctgcc ccaccccacc    5400
ccccagaata gaatgacacc tactcagaca atgcgatgca atttcctcat tttattagga    5460
aaggacagtg ggagtggcac cttccagggt caaggaaggc acggggagg gcaaacaac    5520 agatggctgg caactagaag gcacagtcga ggctgatcag cgagctctag agaattgatc    5580
ccctcagaag aactcgtcaa gaaggcgata gaaggcgatg cgctgcgaat cgggagcggc    5640
gataccgtaa agcacgagga agcggtcagc ccattcgccg ccaagctctt cagcaatatc    5700
acgggtagcc aacgctatgt cctgatagcg gtccgccaca cccagccggc cacagtcgat    5760
gaatccagaa aagcggccat tttccaccat gatattcggc aagcaggcat cgccatgggt    5820
cacgacgaga tcatcgccgt cgggcatgcg cgccttgagc ctggcgaaca gttcggctgg    5880
cgcgagcccc tgatgctctt cgtccagatc atcctgatcg acaagaccgg cttccatccg    5940
agtacgtgct cgctcgatgc gatgtttcgc ttggtggtcg aatgggcagg tagccggatc    6000
aagcgtatgc agccgccgca ttgcatcagc catgatggat actttctcgg caggagcaag    6060
gtgagatgac aggagatcct gccccggcac ttcgcccaat agcagccagt cccttcccgc    6120
```

```
ttcagtgaca acgtcgagca cagctgcgca aggaacgccc gtcgtggcca gccacgatag    6180
ccgcgctgcc tcgtcctgca gttcattcag ggcaccggac aggtcggtct tgacaaaaag    6240
aaccgggcgc ccctgcgctg acagccggaa cacggcggca tcagagcagc cgattgtctg    6300
ttgtgcccag tcatagccga atagcctctc cacccaagcg gccggagaac ctgcgtgcaa    6360
tccatcttgt tcaatggccg atcccatggt ttagttcctc accttgtcgt attatactat    6420
gccgatatac tatgccgatg attaattgtc aacaggctgc aggtcgaaag gcccggagat    6480
gaggaagagg agaacagcgc ggcagacgtg cgcttttgaa gcgtgcagaa tgccgggcct    6540
ccggaggacc ttcgggcgcc cgccccgccc ctgagcccgc ccctgagccc gccccggac    6600 ccacccttc ccagcctctg agcccagaaa gcgaaggagc aaagctgcta ttggccgctg    6660
ccccaaaggc ctaccgcttc cattgctca gcggtgctgt ccatctgcac gagactagtg     6720
agacgtgcta cttccatttg tcacgtcctg cacgacgcga gctgcggggc ggggggggaac    6780 ttcctgacta ggggaggagt agaaggtggc gcgaaggggc caccaaagaa cggagccggt    6840
tggcgcctac cggtggatgt ggaatgtgtg cgaggccaga ggccacttgt gtagcgccaa    6900
gtgcccagcg gggctgctaa agcgcatgct ccagactgcc ttgggaaaag cgcctcccct    6960
acccggtaga atttcgacga cctgcagcca agctagcttc gcgagctcga ccgaacaaac    7020
gacccaacac ccgtgcgttt tattctgtct ttttattgcc gctcagcttt acagtgacaa    7080
tgacggctgg cgactgaata ttagtgctta cagacagcac tacatatttt ccgtcgatgt    7140
tgaaatcctt tctcatatgt caccataaat atcaaataat tatagcaatc atttacgcgt    7200
taatggctaa tcgccatctt ccagcaggcg caccattgcc cctgtttcac tatccaggtt    7260
acggatatag ttcatgacaa tatttacatt ggtccagcca ccagcttgca tgatctccgg    7320
tattgaaact ccagcgcggg ccatatctcg cgcggctccg acacgggcac tgtgtccaga    7380
ccaggccagg tatctctgac cagagtcatc cttagcgccg taaatcaatc gatgagttgc    7440
ttcaaaaatc ccttccaggg cgcgagttga tagctggctg gtggcagatg gcgcggcaac    7500
accatttttt ctgaccccggc aaaacaggta gttattcgga tcatcagcta caccagagac    7560
ggaaatccat cgctcgacca gtttagttac ccccaggcta agtgccttct ctacacctgc    7620
ggtgctaacc agcgttttcg ttctgccaat atggattaac attctcccac cgtcagtacg    7680
tgagatatct ttaaccctga tcctggcaat ttcggctata cgtaacaggg tgttataagc    7740
aatccccaga aatgccagat tacgtatatc ctggcagcga tcgctatttt ccatgagtga    7800
acgaacctgg tcgaaatcag tgcgttcgaa cgctagagcc tgttttgcac gttcaccggc    7860
atcaacgttt tcttttcgga tccgccgcat aaccagtgaa acagcattgc tgtcacttgg    7920
tcgtggcagc ccggaccgac gatgaagcat gtttagctgg cccaaatgtt gctggatagt    7980
ttttactgcc agaccgcgcg cctgaagata tagaagataa tcgcgaacat cttcaggttc    8040
tgcgggaaac catttccggt tattcaactt gcaccatgcc gcccacgacc ggcaaacgga    8100
cagaagcatt ttccaggtat gctcagaaaa cgcctggcga tccctgaaca tgtccatcag    8160
gttcttgcga acctcatcac tcgttgcatc gaccggtaat gcaggcaaat tttggtgtac    8220
ggtcagtaaa ttgacaccct tcctcttctt cttgggcatg gccgcaggaa agcagagccc    8280
tgaagctccc atcaccggcc aataagagcc aagcctgcag tgtgacctca tagagcaatg    8340
tgccagccag cctgaccccca agggccctca ggcttgggca cactgtctct aggaccctga    8400
gagaaagaca tacccatttc tgcttagggc cctgaggatg agcccagggg tggcttggca    8460
```

```
ctgaagcaaa ggacactggg gctcagctgg cagcaaagtg accaggatgc tgaggctttg    8520
acccagaagc cagaggccag aggccaggac ttctcttggt cccagtccac cctcactcag    8580
agctttacca atgccctctg gatagttgtc gggtaacggt ggacgccact gattctctgg    8640
ccagcctagg acttcgccat tccgctgatt ctgctcttcc agccactggc tgaccggttg    8700
gaagtactcc agcagtgcct tggcatccag gcatctgag cctaccaggt ccttcagtac     8760
ctcctgccag ggcctggagc agccagctg caacacctgc ctgccaagca gagtgaccac     8820
tgtgggcaca ggggacacag ggtggggccc acaacagcac cattgtccac ttgtccctca    8880
ctagtaaaag aactctaggg ttgcgggggg tgggggaggt ctctgtgagg ctggtaaggg    8940
atatttgcct ggcccatgga gctagcttgg ctggacgtaa actcctcttc agacctaata    9000
acttcgtata gcatacatta tacgaagtta tattaagggt tattgaatat gatcggaatt    9060
gggctgcagg aattcgatag cttggctgca ggtcgacgta cgtagcaagc ttgatgggcc    9120
ctggtaccac agcctgggca acacagcaaa aatcccttcc cttaaaaaaa acaaaagaga    9180
aggaagaagg acgaagtaga atgtggagga caaacagggg agagaggggg aaagaaaggg    9240
agggaattgt cttagagttt tacggctgtg cacagacacc atgatcaagg taactcttgt    9300
aaggataaca tttagttggg gctggcttac aggttcagaa gttcagtcca ttatcatcaa    9360
ggcaggaaca tggcagcatt caaggcagac atggtgcagg aggagctgag agttctacat    9420
cttcatctga agatttctag tagaatactg gcttccaggc agctaggatg agggtcttaa    9480
agcccacacc cagtgacaca cctactccaa cagggccaca cctcctaatc atgccactcc    9540
ctgggctgag catatagaaa ccatcacaga gtctaactag tgtggcccat cctgcaccca    9600
tggaagacca tcactggggc atagacaacc tccagagccc accctgacag ttcctgtctc    9660
tgccttctcc agcagtcacc agtttcaaat agctcctcaa ggacagatgg ggccttgtga    9720
gcttcacccc gctgcaggct ggaatgcgcc acctttaatc ccagcacttg aaggcagag    9780 gcaggcagat ttctgagttc gaggccagcc tagtctacag agtgagttcc aggacagcca    9840
gggcgataca gagaaaccct gtctcaaaaa acaaaacaaa acaaaacgat agaaaagagc    9900
aaagtgacct tgggctatgg atgggatgga ccatcgggca ctgggttggg aagctgaact    9960
ggtccagatg cccagagccc agagctctct cctcagcagt tcataacctg gggtgttgcc   10020
acagcacaca cagcaaggtt agttctgctg gttgtcggga cttagggtag gaggagtaga   10080
agcctgctac tgattctgtc tctctctgtt tctctctcct ccctccctcc ctccttccct   10140
ccctccctcc ctcttcttct tcttctcatc ctcctccctc ttcctcttct tcctccacct   10200
ccccacccct tattttgata cagggtttct ctgtgtatcc ctggctgtcc tggaactcac   10260
tctgtagccc aggtgggcct cgaactctca gcctcagtcc ccagaatgct gagaacacag   10320
gtctgagtga tcactgatgg ctaaaagttg ggattacatt gttgttgctt gtttgtttat   10380
tcttttgtac atgggaccca aatacaaata gtagcctcaa caataaacac gggataagtt   10440
gctgctctgc tttagggtct ccctgacctc tgttttttg tttttttgttt ttggtatgtt   10500 ttgttttctg ttgttgttgt tatcatgtct ataaatctat cttccttcct ccctccttcc   10560
ttcccttcct acttccctct cttttcttcat ccctcccttc ccctactct ctttcacccc    10620 cagataggaa gcaagcatga taaaaacgtg tggtgttttc ctttttatgt agagagtact   10680
gtgtagtgag tgttatccta tgggtgctgc cattctgctg tatgttacct gctgtatgtt   10740
ataccaacct agatggtggt gaactcacat ggttgcttcc atcttggtga ggttaccagc   10800
caagatgtct gccctccaca tgattgcctc catcttggtg aggtaaatgt ttaataaagt   10860
```

```
aacaaaacaa gacattaaaa acaaacattc cagcacaaaa tcttcttgag attagagaca    10920
taataggaag tcaggtgagg tcatacaggc cattaatccc atcacttggg gaacagaggc    10980
aggtagaact ttgaattgaa ggcaggtata tttagtgatt tccagggcta tgtagagagg    11040
cccctgaccc aactaataag taaacaggaa gataaataaa tataatgaac ttagaataaa    11100
acaaagaaag gaagaaacaa gggaaggcag tgctgggggc ctggcttatg gtggatgggg    11160
gaattctgtg ctagggtgcc tgaaactctg ggctccatcc tctgtagtgc ataaactctt    11220
tggtacgtta gccctgtct gtaacaagga gctgtccacg gttgcagtac tgcctttccc    11280
atctcagctg cccctcagga gctgtccaca gtggcgacac tttttcatcc tcagcctaca    11340
gctttaggga acaccactg caggggctgt cccaaaggtg ctgtccacag aggcagcacc    11400
ttctctgtgg tctcacccct ccagacaccc ccagcagcc cacagggat ggcacctcag    11460
taaaagccaa ctgtggccag agaagtcttc ctaccctaac tcatagactc gatgcaggga    11520
aaacagggt aaaaaaagcc accaagccct gagctccccc cagctcagga cttaaaatct    11580
catcaatcct cactatggaa atctctgcct tgagaagctc tgcccctca taaatcctat    11640
ataagaactg tcccttttgtc cagttccctg ccatccgctc ccaggagcag agggcagtta    11700
tccctggatt catccctcca caccctggac ctgccaataa accttctgg agatttcatg    11760
cttcctgtga ttctcagtgg aagaagccaa gaagaaaaga accaaagaga gggagccagg    11820
ctgaggctcc tgagttcttc agctcagctg tggatacctg tgatggtttg tatatgctct    11880
gtccagggaa tggcatgatt agaaggtgtg gccctgttga agtaggtgtg tcactgtggg    11940
tgtgggctat aagaccctca tcttaactgc atggaagtca ttcttccact ggcagccttc    12000
agatgaaaat gtagaactct cagctcctcc tgcaccatgc ctgcctagat gctgccctgc    12060
tcccaccttg atgataatgg actgaacctc tgaacctgta agccagcccc aattaaatgt    12120
tgttctttat aagtcttgcc ttggttgtgg tgtctgttca cagcagtaaa accatgacta    12180
agacaatatc ttctacttgg agctgcaaca actctgctga ggaggcttcc tctcagagct    12240
atatggttcc tggtatctgt aaaattccct tctattggga cactttccaa cctcagatct    12300
gtgtggttcc tggcccctgt gtctcgggat gcccttccat tagaacagct tctccctca    12360
gagctgcatg gttcctggac ttctgagtcc caggagaccc ttccatctga gcagaaacac    12420
ttacaggagc agagtcctcc aacaccacgg ttttgttttg aaagaccaag accaaccctc    12480
aggaggttc tggcaaaggc agattctagg tgcacctgga ggagacctat agtgcaggac    12540
catccgtcgt aggttgctag gcaccaatgg gcaaaggtag ggaagaaatc ttaccagaag    12600
attctattcc attccattct cctcacaatg taagagccaa agttaacctc taaggcccaa    12660
gaacaaggta actctccaga atgctggag atgtagttct tgggtaacaa caagccatgt    12720
tctcgcccta aacaagtttg tttgaatcaa ctacactgaa tgtacttgat catatgtagg    12780
agagagaaga ttgattctag ttcagggttt caggctattt cagtccacca tgatgggaaa    12840
ggcatgacat tgtttatgac agtaagagca tgtagcagag gatcctcaca tcacaacagg    12900
ccgaaatgca gaggacagtg caaccagagg acagtctgta actttccaag tccctcttct    12960
agtgggttgc ttccaccacc tctcaggtgg tgctacagct caggaacaat tgagatgtgt    13020
gatgaagggc aggtactcaa ctgtggctgt attgtatcct tttatagttg tcctctgtgt    13080
gttgagctat gtgcgagatt ctcaggtcat cggagtacct gttttacttt ggcaggcata    13140
ggagactcct gagaactctg cctgacatcc ttgccagccc aagctttggt ttagtgtgtg    13200
```

```
cagtatcact cttgggtctt atctgcatat ccctgatggc ccatcaagat gtgt        13254

<210> SEQ ID NO 10
<211> LENGTH: 1386
<212> TYPE: DNA
<213> ORGANISM: Mouse

<400> SEQUENCE: 10
atgtggcaat tcagagtctt cctgctgctc atgtccacct ggggaatatc tagcataccg     60
gcccatcctg acccagtgtt ctccagcagc gagcatgccc accaggtgct tcgggtcaga    120
cgtgccaaca gcttcctgga agagatgcgg ccaggcagcc tggaacggga gtgtatggag    180
gagatctgtg acttcgagga ggcccaggag attttccaaa atgtggaaga cacactggcc    240
ttctggatca agtactttga cggtgaccag tgctcggctc cacccttgga ccaccagtgc    300
gacagcccat gctgcgggca tggcacttgc atcgacggca taggcagctt cagctgcagc    360
tgcgataagg gctgggaggg caagttctgt cagcaggagt tgcgcttcca ggactgtcgg    420
gtgaacaatg gcggctgctt gcactactgc ctggaggaga gcaatgggcg gcgctgcgct    480
tgtgccccgg gctatgagct ggcagacgac cacatgcgct gcaagtccac tgtgaatttt    540
ccatgtggga aactggggag gtggatagag aagaaacgca gatcctcaa acgagacaca    600 gacttagaag atgaactgga accagatcca aggatagtca cggaacgct gacgaagcag    660 ggtgacagtc cttggcaggc aatccttctg gactccaaga gaagctggc ctgcggaggg    720 gtgctcatcc acacttcctg ggtgctgacg gcagcccact gcgtggaggg caccaagaag    780
cttaccgtga ggcttggtga gtatgatctg cgacgcaggg accactggga gctggacctg    840
gacatcaagg agatcctcgt ccaccctaac tacacccgga gcagcagtga caacgacatt    900
gctctgctcc gcctagccca gccagccact ctctccaaaa ccatagtgcc catctgcctg    960
ccgaacaatg ggctcgctca gcaggagctc actcaggctg ccaggagac agtggtgaca   1020 ggctggggct atcaaagcga cagaatcaag gatggcagaa ggaaccgcac cttcatcctc   1080
accttcatcc gcatcccttt ggttgctcga aatgagtgcg tggaggtcat gaagaatgtg   1140
gtctcggaga acatgctgtg tgcaggcatc attgggaaca cgagagacgc ctgtgatggt   1200
gacagtgggg ggcccatggt ggtcttcttt cggggtacct ggttcctggt gggcctggtg   1260
agctggggtg agggctgtgg gcacaccaac aactatggca tctacaccaa agtgggaagc   1320
tacctcaaat ggattcacag ttacattggg gaaaagggtg tctcccttaa gagccagaag   1380
ctatag                                                              1386

<210> SEQ ID NO 11
<211> LENGTH: 461
<212> TYPE: PRT
<213> ORGANISM: Human

<400> SEQUENCE: 11

Met Trp Gln Leu Thr Ser Leu Leu Leu Phe Val Ala Thr Trp Gly Ile
1               5                   10                  15

Ser Gly Thr Pro Ala Pro Leu Asp Ser Val Phe Ser Ser Ser Glu Arg
            20                  25                  30

Ala His Gln Val Leu Arg Ile Arg Lys Arg Ala Asn Ser Phe Leu Glu
        35                  40                  45

Glu Leu Arg His Ser Ser Leu Glu Arg Glu Cys Ile Glu Glu Ile Cys
    50                  55                  60

Asp Phe Glu Glu Ala Lys Glu Ile Phe Gln Asn Val Asp Asp Thr Leu
```

```
                 65                  70                  75                  80
Ala Phe Trp Ser Lys His Val Asp Gly Asp Gln Cys Leu Val Leu Pro
                     85                  90                  95

Leu Glu His Pro Cys Ala Ser Leu Cys Cys Gly His Gly Thr Cys Ile
                100                 105                 110

Asp Gly Ile Gly Ser Phe Ser Asp Cys Arg Ser Gly Trp Glu Gly
            115                 120                 125

Arg Phe Cys Gln Arg Glu Val Ser Phe Leu Asn Cys Ser Leu Asp Asn
        130                 135                 140

Gly Gly Cys Thr His Tyr Cys Leu Glu Val Gly Trp Arg Arg Cys
145                 150                 155                 160

Ser Cys Ala Pro Gly Tyr Lys Leu Gly Asp Asp Leu Leu Gln Cys His
                165                 170                 175

Pro Ala Val Lys Phe Pro Cys Gly Arg Pro Trp Lys Arg Met Glu Lys
            180                 185                 190

Lys Arg Ser His Leu Lys Arg Asp Thr Glu Asp Gln Glu Asp Gln Val
        195                 200                 205

Asp Pro Arg Leu Ile Asp Gly Lys Met Thr Arg Arg Gly Asp Ser Pro
    210                 215                 220

Trp Gln Val Val Leu Leu Asp Ser Lys Lys Lys Leu Ala Cys Gly Ala
225                 230                 235                 240

Val Leu Ile His Pro Ser Trp Val Leu Thr Ala Ala His Cys Met Asp
                245                 250                 255

Glu Ser Lys Lys Leu Leu Val Arg Leu Gly Glu Tyr Asp Leu Arg Arg
            260                 265                 270

Trp Glu Lys Trp Glu Leu Asp Leu Asp Ile Lys Glu Val Phe Val His
        275                 280                 285

Pro Asn Tyr Ser Lys Ser Thr Thr Asp Asn Asp Ile Ala Leu Leu His
    290                 295                 300

Leu Ala Gln Pro Ala Thr Leu Ser Gln Thr Ile Val Pro Ile Cys Leu
305                 310                 315                 320

Pro Asp Ser Gly Leu Ala Glu Arg Glu Leu Asn Gln Ala Gly Gln Glu
                325                 330                 335

Thr Leu Val Thr Gly Trp Gly Tyr His Ser Ser Arg Glu Lys Glu Ala
            340                 345                 350

Lys Arg Asn Arg Thr Phe Val Leu Asn Phe Ile Lys Ile Pro Val Val
        355                 360                 365

Pro His Asn Glu Cys Ser Glu Val Met Ser Asn Met Val Ser Glu Asn
    370                 375                 380

Met Leu Cys Ala Gly Ile Leu Gly Asp Arg Gln Asp Ala Cys Glu Gly
385                 390                 395                 400

Asp Ser Gly Gly Pro Met Val Ala Ser Phe His Gly Thr Trp Phe Leu
                405                 410                 415

Val Gly Leu Val Ser Trp Gly Glu Gly Cys Gly Leu Leu His Asn Tyr
            420                 425                 430

Gly Val Tyr Thr Lys Val Ser Arg Tyr Leu Asp Trp Ile His Gly His
        435                 440                 445

Ile Arg Asp Lys Glu Ala Pro Gln Lys Ser Trp Ala Pro
    450                 455                 460

<210> SEQ ID NO 12
<211> LENGTH: 461
<212> TYPE: PRT
<213> ORGANISM: Mouse
```

<400> SEQUENCE: 12

```
Met Trp Gln Phe Arg Val Phe Leu Leu Met Ser Thr Trp Gly Ile
1               5                   10                  15

Ser Ser Ile Pro Ala His Pro Asp Pro Val Phe Ser Ser Ser Glu His
            20                  25                  30

Ala His Gln Val Leu Arg Val Arg Arg Ala Asn Ser Phe Leu Glu Glu
            35                  40                  45

Met Arg Pro Gly Ser Leu Glu Arg Glu Cys Met Glu Glu Ile Cys Asp
50                  55                  60

Phe Glu Glu Ala Gln Glu Ile Phe Gln Asn Val Glu Asp Thr Leu Ala
65                  70                  75                  80

Phe Trp Ile Lys Tyr Phe Asp Gly Asp Gln Cys Ser Ala Pro Pro Leu
                85                  90                  95

Asp His Gln Cys Asp Ser Pro Cys Cys Gly His Gly Thr Cys Ile Asp
            100                 105                 110

Gly Ile Gly Ser Phe Ser Cys Ser Cys Asp Lys Gly Trp Glu Gly Lys
            115                 120                 125

Phe Cys Gln Gln Glu Leu Arg Phe Gln Asp Cys Arg Val Asn Asn Gly
130                 135                 140

Gly Cys Leu His Tyr Cys Leu Glu Glu Ser Asn Gly Arg Arg Cys Ala
145                 150                 155                 160

Cys Ala Pro Gly Tyr Glu Leu Ala Asp Asp His Met Arg Cys Lys Ser
                165                 170                 175

Thr Val Asn Phe Pro Cys Gly Lys Leu Gly Arg Trp Ile Glu Lys Lys
            180                 185                 190

Arg Lys Ile Leu Lys Arg Asp Thr Asp Leu Glu Asp Glu Leu Glu Pro
            195                 200                 205

Asp Pro Arg Ile Val Asn Gly Thr Leu Thr Lys Gln Gly Asp Ser Pro
210                 215                 220

Trp Gln Ala Ile Leu Leu Asp Ser Lys Lys Lys Leu Ala Cys Gly Gly
225                 230                 235                 240

Val Leu Ile His Thr Ser Trp Val Leu Thr Ala Ala His Cys Val Glu
                245                 250                 255

Gly Thr Lys Lys Leu Thr Val Arg Leu Gly Glu Tyr Asp Leu Arg Arg
            260                 265                 270

Arg Asp His Trp Glu Leu Asp Leu Asp Ile Lys Glu Ile Leu Val His
            275                 280                 285

Pro Asn Tyr Thr Arg Ser Ser Ser Asp Asn Asp Ile Ala Leu Leu Arg
290                 295                 300

Leu Ala Gln Pro Ala Thr Leu Ser Lys Thr Ile Val Pro Ile Cys Leu
305                 310                 315                 320

Pro Asn Asn Gly Leu Ala Gln Gln Glu Leu Thr Gln Ala Gly Gln Glu
                325                 330                 335

Thr Val Val Thr Gly Trp Gly Tyr Gln Ser Asp Arg Ile Lys Asp Gly
            340                 345                 350

Arg Arg Asn Arg Thr Phe Ile Leu Thr Phe Ile Arg Ile Pro Leu Val
            355                 360                 365

Ala Arg Asn Glu Cys Val Glu Val Met Lys Asn Val Val Ser Glu Asn
370                 375                 380

Met Leu Cys Ala Gly Ile Ile Gly Asn Thr Arg Asp Ala Cys Asp Gly
385                 390                 395                 400

Asp Ser Gly Gly Pro Met Val Val Phe Phe Arg Gly Thr Trp Phe Leu
```

```
                        405                 410                 415
Val Gly Leu Val Ser Trp Gly Glu Gly Cys Gly His Thr Asn Asn Tyr
            420                 425                 430

Gly Ile Tyr Thr Lys Val Gly Ser Tyr Leu Lys Trp Ile His Ser Tyr
            435                 440                 445

Ile Gly Glu Lys Gly Val Ser Leu Lys Ser Gln Lys Leu
            450                 455                 460
```

```
<210> SEQ ID NO 13
<211> LENGTH: 24
<212> TYPE: DNA
<213> ORGANISM: Artificial Sequence
<220> FEATURE:
<223> OTHER INFORMATION: Neo-F (P1) primer

<400> SEQUENCE: 13
aggctggtaa gggatatttg cctg                                          24

<210> SEQ ID NO 14
<211> LENGTH: 24
<212> TYPE: DNA
<213> ORGANISM: Artificial Sequence
<220> FEATURE:
<223> OTHER INFORMATION: 3'arm-R (P2) primer

<400> SEQUENCE: 14
gagtgagccc agacccataa caat                                          24

<210> SEQ ID NO 15
<211> LENGTH: 25
<212> TYPE: DNA
<213> ORGANISM: Artificial Sequence
<220> FEATURE:
<223> OTHER INFORMATION: 5'arm-F (P3) primer

<400> SEQUENCE: 15
tgggattaca agaaacgcct cagac                                         25

<210> SEQ ID NO 16
<211> LENGTH: 22
<212> TYPE: DNA
<213> ORGANISM: Artificial Sequence
<220> FEATURE:
<223> OTHER INFORMATION: KI-R (P4) primer

<400> SEQUENCE: 16
aggagttggc acgtttgcgg at                                            22

<210> SEQ ID NO 17
<211> LENGTH: 25
<212> TYPE: DNA
<213> ORGANISM: Artificial Sequence
<220> FEATURE:
<223> OTHER INFORMATION: KI-F (F1) primer

<400> SEQUENCE: 17
tgggattaca agaaacgcct cagac                                         25

<210> SEQ ID NO 18
<211> LENGTH: 22
<212> TYPE: DNA
<213> ORGANISM: Artificial Sequence
<220> FEATURE:
<223> OTHER INFORMATION: KI-R (R1) primer
```

<400> SEQUENCE: 18
aggagttggc acgtttgcgg at                                              22

<210> SEQ ID NO 19
<211> LENGTH: 24
<212> TYPE: DNA
<213> ORGANISM: Artificial Sequence
<220> FEATURE:
<223> OTHER INFORMATION: KI2-F (F2) primer

<400> SEQUENCE: 19
ggctgtgggc tccttcacaa ctac                                            24

<210> SEQ ID NO 20
<211> LENGTH: 27
<212> TYPE: DNA
<213> ORGANISM: Artificial Sequence
<220> FEATURE:
<223> OTHER INFORMATION: KI2-R (R2) primer

<400> SEQUENCE: 20
caggttcttt tcatagactt ggtgtgt                                         27

<210> SEQ ID NO 21
<211> LENGTH: 24
<212> TYPE: DNA
<213> ORGANISM: Artificial Sequence
<220> FEATURE:
<223> OTHER INFORMATION: Neo-del-F (F3) primer

<400> SEQUENCE: 21
agggacctaa taacttcgta tagc                                            24

<210> SEQ ID NO 22
<211> LENGTH: 24
<212> TYPE: DNA
<213> ORGANISM: Artificial Sequence
<220> FEATURE:
<223> OTHER INFORMATION: Neo-del-R (R3) primer

<400> SEQUENCE: 22
cctgtttgtc ctccacattc tact                                            24

<210> SEQ ID NO 23
<211> LENGTH: 22
<212> TYPE: DNA
<213> ORGANISM: Artificial Sequence
<220> FEATURE:
<223> OTHER INFORMATION: WT-F (F4) primer

<400> SEQUENCE: 23
catctacacc aaagtgggaa gc                                              22

<210> SEQ ID NO 24
<211> LENGTH: 27
<212> TYPE: DNA
<213> ORGANISM: Artificial Sequence
<220> FEATURE:
<223> OTHER INFORMATION: KI2-R (R2) primer

<400> SEQUENCE: 24
caggttcttt tcatagactt ggtgtgt                                         27

<210> SEQ ID NO 25
<211> LENGTH: 25

```
<212> TYPE: DNA
<213> ORGANISM: Artificial Sequence
<220> FEATURE:
<223> OTHER INFORMATION: Seq-F (F1) primer

<400> SEQUENCE: 25
tgggattaca agaaacgcct cagac                                          25

<210> SEQ ID NO 26
<211> LENGTH: 24
<212> TYPE: DNA
<213> ORGANISM: Artificial Sequence
<220> FEATURE:
<223> OTHER INFORMATION: Seq-R (R3) primer

<400> SEQUENCE: 26
cctgtttgtc ctccacattc tact                                           24

<210> SEQ ID NO 27
<211> LENGTH: 25
<212> TYPE: DNA
<213> ORGANISM: Artificial Sequence
<220> FEATURE:
<223> OTHER INFORMATION: hproC 1-F primer

<400> SEQUENCE: 27
tgggattaca agaaacgcct cagac                                          25

<210> SEQ ID NO 28
<211> LENGTH: 22
<212> TYPE: DNA
<213> ORGANISM: Artificial Sequence
<220> FEATURE:
<223> OTHER INFORMATION: hproC 1-R primer

<400> SEQUENCE: 28
aggagttggc acgtttgcgg at                                             22

<210> SEQ ID NO 29
<211> LENGTH: 22
<212> TYPE: DNA
<213> ORGANISM: Artificial Sequence
<220> FEATURE:
<223> OTHER INFORMATION: mproC -F primer

<400> SEQUENCE: 29
catctacacc aaagtgggaa gc                                             22

<210> SEQ ID NO 30
<211> LENGTH: 27
<212> TYPE: DNA
<213> ORGANISM: Artificial Sequence
<220> FEATURE:
<223> OTHER INFORMATION: mproC -R primer

<400> SEQUENCE: 30
caggttcttt tcatagactt ggtgtgt                                        27
```

```
<210> SEQ ID NO 31
<211> LENGTH: 20
<212> TYPE: DNA
<213> ORGANISM: Artificial Sequence
<220> FEATURE:
<223> OTHER INFORMATION: F8-Common primer

<400> SEQUENCE: 31
gagcaaattc ctgtactgac                                              20

<210> SEQ ID NO 32
<211> LENGTH: 20
<212> TYPE: DNA
<213> ORGANISM: Artificial Sequence
<220> FEATURE:
<223> OTHER INFORMATION: F8-WT-Forward primer

<400> SEQUENCE: 32
tgcaaggcct gggcttattt                                              20

<210> SEQ ID NO 33
<211> LENGTH: 20
<212> TYPE: DNA
<213> ORGANISM: Artificial Sequence
<220> FEATURE:
<223> OTHER INFORMATION: F8-Mut-Forward primer

<400> SEQUENCE: 33
tgtgtcccgc cccttccttt                                              20

<210> SEQ ID NO 34
<211> LENGTH: 23
<212> TYPE: DNA
<213> ORGANISM: Artificial Sequence
<220> FEATURE:
<223> OTHER INFORMATION: F9-Common primer

<400> SEQUENCE: 34
aacagggata gtaagattgt tcc                                          23

<210> SEQ ID NO 35
<211> LENGTH: 22
<212> TYPE: DNA
<213> ORGANISM: Artificial Sequence
<220> FEATURE:
<223> OTHER INFORMATION: F9-WT primer

<400> SEQUENCE: 35
tggaagcagt atgttggtaa gc                                           22

<210> SEQ ID NO 36
<211> LENGTH: 21
<212> TYPE: DNA
<213> ORGANISM: Artificial Sequence
<220> FEATURE:
<223> OTHER INFORMATION: F9-Mut primer

<400> SEQUENCE: 36
tcctgtcatc tcaccttgct c                                            21
```

The invention claimed is:

1. A genetically modified mouse, in which both copies of the endogenous nucleotide sequence encoding Protein C in the genome of said mouse have been replaced by a nucleotide sequence encoding human Protein C.

2. The genetically modified mouse of claim 1, wherein said nucleotide sequence encoding human Protein C comprises the nucleotide sequence of SEQ ID NO:8.

3. The genetically modified mouse of claim 1, wherein expression of said nucleotide sequence encoding human Protein C is under the control of the endogenous regulatory sequences of the Protein C gene of the mouse.

4. The genetically modified mouse of claim 1, wherein the start codon of the nucleotide sequence encoding human Protein C is positioned in the Protein C gene in the genome of the mouse at the position corresponding to the start codon of the nucleotide sequence encoding endogenous Protein C, and the stop codon of the nucleotide sequence encoding human Protein C is positioned in the Protein C gene in the genome of the mouse at the position corresponding to the stop codon of the nucleotide sequence encoding endogenous Protein C.

5. The genetically modified mouse of claim 1, wherein a gene encoding Factor VIII is knocked-out and/or a gene encoding Factor IX is knocked out.

6. A cell, or cell line, derived from the genetically modified mouse of claim 1, in which at least one copy of the endogenous nucleotide sequence encoding Protein C in the genome of said cell or cell line has been replaced by a nucleotide sequence encoding human Protein C.

* * * * *